United States Patent [19]

Delucca

[11] Patent Number: 5,763,469
[45] Date of Patent: Jun. 9, 1998

[54] SUBSTITUTED CYCLIC UREAS AND DERIVATIVES THEREOF USEFUL AS RETROVIRAL PROTEASE INHIBITORS

[75] Inventor: George Vincent Delucca, Wilmington, Del.

[73] Assignee: The DuPont Merck Pharmaceutical Company, Wilmington, Del.

[21] Appl. No.: 701,112

[22] Filed: Aug. 21, 1996

Related U.S. Application Data

[60] Provisional application No. 60/002,653 Aug. 23, 1995 and provisional application No. 60/009,417 Dec. 12, 1995.

[51] Int. Cl.⁶ .................... A61K 31/415; C07D 233/02
[52] U.S. Cl. .................... 514/392; 514/387; 514/388; 548/303.1; 548/303.7; 548/311.1; 548/312.7; 548/322.5; 548/331.5; 548/332.1
[58] Field of Search .................... 548/311, 322.5, 548/331.5, 332.1, 303.1, 303.7, 311.1, 312.7; 514/387, 388, 392

[56] References Cited

U.S. PATENT DOCUMENTS

| | | | |
|---|---|---|---|
| 3,759,933 | 9/1973 | Robison et al. | 546/118 |
| 4,174,958 | 11/1979 | Pilgram | 548/231 |
| 4,894,463 | 1/1990 | Blum | 548/303 |
| 5,095,118 | 3/1992 | Poetsch et al. | 548/154 |
| 5,205,861 | 4/1993 | Matrick | 106/22 |
| 5,250,699 | 10/1993 | Casutt et al. | 548/319.1 |
| 5,276,049 | 1/1994 | Himmelsbach et al. | 514/392 |
| 5,371,102 | 12/1994 | Doerge | 514/387 |
| 5,436,351 | 7/1995 | Coffey et al. | 548/324.1 |

FOREIGN PATENT DOCUMENTS

| | | |
|---|---|---|
| 2074685 | 1/1993 | Canada. |
| 2105934 | 3/1994 | Canada. |
| 0301270 | 2/1989 | European Pat. Off.. |
| 0498629 | 8/1992 | European Pat. Off.. |
| 0628310 | 12/1994 | European Pat. Off.. |
| 0628555 | 12/1994 | European Pat. Off.. |
| 2508831 | 9/1975 | Germany. |
| 2741450 | 3/1978 | Germany. |
| 50-088086 | 7/1975 | Japan. |
| 63-243079 | 10/1988 | Japan. |
| 90 00407 | 1/1990 | WIPO. |
| 90 04588 | 5/1990 | WIPO. |
| 9209297 | 6/1992 | WIPO. |
| 9221647 | 12/1992 | WIPO. |
| 9408977 | 4/1994 | WIPO. |
| 9419329 | 9/1994 | WIPO. |
| 9422840 | 10/1994 | WIPO. |
| 9503044 | 2/1995 | WIPO. |

OTHER PUBLICATIONS

Dhas, S.K.; Wadodkar, S. G., and Kasture, A. V., Indian Drugs 1987, 25(3), 132. "Synthesis of 5–Ethoxy–1,3–disubstituted Benzimidazolin–2–thiones as Antiinflammatory–Analgesic Agents".

Laviell, Solange; Bory, Sonia; Moreau, Bernard; Luche, M. Jacqueline; and Marquet, Andree, J. Am. Chem. Soc. 1978, 100(5), 1558–63. "A Total Synthesis of Biotin Based on the Stereoselective Alkylation of Sulfoxides".

P.Y.S. Lam, P.K. Jadhav, C.J. Eyermann, C.N. Hodge, Y. Ru, L.T. Bacheler, J.L. Meek, M.J. Otto, M.M Rayner, Y.N. Wong, C.H.Chang, P.C.Weber, D.A. Jackson, T.R. Sharpe, S. Erickson–Viitanen, Science 1994, 263, 380–84. "Rational Design of Potent, Bioavailable, Nonpeptide Cyclic Ureas as HIV Protease Inhibitors".

Primary Examiner—Yogendra N. Gupta
Attorney, Agent, or Firm—Gerald J. Boudreaux; David H. Vance

[57] ABSTRACT

The present invention relates to substituted cyclic ureas and analogs thereof of formula (I):

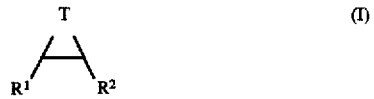

wherein, T is selected from: —N(R²²)C(=Z)N(R²³)—; —N(R²²)C(=Z)C(=Z)N(R²³)—; —N(R²²)S(=Z')N(R²³)—; —N(R²²)S(=Z')₂N(R²³)—; or —N(R²²)P(=O)(R²⁴ᵃ)N(R²³)—;

Z is O, S, NR²⁴; and,

Z' is O or NR²⁴;

or pharmaceutically acceptable salt forms or prodrugs thereof, which are useful as retroviral protease inhibitors, and to pharmaceutical compositions comprising such compounds and methods of using the same for treating viral infection.

18 Claims, No Drawings

SUBSTITUTED CYCLIC UREAS AND DERIVATIVES THEREOF USEFUL AS RETROVIRAL PROTEASE INHIBITORS

This application is a continuation of provisional application Ser. No. 60/002,653, filed on Aug. 23, 1995 and application Ser. No. 60/009,417, filed on Dec. 29, 1995.

FIELD OF THE INVENTION

This invention relates generally to substituted cyclic ureas and analogs thereof useful as retroviral protease inhibitors, pharmaceutical compositions comprising the same, and methods of using the same for treating viral infection.

BACKGROUND OF THE INVENTION

Current treatments for viral diseases usually involve administration of compounds that inhibit viral DNA synthesis. Current treatments for AIDS (Dagani, *Chem. Eng. News*, Nov. 23, 1987 pp. 41–49) involve administration of compounds such as 2',3'-dideoxycytidine, trisodium phosphonoformate, ammonium 21-tungsto-9-antimoniate, 1-b-D-ribofuranoxyl-1,2,4-triazole-3-carboxamide, 3'-azido-3'-deoxythymidine (AZT), and adriamycin that inhibit viral DNA synthesis; compounds such as AL-721 and polymannoacetate which may prevent HIV from penetrating the host cell; and compounds which treat the opportunistic infections caused by the immunosupression resulting from HIV infection. None of the current AIDS treatments have proven to be totally effective in treating and/or reversing the disease. In addition, many of the compounds currently used to treat AIDS cause adverse side effects including low platelet count, renal toxicity, and bone marrow cytopenia.

Proteases are enzymes which cleave proteins at specific peptide bonds. Many biological functions are controlled or mediated by proteases and their complementary protease inhibitors. The genomes of retroviruses encode a protease that is responsible for the proteolytic processing of one or more polyprotein precursors such as the pol and gag gene products. See Wellink, *Arch. Virol.* 98 1 (1988). Retroviral proteases most commonly process the gag precursor into the core proteins, and also process the pol precursor into reverse transcriptase and retroviral protease.

The correct processing of the precursor polyproteins by the retroviral protease is necessary for the assembly of the infectious virions. It has been shown that in vitro mutagenesis that produces protease-defective virus leads to the production of immature core forms which lack infectivity. See Crawford et al., *J. Virol.* 53 899 (1985); Katoh et al., *Virology* 145 280 (1985). Therefore, retroviral protease inhibition provides an attractive target for antiviral therapy. See Mitsuya, *Nature* 325 775 (1987).

The ability to inhibit a viral protease provides a method for blocking viral replication and therefore a treatment for viral diseases, such as AIDS, that may have fewer side effects, be more efficacious, and be less prone to drug resistance when compared to current treatments.

WO93/07128 discloses cyclic carbonyls as inhibitors of HIV protease and synthetic procedures for preparing HIV protease inhibitors.

WO92/21647 discloses cyclic carbonyls and sulfones as inhibitors of HIV protease.

Due to the pressing need for additional HIV related treatments, it is desirable to find new retroviral protease inhibitors. Thus, the present invention concerns novel substituted cyclic ureas and analogs thereof, which compounds are capable of inhibiting viral protease and which compounds are believed to serve as a means of combating viral diseases, such as AIDS. None of the above references teach or suggest the cyclic ureas of the present invention as inhibitors of HIV protease or for treatment of retroviral diseases, i.e., AIDS. The substituted cyclic ureas, and analogs thereof, provided by the present invention are particularly useful as inhibitors of HIV protease and similar retroviral proteases. The compounds of the present invention are of low molecular weight and may, therefore, have good oral absorption properties in mammals.

SUMMARY OF THE INVENTION

Accordingly, one object of the present invention is to provide novel retroviral protease inhibitors.

It is another object of the present invention is to provide a method for treating viral infections which comprises administering to a host in need of such treatment a therapeutically effective amount of at least one of the compounds of the present invention or a pharmaceutically acceptable salt or prodrug form thereof.

It is another object of the present invention to provide pharmaceutical compositions with retroviral protease inhibiting activity comprising a pharmaceutically acceptable carrier and a therapeutically effective amount of at least one of the compounds of the present invention or a pharmaceutically acceptable salt or prodrug form thereof.

These and other objects, which will become apparent during the following detailed description, have been achieved by the inventors' discovery that compounds of formula (I):

or a pharmaceutically acceptable salt form or prodrug thereof, wherein:

$R^1$ is —$C(R^4)(R^{4a})R^5$;

$R^2$ is —$C(R^7)(R^{7a})R^6$;

alternately, $R^1$ and $R^2$ can be taken together with the carbons to which they are attached to form a saturated, unsaturated or aromatic 5–7 membered carbocyclic or heterocyclic ring, said carbocyclic or heterocyclic ring being optionally substituted with 0–5 $R^5$, $R^6$, $R^4$, $R^{4a}$, $R^7$ or $R^{7a}$;

$R^4$ and $R^7$ are independently selected from the following: hydrogen; —$CO_2R^{13}$; —$NR^{11}R^{13}$; $C_1$–$C_8$ alkyl substituted with 0–3 $R^{11}$; $C_2$–$C_8$ alkenyl substituted with 0–3 $R^{11}$; $C_2$–$C_8$ alkynyl substituted with 0–3 $R^{11}$; a $C_3$–$C_{14}$ carbocyclic ring system substituted with 0–3 $R^{11}$ or $R^{12}$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{4a}$ and $R^{7a}$ are independently selected from the following:

hydrogen; $CO_2R^{13}$; $C_1$–$C_4$ alkyl unsubstituted or substituted with halogen or $C_1$–$C_2$ alkoxy; or benzyl unsubstituted or substituted with halogen or $C_1$–$C_2$ alkoxy;

$R^4$ and $R^{4a}$ can alternatively join to form a 5–7 membered carbocyclic ring substituted with 0–2 $R^{12}$;

$R^7$ and $R^{7a}$ can alternatively join to form a 5–7 membered carbocyclic ring substituted with 0–2 $R^{12}$;

$R^5$ and $R^6$ are independently selected from the following: hydrogen, halogen, $-N(R^{20})2$, $-SR^{20}$, $-OR^{20}$, or $C_1-C_6$ alkyl substituted with 0–3 $R^{11}$;

$R^5$ and $R^6$ can alternatively join to form $-OCH_2SCH_2O-$, $-OS(=O)O-$, $-OC(=O)O-$, $-OCH_2O-$, $-OC(=S)O-$, $-OC(=O)$ $C(=O)$ $O-$, $-OC(CH_3)_2O-$, $-OC((CH_2)_3NH_2)(CH_3)O-$, $-OCH_2OCH_2O-$, $-OC(OCH3)(CH_2CH_2CH_3)O-$, $-NHC(=O)NH-$, $-OC(=O)NH-$, $-NHC(=O)$ $O-$, $-NHCH_2O-$, $-OCH_2NH-$, $-NHC(=S)$ $O-$, $-OS(=O)NH-$, $-NHC(=O)C(=O)O-$, $-OC(=O)C(=O)NH-$, $-NHC(=O)C(=O)NH-$, $-NHC(CH_3)_2O-$, $-OC(CH_3)_2NH-$ or any group that, when administered to a mammalian subject, cleaves to form a free dihydroxyl or diamino or hydroxyl and amino;

$R^5$ and $R^{4a}$ can alternatively join to form $=O$, $=S$, or a ketal ring;

$R^6$ and $R^{7a}$ can alternatively join to form $=O$, $=S$, or a ketal ring;

$R^{11}$ is selected from the following:

hydrogen; keto; halogen; cyano; $-CH_2NR^{13}R^{14}$; $-NR^{13}R^{14}$; $-CO_2R^{13}$; $-OC(=O)R^{13}$; $-OR^{13}$; $-S(O)_mR^{13}$; $-C(=O)NR^{13}R^{14}$; $-SO_2NR^{13}R^{14}$; $C_2-C_4$ alkenyl; $C_3-C_6$ cycloalkylmethyl; nitro; $C_7-C_{10}$ arylalkyl; formyl; $C_3-C_6$ cycloalkoxy; methylenedioxy; ethylenedioxy; $C_1-C_4$ haloalkyl; $C_1-C_4$ haloalkoxy; $C_1-C_4$ alkoxycarbonyl; pyridylcarbonyloxy; $C_1-C_4$ alkylcarbonyl; $C_3-C_{10}$ cycloalkyl substituted with 0–2 $R^{12}$; $C_1-C_4$ alkyl substituted with 0–2 $R^{12}$; aryl-$C_1-C_3$ alkyl substituted with 0–2 $R^{12}$; $C_{2-6}$ alkoxy-$C_{2-6}$ alkyl substituted with 0–2 $R^{12}$; a $C_5-C_{14}$ carbocyclic residue substituted with 0–3 $R^{12}$; a 5- to 10-membered heterocyclic ring system containing 1 to 3 heteroatoms independently selected from oxygen, nitrogen or sulfur, said heterocyclic ring system being substituted with 0–3 $R^{12}$;

$R^{11a}$ is selected from the following:

hydrogen; keto; halogen; cyano; $-CH_2NH_2$; $-NH_2$; $-NH$ $(C_1-C_3$ alkyl); $-CO_2H$; $-OC(=O)$ $(C_1-C_3$ alkyl); $-OH$; $C_{1-6}$ alkoxy-$C_{1-6}$ alkyl; $-C(=O)NH_2$; $-SO_2NH_2$; $C_1-C_4$ alkyl; $C_2-C_4$ alkenyl; $C_3-C_{10}$ cycloalkyl; $C_3-C_6$ cycloalkylmethyl; phenoxy; benzyloxy; nitro; $C_3-C_6$ cycloalkoxy; $C_1-C_4$ alkyl substituted with $-NH_2$; $C_1-C_4$ hydroxyalkyl; methylenedioxy; ethylenedioxy; $C_1-C_4$ haloalkyl; $C_1-C_4$ haloalkoxy; $C_1-C_4$ alkoxycarbonyl; $C_1-C_4$ alkylcarbonyloxy; $C_1-C_4$ alkylcarbonyl; $C_1-C_4$ alkylcarbonylamino; 2-(1-morpholino) ethoxy; aryl-$C_1-C_3$ alkyl;

a $C_5-C_{14}$ carbocyclic residue; a 5- to 10-membered heterocyclic ring system containing 1 to 3 heteroatoms independently selected from oxygen, nitrogen or sulfur, said heterocyclic ring system substituted with 0–3 $R^{12a}$;

$R^{12}$, when a substituent on carbon, is selected from the following:

phenyl; halogen; hydroxy; nitro; cyano; $C_1-C_4$ alkyl substituted with 0–2 $OR^{13}$; $C_3-C_6$ cycloalkyl; $C_3-C_6$ cycloalkylmethyl; $C_7-C_{10}$ arylalkyl; $C_1-C_4$ alkoxy; $-CO_2H$; hydroxamic acid; hydrazide; boronic acid; sulfonamide; formyl; $C_3-C_6$ cycloalkoxy; $-OR^{13}$; $-NR^{13}R^{14}$; $C_1-C_4$ alkyl substituted with $-NR^{13}R^{14}$; $C_{2-6}$ alkoxy $C_{2-6}$ alkyl substituted with 0 or 1 $-Si(CH_3)_3$; $C_1-C_4$ hydroxyalkyl; methylenedioxy; ethylenedioxy; $C_1-C_4$ haloalkyl; $C_1-C_4$ haloalkoxy; $C_1-C_4$ alkoxycarbonyl; $C_1-C_4$ alkylcarbonyloxy; $C_1-C_4$ alkylcarbonyl;

$C_1-C_4$ alkylcarbonylamino; $-S(O)_mR^{13}$; $-SO_2NR^{13}R^{14}$; $-NHSO_2R^{14}$; $-OCH_2CO_2R^{13}$; 2-(1-morpholino)ethoxy; $-C(R^{14})=N(OR^{13})$;

a 5- or 6-membered heterocyclic ring containing from 1 to 3 heteroatoms independently selected from oxygen, nitrogen or sulfur, the heterocyclic ring system being substituted with 0–3 $R^{12a}$;

a 3- or 4- carbon chain attached to adjacent carbons on the ring to which it is appended to form a fused 5- or 6-membered ring, said 5- or 6- membered ring being optionally substituted on any of the aliphatic carbons with halogen, $C_1-C_4$ alkyl, $C_1-C_4$ alkoxy, hydroxy, $-NR^{13}R^{14}$; or when $R^{12}$ is attached to a saturated carbon atom, it may be $=O$ or $=S$, or when $R^{12}$ is attached to sulfur it may be $=O$;

$R^{12}$, when a substituent on nitrogen, is selected from the following:

phenyl; benzyl; phenethyl; hydroxy; $C_1-C_4$ hydroxyalkyl; $C_1-C_4$ alkoxy; $C_1-C_4$ alkyl; $C_3-C_6$ cycloalkyl; $C_3-C_6$ cycloalkylmethyl; $-CH_2NR^{13}R^{14}$; $-NR^{13}R^{14}$; $C_{1-6}$ alkoxy-$C_{1-6}$ alkyl; $C_1-C_4$ haloalkyl; $C_1-C_4$ alkoxycarbonyl; $-CO_2H$; $C_1-C_4$ alkylcarbonyloxy; $C_1-C_4$ alkylcarbonyl;

$R^{12a}$, when a substituent on carbon, is selected from one or more of the following:

phenyl; benzyl; phenethyl; phenoxy; benzyloxy; halogen; hydroxy; nitro; cyano; $C_1-C_4$ alkyl; $C_3-C_6$ cycloalkyl; $C_3-C_6$ cycloalkylmethyl; $C_7-C_{10}$ arylalkyl; $C_1-C_4$ alkoxy; $-CO_2H$; formyl; $C_3-C_6$ cycloalkoxy; $-OH^{13}$; $C_1-C_4$ alkyl substituted with $-NH_2$; $-NH_2$; $-NHMe$; $C_{1-6}$ alkoxy-$C_{1-6}$ alkyl optionally substituted with $-Si$ $(CH_3)_3$; $C_1-C_4$ hydroxyalkyl; $C_1-C_4$ haloalkyl; $C_1-C_4$ haloalkoxy; $C_1-C_4$ alkoxycarbonyl; $C_1-C_4$ alkylcarbonyloxy; $C_1-C_4$ alkylcarbonyl; $C_1-C_4$ alkylcarbonylamino; $-S(O)_mMe$; $-SO_2NH_2$; $-NHSO_2Me$; $-OCH_2CO_2R^{13}$; or 2-(1-morpholino)ethoxy;

$R^{12a}$, when a substituent on nitrogen, is selected from the following:

phenyl; benzyl; phenethyl; hydroxy; $C_1-C_4$ hydroxyalkyl; $C_1-C_4$ alkoxy; $C_1-C_4$ alkyl; $C_3-C_6$ cycloalkyl; $C_3-C_6$ cycloalkylmethyl; $C_1-C_4$ haloalkyl; $C_1-C_4$ alkoxycarbonyl; or $C_1-C_4$ alkylcarbonyl;

$R^{13}$ is selected from the following:

hydrogen;

phenyl substituted with 0–3 $R^{11a}$;

benzyl substituted with 0–3 $R^{11a}$;

$C_1-C_6$ alkyl substituted with 0–3 $R^{11a}$;

$C_2-C_4$ alkenyl substituted with 0–3 $R^{11a}$;

$C_1-C_6$ alkylcarbonyl substituted with 0–3 $R^{11a}$;

$C_1-C_6$ alkoxycarbonyl substituted with 0–3 $R^{11a}$;

$C_1-C_6$ alkylaminocarbonyl substituted with 0–3 $R^{11a}$;

$C_3-C_6$ alkoxyalkyl substituted with 0–3 $R^{11a}$;

an amine protecting group when $R^{13}$ is bonded to N;

a hydroxy protecting group when $R^{13}$ is bonded to O; or, a 5- to 10-membered heterocyclic ring system containing 1 to 3 heteroatoms independently selected from oxygen, nitrogen or sulfur, the heterocyclic ring system being substituted with 0–3 $R^{12a}$;

$R^{14}$ is selected from the following: hydrogen; hydroxy; $C_1-C_6$ alkoxy; $NH_2$; $-NH(C_1-C_4$ alkyl); $C_2-C_6$ alkenyl; phenyl; benzyl; an amine protecting group when $R^{14}$ is bonded to N; or $C_1-C_6$ alkyl substituted with 0–3 groups selected from OH, $C_1-C_4$ alkoxy, halogen, $NH_2$;

$R^{13}$ and $R^{14}$, when attached to the same N atom, can alternatively join to form: $-(CH_2)_4-$; $-(CH_2)_5-$;

—CH$_2$CH$_2$N(R$^{15}$)CH$_2$CH$_2$—; or
—CH$_2$CH$_2$OCH$_2$CH$_2$—;

R$^{15}$ is: hydrogen or methyl;

R$^{20}$ is selected from the following:

hydrogen;

C$_1$–C$_6$ alkyl substituted with 0–3 R$^{11}$;

C$_3$–C$_6$ alkoxyalkyl substituted with 0–3 R$^{11}$;

C$_1$–C$_6$ alkylcarbonyl substituted with 0–3 R$^{11}$;

C$_1$–C$_6$ alkoxycarbonyl substituted with 0–3 R$^{11}$;

C$_1$–C$_6$ alkylaminocarbonyl substituted with 0–3 R$^{11}$;

benzoyl substituted with 0–3 R$^{12}$;

phenoxycarbonyl substituted with 0–3 R$^{12}$;

phenylaminocarbonyl substituted with 0–3 R$^{12}$; or any group that, when administered to a mammalian subject, cleaves to form a free hydroxyl, amino or sulfhydryl;

m is 0, 1 or 2;

T is selected from:
—N(R$^{22}$)C(=Z)N(R$^{23}$)—;
—N(R$^{22}$)C(=Z)C(=Z)N(R$^{23}$)—;
—N(R$^{22}$)S(=Z')N(R$^{23}$)—;
—N(R$^{22}$)S(=Z')$_2$N(R$^{23}$)—; or
—N(R$^{22}$)P(=O)(R$^{24a}$)N(R$^{23}$)—;

Z is O, S, NR$^{24}$;

Z' is O or NR$^{24}$;

R$^{22}$ and R$^{23}$ are independently selected from the following:

hydrogen; OR$^{22a}$; —N(R$^{22a}$) (R$^{22b}$);

C$_1$–C$_8$ alkyl substituted with 0–3 R$^{31}$;

C$_2$–C$_8$ alkenyl substituted with 0–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$;

a 5- to 10-membered heterocyclic ring system containing 1 to 3 heteroatoms independently selected from oxygen, nitrogen or sulfur, said heterocyclic ring system being substituted with 0–2 R$^{32}$;

R$^{22a}$ and R$^{22b}$ are independently selected from the following:

hydrogen;

C$_1$–C$_8$ alkyl substituted with 0–3 R$^{31}$;

C$_2$–C$_8$ alkenyl substituted with 0–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$; or a 5- to 10-membered heterocyclic ring system containing 1 to 3 heteroatoms independently selected from oxygen, nitrogen or sulfur, said heterocyclic ring system being substituted with 0–2 R$^{32}$;

R$^{24}$ is independently:

hydrogen; hydroxy; amino; C$_1$–C$_4$ alkyl; C$_1$–C$_4$ alkoxy; mono-(C$_1$–C$_6$ alkyl)amino; di-(C$_1$–C$_6$ alkyl)amino; cyano; nitro; benzyloxy; or —NHSO$_2$aryl, aryl being optionally substituted with (C$_1$–C$_6$)alkyl;

R$^{24a}$ is selected from the following:

hydroxy; amino; C$_1$–C$_4$ alkyl; C$_1$–C$_4$ alkoxy; mono-(C$_1$–C$_6$ alkyl)amino; di-(C$_1$–C$_6$ alkyl)amino; benzyloxy; or phenoxy;

R$^{22}$ can alternatively join with R$^4$ or R$^{4a}$ to form a 5- or 6-membered fused heterocyclic ring or carbocyclic ring substituted with 0–2 R$^{12}$, said heterocyclic ring containing 1–3 heteroatoms independently selected from N, S, or O;

R$^{23}$ can alternatively join with R$^7$ or R$^{7a}$ to form a 5- or 6-membered fused heterocyclic ring or carbocyclic ring substituted with 0–2 R$^{12}$, said heterocyclic ring containing 1–3 heteroatoms independently selected from N, S, or O;

R$^{31}$ is selected from the following:

keto; halogen; cyano; —CH$_2$NR$^{13}$R$^{14}$; —NR$^{13}$R$^{14}$; —CO$_2$R$^{13}$; —C(=O)R$^{11}$; —OC(=O)R$^{13}$; —OR$^{13}$; C$_{1-6}$ alkoxy-C$_{1-6}$ alkyl; —S(O)$_m$R$^{13}$; —NHC(=NH)NHR$^{13}$; —C(=NH)NHR$^{13}$; —C(=O)NR$^{13}$R$^{14}$; —C(=NOR$^{11}$)NR$^{13}$R$^{14}$; —NR$^{14}$C(=O)R$^{13}$; NOR$^{14}$; —NR$^{14}$C(=O)OR$^{14}$; —OC(=O)NR$^{13}$R$^{14}$; —NR$^{13}$C(=S)NR$^{13}$R$^{14}$; —NR$^{14}$SO$_2$NR$^{13}$R$^{14}$; —NR$^{14}$SO$_2$R$^{13}$; —SO$_2$R$^{13}$; —SO$_2$NR$^{13}$R$^{14}$; C$_1$–C$_4$ alkyl; C$_2$–C$_4$ alkenyl; C$_3$–C$_{10}$ cycloalkyl; C$_3$–C$_6$ cycloalkylmethyl; phenyl; benzyl; phenethyl; phenoxy; benzyloxy; nitro; C$_7$–C$_{10}$ arylalkyl; hydroxamic acid; hydrazide; oxime; boronic acid; sulfonamide; formyl; C$_3$–C$_6$ cycloalkoxy; C$_1$–C$_4$ alkyl substituted with —NR$^{13}$R$^{14}$; C$_1$–C$_4$ hydroxyalkyl; methylenedioxy; ethylenedioxy; C$_1$–C$_4$ haloalkyl; C$_1$–C$_4$ haloalkoxy; —OCH$_2$CO$_2$R$^{13}$; 2-(1-morpholino)ethoxy; azido; —C(R$^{14}$)=N(OR$^{14}$);

1–3 amino acids, linked together via amide bonds, said amino acid being linked via the amine or carboxylate terminus;

a C$_5$–C$_{14}$ carbocyclic residue substituted with 0–5 R$^{32}$; or a 5- to 10-membered heterocyclic ring system containing 1 to 3 heteroatoms independently selected from oxygen, nitrogen or sulfur, said heterocyclic ring system being substituted with 0–2 R$^{12}$;

R$^{32}$, when a substituent on carbon, is independently:

phenyl; phenethyl; phenoxy; C$_3$–C$_{10}$ cycloalkyl; C$_3$–C$_6$ cycloalkylmethyl; C$_7$–C$_{10}$ arylalkyl; hydrazide; hydroxamic acid; boronic acid; oxime; C$_{1-6}$ alkoxy-C$_{1-6}$ alkyl; methylenedioxy; ethylenedioxy; C$_1$–C$_4$ alkylcarbonyloxy; —NHSO$_2$R$^{14}$; phenylmethoxy; halogen; 2-(1-morpholino)ethoxy; —CO$_2$R$^{13}$; —CONR$^{13}$NR$^{13}$R$^{14}$; cyano; —CHO; C$_3$–C$_6$ cycloalkoxy; —NR$^{13}$R$^{14}$; —C(R$^{14}$)=N(OR$^{14}$); NO$_2$; —OR$^{13}$; —NR$^{40}$R$^{41}$; —SO$_m$R$^{13}$; —SO$_m$NR$^{13}$R$^{14}$; NR$^{14}$(C=O)R$^{11}$; —C(=O)NR$^{11}$R$^{14}$; —C(=O)NR$^{13}$R$^{14}$; —OC(=O)NR$^{13}$R$^{14}$; —C(=O)R$^{11}$; —OC(=O)R$^{11}$; —OCO$_2$R$^{13}$; phenyl; —C(=O)NR$^{13}$-(C$_1$–C$_4$ alkyl)-NR$^{13}$R$^{14}$; —C(=O)NR$^{40}$R$^{41}$; C$_1$–C$_4$ haloalkyl; C$_1$–C$_4$ haloalkoxy; C$_2$–C$_4$ haloalkenyl; C$_1$–C$_4$ haloalkynyl; —C(=O)NR$^{13}$C(R$^{11}$)$_2$NR$^{13}$R$^{14}$; —C(=O)NR$^{13}$C(R$^{11}$)$_2$NR$^{13}$NR$^{14}$; —C(=C)) NR$^{13}$C(R$^{11}$)$_2$NR$^{13}$CO$_2$R$^{13}$; —C(=O) NR$^{13}$-(C$_1$–C$_4$ alkyl)-NR$^{13}$CO$_2$R$^{13}$; —C(=O)N(R$^{13}$)—(C$_1$–C$_4$ alkyl)-R$^{11}$; —C(=O)C(R$^{11}$)$_2$NR$^{13}$R$^{14}$; —C(=O)C(R$^{11}$)$_2$NR$^{13}$NR$^{14}$; —C(=O)C(R$^{11}$)$_2$NR$^{13}$CO$_2$R$^{13}$; —C(=O)-(C$_1$–C$_4$ alkyl)-NR$^{13}$R$^{14}$; —C(=O)—(C$_1$–C$_4$ alkyl)-NR$^{13}$CO$_2$R$^{13}$;

C$_1$–C$_4$ alkoxy substituted with 0–4 groups selected from: R$^{11}$, C$_3$–C$_6$ cycloalkyl, —CO$_2$R$^{13}$, —C(=O)NR$^{13}$R$^{14}$, —NR$^{13}$R$^{14}$ or OH; C$_1$–C$_4$ alkyl substituted with 0–4 groups selected from: R$^{11}$, =NR$^{14}$, —NNR$^{13}$C(=O)NR$^{13}$R$^{14}$ =NNR$^{13}$C(=O)OR$^{13}$, or —NR$^{13}$R$^{14}$; C$_2$–C$_4$ alkenyl substituted with 0–4 R$^{11}$; C$_2$–C$_4$ alkynyl substituted with 0–4 R$^{11}$;

a 5- to 10-membered heterocyclic ring containing from 1 to 3 heteroatoms independently selected from oxygen, nitrogen or sulfur, said heterocyclic ring being substituted with 0–2 R$^{12}$; and, a 3- or 4- carbon chain, wherein 0, 1 or 2 of the carbon atoms are replaced with a heteroatom independently selected from oxygen, nitrogen or sulfur, attached to an adjacent carbon on the ring to which it is appended to form a fused 5- or 6-membered ring, said 5- or 6- membered ring being substituted on the aliphatic carbons with 0–3 halogen, C$_1$–C$_4$ alkyl, C$_1$–C$_4$ alkoxy, hydroxy, —NR$^{13}$R$^{14}$;

when R$^{32}$ is attached to a saturated carbon atom, it may be =O =S or =NOH; or when R$^{32}$ is attached to sulfur it may be =O;

$R^{32}$, when a substituent on nitrogen, is independently: phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —$CH_2NR^{13}R^{14}$; —$NR^{13}R^{14}$; $C_{1-6}$ alkoxy-$C_{1-6}$ alkyl; $C_1$–$C_4$ haloalkyl; $C_1$–$C_4$ alkoxycarbonyl; —$CO_2H$; $C_1$–$C_4$ alkylcarbonyloxy; $C_1$–$C_4$ alkylcarbonyl; —$C(R^{14})$=$N(OR^{14})$;

$R^{40}$ is hydrogen or $C_1$–$C_3$ alkyl;

$R^{41}$ is selected from —$C(=O)NR^{13}R^{14}$; —$C(=O)NR^{13}NR^{13}R^{14}$; —$C(=O)C(R^{11})_2NR^{13}R^{14}$; —$C(=O)C(R^{11})_2NR^{13}NR^{13}R^{14}$; —$C(=O)C(R^{11})_2NR^{13}CO_2R^{13}$; —$C(=O)H$; —$C(=O)R^{11}$; —$C(=O)$-($C_1$–$C_4$ alkyl)-$NR^{13}R^{14}$; —$C(=O)$-($C_1$–$C_4$ alkyl)-$NR^{13}CO_2R^{13}$; or 1–3 amino acids linked together via amide bonds, and linked to the N atom via the carboxylate terminus;

provided that $R^4$, $R^{4a}$, $R^7$ and $R^{7a}$ are not all hydrogen and when $R^4$, $R^{4a}$ are hydrogen, then $R^{22}$ is not hydrogen; are effective retroviral protease inhibitors.

DETAILED DESCRIPTION OF PREFERRED EMBODIMENTS

Thus, in a first embodiment, the present invention provides novel compounds of formula I:

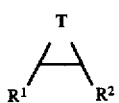

(I)

or pharmaceutically acceptable salt or prodrug forms thereof, wherein T, $R^1$, and $R^2$ are as defined above.

[1] In a preferred embodiment, the present invention provides novel compounds of formula (II):

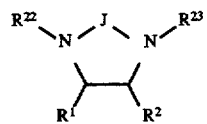

(II)

or pharmaceutically acceptable salt or prodrug forms thereof, wherein;

J is —$C(=Z)$—, or —$P(=O)$ ($R^{24a}$)—;

Z is O, or $NR^{24}$;

$R^1$ is —$C(R^4)$ ($R^{4a}$)$R^5$;

$R^2$ is —$C(R^7)$ ($R^{7a}$)$R^6$;

$R^1$ and $R^2$ may, together, be —$C(H)$ ($R^4$)$C(H)$ ($R^5$)$C(H)$ ($R^6$)$C(H)(R^7)$—;

when $R^1$ and $R^2$, together, are —$C(H)$ ($R^4$)$C(H)(R^5)C(H)$ ($R^6$)$C(H)(R^7)$—, J may also be $S(O)_m$;

m is 0, 1 or 2;

when J=$S(O)_m$:

$R^{22}$ and $R^{23}$ may, independently, also be $C_{1-6}$ alkyl; $R^{31}$ may also be $OR^{13}$ or a $C_{5-7}$ carbocyclic residue; and $R^{32}$ may also be ($C_{1-4}$ alkyl substituted with 1–2 —$OR^{13}$;

$R^4$ and $R^7$ are independently selected from the following: hydrogen; —$CO_2R^{13}$; —$NR^{11}R^{13}$;

$C_1$–$C_8$ alkyl substituted with 0–3 $R^{11}$;

$C_2$–$C_8$ alkenyl substituted with 0–3 $R^{11}$;

$C_2$–$C_8$ alkynyl substituted with 0–3 $R^{11}$;

a $C_3$–$C_{14}$ carbocyclic ring system substituted with 0–3 $R^{11}$ or $R^{12}$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{4a}$ and $R^{7a}$ are independently selected from the following:

hydrogen; $C_{02}R^{13}$;

$C_1$–$C_4$ alkyl unsubstituted or substituted with halogen or $C_1$–$C_2$ alkoxy; or benzyl unsubstituted or substituted with halogen or $C_1$–$C_2$ alkoxy;

$R^5$ and $R^6$ are independently selected from the following: hydrogen, halogen, —$N(R^{20})_2$, —$SR^{20}$, —$OR^{20}$, or $C_1$–$C_6$ alkyl substituted with 0–3 $R^{11}$;

$R^5$ and $R^6$ can alternatively join to form —$OCH_2SCH_2O$—, —$OS(=O)O$—, —$OC(=O)O$—, —$OCH_2O$—, —$OC(=S)O$—, —$OC(=O)C(=O)O$—, —$OC(CH_3)_2O$—, —$OC((CH_2)_3NH_2)(CH_3)O$—, —$OCH_2OCH_2O$—, —$OC(OCH_3)(CH_2CH_2CH_3)O$—, —$NHC(=O)NH$—, —$OC(=O)NH$—, —$NHC(=O)O$—, —$NHCH_2O$—, —$OCH_2NH$—, —$NHC(=S)O$—, —$OS(=O)NH$—, —$NHC(=O)C(=O)O$—, —$OC(=O)C(=O)NH$—, —$NHC(=O)C(=O)NH$—, —$NHC(CH_3)_2O$—, —$OC(CH_3)_2NH$— or any group that, when administered to a mammalian subject, cleaves to form a free dihydroxyl or diamino or hydroxyl and amino;

$R^5$ and $R^{4a}$ can alternatively join to form =O, =S, or a ketal ring;

$R^6$ and $R^{7a}$ can alternatively join to form =O, =S, or a ketal ring;

$R^{11}$ is selected from the following:

hydrogen; keto; halogen; cyano; —$CH_2NR^{13}R^{14}$; —$NR^{13}R^{14}$; —$CO_2R^{13}$; —$OC(=O)R^{13}$; —$OR^{13}$; —$S(O)_mR^{13}$; —$C(=O)$ $NR^{13}R^{14}$; —$SO_2NR^{13}R^{14}$; $C_2$–$C_4$ alkenyl; $C_3$–$C_6$ cycloalkylmethyl; nitro; $C_7$–$C_{10}$ arylalkyl; formyl; $C_3$–$C_6$ cycloalkoxy; methylenedioxy; ethylenedioxy; $C_1$–$C_4$ haloalkyl; $C_1$–$C_4$ haloalkoxy; pyridylcarbonyloxy; $C_1$–$C_4$ alkylcarbonyl;

$C_3$–$C_{10}$ cycloalkyl substituted with 0–2 $R^{12}$;

$C_1$–$C_4$ alkyl substituted with 0–2 $R^{12}$;

aryl-$C_1$–$C_3$ alkyl substituted with 0–2 $R^{12}$;

$C_{2-6}$ alkoxy-$C_{2-6}$ alkyl substituted with 0–2 $R^{12}$;

a $C_5$–$C_{14}$ carbocyclic residue substituted with 0–3 $R^{12}$;

a 5- to 10-membered heterocyclic ring system containing 1 to 3 heteroatoms independently selected from oxygen, nitrogen or sulfur, said heterocyclic ring system being substituted with 0–3 $R^{12}$;

$R^{11a}$ is selected from the following:

halogen; cyano; —$NH_2$; —$NH(C_1$–$C_3$ alkyl); —$CO_2H$; —$OC(=O)(C_1$–$C_3$ alkyl); —$OH$; $C_{1-6}$ alkoxy-$C_{1-6}$ alkyl; —$C(=O)NH_2$; —$SO_2NH_2$; $C_3$–$C_{10}$ cycloalkyl; $C_3$–$C_6$ cycloalkylmethyl; phenoxy; benzyloxy; nitro;

$C_3$–$C_6$ cycloalkoxy; $C_1$–$C_4$ alkyl substituted with —$NH_2$; $C_1$–$C_4$ hydroxyalkyl; methylenedioxy; ethylenedioxy; $C_1$–$C_4$ haloalkyl; $C_1$–$C_4$ haloalkoxy; $C_1$–$C_4$ alkoxycarbonyl; $C_1$–$C_4$ alkylcarbonyl; $C_1$–$C_4$ alkylcarbonylamino; 2-(1-morpholino)ethoxy; aryl-$C_1$–$C_3$ alkyl; a $C_5$–$C_{14}$ carbocyclic residue; a 5- to 10-membered heterocyclic ring system containing 1 to 3 heteroatoms independently selected from oxygen, nitrogen or sulfur, said heterocyclic ring system substituted with 0–3 $R^{12a}$;

$R^{12}$ when a substituent or carbon, is selected from the following:

phenyl; halogen; hydroxy; nitro; cyano; $C_1$–$C_4$ alkyl substituted with 0–2 $OR^{13}$, $SR^{13}$, or $NR^{11}R^{13}$; $C_3$–$C_6$ cycloalkyl; $C_3$–$C_6$ cycloalkylmethyl; $C_7$–$C_{10}$ arylalkyl; $C_1$–$C_4$ alkoxy; —$CO_2H$; hydroxamic acid; hydrazide;

boronic acid; sulfonamide; formyl; $C_3$–$C_6$ cycloalkoxy; —$OR^{13}$; —$NR^{13}R^{14}$; $C_1$–$C_4$ alkyl substituted with —$NR^{13}R^{14}$; $C_{1-6}$ alkoxy $C_{1-6}$ alkyl substituted with 0 or 1 —$Si(CH_3)_3$; $C_1$–$C_4$ hydroxyalkyl; methylenedioxy; ethylenedioxy; $C_1$–$C_4$ haloalkyl; $C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; —$S(O)_mR^{13}$; —$SO_2NR^{13}R^{14}$; —$NHSO_2R^{14}$; —$OCH_2CO_2R^{13}$; 2-(1-morpholino)ethoxy; —$C(R^{14})=N(OR^{13})$;

a 5- or 6-membered heterocyclic ring containing from 1 to 3 heteroatoms independently selected from oxygen, nitrogen or sulfur, the heterocyclic ring system being substituted with 0–3 $R^{12a}$;

a 3- or 4- carbon chain attached to adjacent carbons on the ring to which it is appended to form a fused 5- or 6-membered ring, said 5- or 6- membered ring being optionally substituted on any of the aliphatic carbons with halogen, $C_1$–$C_4$ alkyl, $C_1$–$C_4$ alkoxy, hydroxy, —$NR^{13}R^{14}$; and when $R^{12}$ is attached to a saturated carbon atom, it may be =O or =S, or when $R^{12}$ is attached to sulfur it may be =O;

$R^{12}$, when a substituent on nitrogen, is selected from the following:

phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —$CH_2NR^{13}R^{14}$; —$NR^{13}R^{14}$; $C_{1-6}$ alkoxy-$C_{1-6}$ alkyl; $C_1$–$C_4$ haloalkyl; $C_1$–$C_4$ alkoxycarbonyl; —$CO_2H$; $C_1$–$C_4$ alkylcarbonyloxy; $C_1$–$C_4$ alkylcarbonyl;

$R^{12a}$, when a substituent on carbon, is selected from the following:

phenyl; benzyl; phenethyl; phenoxy; benzyloxy; halogen; hydroxy; nitro; cyano; $C_1$–$C_4$ alkyl; $C_3$–$C_6$ cycloalkyl; $C_3$–$C_6$ cycloalkylmethyl; $C_7$–$C_{10}$ arylalkyl; $C_1$–$C_4$ alkoxy; —$CO_2H$; formyl; $C_3$–$C_6$ cycloalkoxy; —$OH^{13}$; $C_1$–$C_4$ alkyl substituted with —$NH_2$ or —$NHMe$; $C_{1-6}$ alkoxy-$C_{1-6}$ alkyl optionally substituted with —$Si(CH_3)_3$; $C_1$–$C_4$ hydroxyalkyl; $C_1$–$C_4$ haloalkyl; $C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; —$S(O)_mMe$; —$SO_2NH_2$; —$NHSO_2Me$; —$OCH_2CO_2R^{13}$; and 2-(1-morpholino)ethoxy;

$R^{12a}$, when a substituent on nitrogen, is selected from the following:

phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; $C_1$–$C_4$ haloalkyl; $C_1$–$C_4$ alkoxycarbonyl; and $C_1$–$C_4$ alkylcarbonyl;

$R^{13}$ is selected from the following:
hydrogen;
phenyl substituted with 0–3 $R^{11a}$;
benzyl substituted with 0–3 $R^{11a}$;
$C_1$–$C_6$ alkyl substituted with 0–3 $R^{11a}$;
$C_2$–$C_4$ alkenyl substituted with 0–3 $R^{11a}$;
$C_1$–$C_6$ alkylcarbonyl substituted with 0–3 $R^{11a}$;
$C_1$–$C_6$ alkoxycarbonyl substituted with 0–3 $R^{11a}$;
$C_1$–$C_6$ alkylaminocarbonyl substituted with 0–3 $R^{11a}$;
$C_3$–$C_6$ alkoxyalkyl substituted with 0–3 $R^{11a}$;
an amine protecting group when $R^{13}$ is bonded to N;
a hydroxy protecting group when $R^{13}$ is bonded to O; and,
a 5- to 10-membered heterocyclic ring system containing 1 to 3 heteroatoms independently selected from oxygen, nitrogen or sulfur, the heterocyclic ring system being substituted with 0–3 $R^{12a}$;

$R^{14}$ is selected from: hydrogen; hydroxy; $C_1$–$C_6$ alkoxy; $NH_2$; —$NH(C_1$–$C_4$ alkyl); $C_2$–$C_6$ alkenyl; phenyl; benzyl; an amine protecting group when $R^{14}$ is bonded to N; or $C_1$–$C_6$ alkyl substituted with 0–3 groups selected from OH, $C_1$–$C_4$ alkoxy, halogen, $NH_2$;

$R^{13}$ and $R^{14}$, when attached to the same N atom, can alternatively join to form: —$(CH_2)_4$—; —$(CH_2)_5$—; —$CH_2CH_2N(R^{15})CH_2CH_2$—; or —$CH_2CH_2OCH_2CH_2$—;

$R^{15}$ is: hydrogen or methyl;

$R^{20}$ is selected from:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; and
any group that, when administered to a mammalian subject, cleaves to form a free hydroxyl, amino or sulfhydryl;

$R^{22}$ and $R^{23}$ are independently selected from the following:
—$OR^{22a}$; —$N(R^{22a})(R^{22b})$;
$C_1$–$C_8$ alkyl substituted with 1–3 $R^{31}$;
$C_2$–$C_8$ alkenyl substituted with 1–3 $R^{31}$;
$C_2$–$C_8$ alkynyl substituted with 0–3 $R^{31}$;
a $C_3$–$Cl_4$ carbocyclic ring system substituted with 1–5 $R^{31}$;
a 5- to 10-membered heterocyclic ring system containing 1 to 3 heteroatoms independently selected from oxygen, nitrogen or sulfur, said heterocyclic ring system being substituted with 0–2 $R^{32}$;

$R^{22}$ and $R^{23}$ can independently be unsubstituted $C_{2-8}$ alkenyl when either $R^5$ or $R^6$ or both are halogen;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$Cl4$ carbocyclic ring system substituted with 0–5 $R^{31}$ or $R^{32}$; and
a 5- to 10-membered heterocyclic ring system containing 1 to 3 heteroatoms independently selected from oxygen, nitrogen or sulfur, said heterocyclic ring system being substituted with 0–2 $R^{32}$;

$R^{24}$ is selected from: hydrogen; hydroxy; amino; $C_1$–$C_4$ alkyl; $C_1$–$C_4$ alkoxy; mono-($C_1$–$C_6$ alkyl)amino; di-($C_1$–$C_6$ alkyl)amino; cyano; nitro; benzyloxy; or —$NHSO_2$aryl, aryl being substituted with 0–1 ($C_1$–$C_6$) alkyl;

$R^{24a}$ is selected from: hydroxy; amino; $C_1$–$C_4$ alkyl; $C_1$–$C_4$ alkoxy; mono-($C_1$–$C_6$ alkyl)amino; di-($C_1$–$C_6$ alkyl)amino; benzyloxy; or phenoxy;

$R^{31}$ is selected from: halogen; cyano; —$NR^{33}R^{14}$; $C_1$–$C_4$ alkyl substituted with —$NR^{33}R^{14}$; —$CO_2R^{13}$; —$C(=O)R^{33}$; —$OC(=O)R^{33}$; —$OR^{33}$; —$S(O)_mR^{13}$; —$NHC(=NH)NHR^{13}$; —$C(=NH)NHR^{13}$; —$C(=O)NR^{13}R^{14}$; —$C(=NOR^{11})NR^{13}R^{14}$; —$NR^{14}C(=O)R^{13}$; =$NOR^{14}$; —$NR^{14}C(=O)OR^{14}$; —$OC(=O)NR^{13}R^{14}$; —$NR^{13}C(=S)NR^{13}R^{14}$; —$NR^{14}SO_2NR^{13}R^{14}$; —$NR^{14}SO_2R^{13}$; —$SO_2NR^{13}R^{14}$; $C_3$–$C_{10}$ cycloalkyl; phenoxy; benzyloxy; nitro; hydroxamic acid; hydrazide; oxime; boronic acid; sulfonamide; formyl; $C_3$–$C_6$ cycloalkoxy; methylenedioxy; ethylenedioxy, $C_1$–$C_4$ haloalkyl; $C_1$–$C_4$ haloalkoxy; —$OCH_2CO_2R^{13}$; 2-(1-morpholino)

ethoxy; azido; —C($R^{14}$)=N(O$R^{14}$); 1-3 amino acids, linked together via amide bonds, said amino acid being linked via the amine or carboxylate terminus; a $C_5$–$C_{14}$ carbocyclic residue substituted with 1–5 $R^{32}$; and, a 5- to 10-membered heterocyclic ring system containing 1 to 3 heteroatoms independently selected from oxygen, nitrogen or sulfur, said heterocyclic ring system being substituted with 0–2 R12;

$R^{32}$, when a substituent on carbon, is selected from:
phenyl; phenethyl; phenoxy; $C_3$–$C_{10}$ cycloalkyl; $C_3$–$C_6$ cycloalkylmethyl; $C_7$–$C_{10}$ arylalkyl; hydrazide; hydroxamic acid; boronic acid; oxime; $C_{1-6}$ alkoxy-$C_{1-6}$ alkyl; methylenedioxy; ethylenedioxy; $C_1$–$C_4$ alkylcarbonyloxy; —NHSO$_2R^{14}$; phenylmethoxy; halogen; 2-(1-morpholino)ethoxy; —CO$_2R^{13}$; —CONR$^{13}$NR$^{13}R^{14}$; cyano, —CHO; $C_3$–$C_6$ cycloalkoxy; —NR$^{13}R^{14}$; —C($R^{14}$)=N(O$R^{14}$); NO$_2$; —O$R^{13}$; —NR$^{40}R^{41}$; —SO$_mR^{13}$; —SO$_m$NR$^{13}R^{14}$; —NR$^{14}$ (C=O) $R^{11}$; —C(=O) NR$^{11}R^{14}$; —C(=O) NR$^{13}R^{14}$; —OC(=O) NR$^{13}R^{14}$; —C(=O)$R^{11}$; —OC(=O)$R^{11}$; —OCO$_2R^{13}$; phenyl; —C(=O)NR$^{13}$-($C_1$–$C_4$ alkyl)-NR$^{13}R^{14}$; —C(=O)NR$^{40}R^{41}$; $C_1$–$C_4$ haloalkyl; $C_1$–$C_4$ haloalkoxy; $C_2$–$C_4$ haloalkenyl; $C_1$–$C_4$ haloalkynyl; —C(=O)NR$^{13}$C($R^{11}$)$_2$NR$^{13}R^{14}$;

—C(=O)NR$^{13}$C($R^{11}$)$_2$NR$^{13}$NR$^{14}$; —C(=O)NR$^{13}$C($R^{11}$)$_2$NR$^{13}$CO$_2R^{13}$;

—C(=O)NR$^{13}$-($C_1$–$C_4$ alkyl)-NR$^{13}$CO$_2R^{13}$; —C(=O)N($R^{13}$)-($C_1$–$C_4$ alkyl)-$R^{11}$; —C(=O)C($R^{11}$)$_2$NR$^{13}R^{14}$; —C(=O)C($R^{11}$)$_2$NR$^{13}$NR$^{14}$; —C(=O)C($R^{11}$)$_2$NR$^{13}$CO$_2R^{13}$; —C(=O)-($C_1$–$C_4$ alkyl)-NR$^{13}R^{14}$; —C(=O)—($C_1$–$C_4$ alkyl)-NR$^{13}$CO$_2R^{13}$;

$C_1$–$C_4$ alkoxy substituted with 1–4 groups selected from: $R^{11}$,
$C_3$–$C_6$ cycloalkyl, —CO$_2R^{13}$, —C(=O)NR$^{13}R^{14}$, —NR$^{13}R^{14}$ or OH;

$C_1$–$C_4$ alkyl substituted with 1–4 groups selected from: $R^{11}$, =N$R^{14}$, =NNR$^{13}$C(=O)NR$^{13}R^{14}$ =NNR$^{13}$C(=O)O$R^{13}$, or —NR$^{13}R^{14}$;

$C_2$–$C_4$ alkenyl substituted with 1–4 $R^{11}$;
$C_2$–$C_4$ alkynyl substituted with 1–4 $R^{11}$;
a 5- to 10-membered heterocyclic ring containing from 1 to 3 heteroatoms independently selected from oxygen, nitrogen or sulfur, said heterocyclic ring being substituted with 0–2 $R^{12}$;
a 3- or 4- carbon chain wherein 0, 1 or 2 of the carbon atoms are replaced with a heteroatom independently selected from oxygen, nitrogen or sulfur, attached to an adjacent carbon on the ring to which it is appended to form a fused 5- or 6-membered ring, said 5- or 6- membered ring being optionally substituted on the aliphatic carbons with 0–3 halogen, $C_1$–$C_4$ alkyl, $C_1$–$C_4$ alkoxy, hydroxy, —NR$^{13}R^{14}$; or, when $R^{32}$ is attached to a saturated carbon atom, it may be =O =S or =NOH; or when $R^{32}$ is attached to sulfur it may be =O;

$R^{32}$, when a substituent on nitrogen, is selected from:
phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —CH$_2$NR$^{13}R^{14}$; —NR$^{13}R^{14}$; $C_{1-6}$ alkoxy-$C_{1-6}$ alkyl; $C_1$–$C_4$ haloalkyl; $C_1$–$C_4$ alkoxycarbonyl; —CO$_2$H; $C_1$–$C_4$ alkylcarbonyloxy; $C_1$–$C_4$ alkylcarbonyl; —C($R^{14}$)=N(O$R^{14}$);

$R^{33}$ is selected from the following:
phenyl substituted with 0–3 $R^{11a}$;
benzyl substituted with 0–3 $R^{11a}$;
$C_1$–$C_6$ alkyl substituted with 1–3 $R^{11a}$;
$C_2$–$C_4$ alkenyl substituted with 1–3 $R^{11a}$;
$C_1$–$C_6$ alkylcarbonyl substituted with 1–3 $R^{11a}$;

$C_1$–$C_6$ alkoxycarbonyl substituted with 0–3 $R^{11a}$;
$C_1$–$C_6$ alkylaminocarbonyl substituted with 0–3 $R^{11a}$;
$C_3$–$C_6$ alkoxyalkyl substituted with 0–3 $R^{11a}$;
an amine protecting group when. $R^{13}$ is bonded to N;
a hydroxy protecting group when $R^{13}$ is bonded to O; or,
a 5- to 10-membered heterocyclic ring system containing 1 to 3 heteroatoms independently selected from oxygen, nitrogen or sulfur, the heterocyclic ring system being substituted with 0–3 $R^{12}$;

$R^{40}$ is hydrogen or $C_1$–$C_3$ alkyl;

$R^{41}$ is selected from —C(=O)NR$^{13}R^{14}$; —C(=O) NR$^{13}$NR$^{13}R^{14}$; —C(=O)C($R^{11}$)$_2$NR$^{13}R^{14}$; —C(=O) C($R^{11}$)$_2$NR$^{13}$NR$^{13}R^{14}$; —C(=O)C($R^{11}$)$_2$ NR$^{13}$CO$_2R^{13}$; —C(=O)H; —C(=O)$R^{11}$; —C(=O)-($C_1$–$C_4$ alkyl)-NR$^{13}R^{14}$; —C(=O)-($C_1$–$C_4$ alkyl)-NR$^{13}$CO$_2R^{13}$; or 1–3 amino acids linked together via amide bonds, and linked to the N atom via the carboxylate terminus;

provided that:
1) $R^4$, $R^{4a}$, $R^7$ and $R^{7a}$ are not all hydrogen; and
2) $R^1$ does not represent unsubstituted straight or branched alkyl.

[2] In a more preferred embodiment, the present invention provides novel compounds of formula (IIa):

$$\underset{R^5 \quad R^6}{\overset{R^{22} \diagdown_{N} \diagup^{J} \diagdown_{N} \diagup^{R^{23}}}{\underset{R^4 \diagup \diagdown R^7}{}}} \quad (IIa)$$

or pharmaceutically acceptable salt or prodrug forms thereof, wherein;

J is C=O or C=S;

$R^4$ and $R^7$ are independently selected from the following:
hydrogen; —CO$_2R^{13}$; —NR$^{11}R^{13}$;
$C_1$–$C_6$ alkyl substituted with 0–3 $R^{11}$;
$C_2$–$C_6$ alkenyl substituted with 0–3 $R^{11}$;
$C_2$–$C_6$ alkynyl substituted with 0–3 $R^{11}$; or
a $C_5$–$C_{10}$ carbocyclic ring system substituted with 0–3 $R^{11}$ or $R^{12}$;

$R^5$ and $R^6$ are independently selected from the following:
hydrogen, halogen, —N($R^{20}$)$_2$—S$R^{20}$, —O$R^{20}$, =O, or $C_1$–$C_6$ alkyl substituted with 0–3 $R^{11}$;

$R^5$ and $R^6$ can alternatively join to form —OCH$_2$SCH$_2$O—, —OS(=O)O—, —OC(=O)O—, —OCH$_2$O—, —OC(=S)O—, —OC(=O)C(=O) O—, —OC(CH$_3$)$_2$O—, —OC((CH$_2$)$_3$NH$_2$)(CH$_3$)O—, —OCH$_2$OCH$_2$O—, —OC(OCH$_3$)(CH$_2$CH$_2$CH$_3$)O—, —NHC(=O)NH—, —OC(=O)NH—, —NHC(=O)O—, —NHCH$_2$O—, —OCH$_2$NH—, —NHC(=S)O—, —OS(=O)NH—, —NHC(=O)C(=O)O—, —OC(=O)C(=O)NH—, —NHC(=O)C(=O)NH—, —NHC(CH$_3$)$_2$O—, —OC(CH$_3$)$_2$NH—or any group that, when administered to a mammalian subject, cleaves to form a free dihydroxyl or diamino or hydroxyl and amino;

$R^{11}$ is selected from the following: hydrogen; keto; halogen; cyano; —NR$^{13}R^{14}$; —CO$_2R^{13}$; —OC(=O) $R^{13}$; —O$R^{13}$; —S(O)$_mR^{13}$; —C(=O)NR$^{13}R^{14}$; —SO$_2$NR$^{13}R^{14}$; $C_2$–$C_4$ alkenyl; nitro; formyl; $C_1$–$C_4$ haloalkyl; $C_1$–$C_4$ haloalkoxy; $C_1$–$C_4$ alkyl substituted with 0–2 $R^{12}$;
$C_{2-6}$ alkoxy-$C_{2-6}$ alkyl substituted with 0–2 $R^{12}$;
a $C_5$–$C_{10}$ carbocyclic residue substituted with 0–3 $R^{12}$;

a 5- to 10-membered heterocyclic ring system containing 1 to 3 heteroatoms independently selected from oxygen, nitrogen or sulfur, said heterocyclic ring system being substituted with 0–3 R12;

$R^{11a}$ is selected from the following: halogen; cyano; —$NH_2$; —$NH(C_1$–$C_3$ alkyl); —$CO_2H$; —OC(=O) ($C_1$–$C_3$ alkyl); —OH; —C(=O)$NH_2$; —$SO_2NH_2$; $C_3$–$C_6$ cycloalkyl; $C_3$–$C_6$ cycloalkylmethyl; phenoxy; benzyloxy; nitro; $C_3$–$C_6$ cycloalkoxy; $C_1$–$C_4$ alkyl substituted with —$NH_2$; $C_1$–$C_4$ hydroxyalkyl; $C_1$–$C_4$ haloalkyl; $C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; 2-(1-morpholino)ethoxy;

$R^{12}$, when a substituent on carbon, is selected from the following:

phenyl; halogen; hydroxy; nitro; cyano; $C_1$–$C_4$ alkyl substituted with 0–2 $OR^{13}$, $SR^{13}$, or $NR^{11}R^{13}$; $C_3$–$C_6$ cycloalkylmethyl; $C_1$–$C_4$ alkoxy; —$CO_2H$; hydroxamic acid; hydrazide; boronic acid; sulfonamide; formyl; $C_3$–$C_6$ cycloalkoxy; —$OR^{13}$; —$NR^{13}R^{14}$; $C_1$–$C_4$ alkyl substituted with —$NR^{13}R^{14}$; $C_{1-6}$ alkoxy $C_{1-6}$ alkyl; $C_1$–$C_4$ hydroxyalkyl; $C_1$–$C_4$ haloalkyl; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; —$S(O)_mR^{13}$; —$SO_2NR^{13}R^{14}$; —$NHSO_2R^{14}$; —$OCH_2CO_2R^{13}$; —$C(R^{14})$=$N(OR^{13})$;

$R^{12}$, when a substituent on nitrogen, is selected from the following:

phenyl; benzyl; phenethyl; hydroxy; $C_1$–$C_4$ hydroxyalkyl; $C_1$–$C_4$ alkyl; $C_3$–$C_6$ cycloalkyl; $C_3$–$C_6$ cycloalkylmethyl; —$CH_2NR^{13}R^{14}$; $C_{1-6}$ alkoxy-$C_{1-6}$ alkyl; $C_1$–$C_4$ haloalkyl; $C_1$–$C_4$ alkoxycarbonyl; $C_1$–$C_4$ alkylcarbonyl;

$R^{13}$ is selected from the following:
hydrogen;
phenyl substituted with 0–3 $R^{11a}$;
benzyl substituted with 0–3 $R^{11a}$;
$C_{1-4}$ alkyl substituted with 0–3 $R^{11a}$;
$C_{2-4}$ alkenyl substituted with 0–3 $R^{11a}$;
an amine protecting group when $R^{13}$ is bonded to N; or a hydroxy protecting group when $R^{13}$ is bonded to O;

$R^{14}$ is selected from the following: hydrogen; $C_{2-4}$ alkenyl; phenyl; benzyl; an amine protecting group when $R^{14}$ is bonded to N; or $C_{1-4}$ alkyl substituted with 0–3 groups selected from OH, $C_1$–$C_4$ alkoxy, halogen;

$R^{13}$ and $R^{14}$, when attached to the same N atom, can alternatively join to form: —$(CH_2)_4$— or —$(CH_2)_5$—;

$R^{20}$ is selected from the following:
hydrogen;
$C_{1-4}$ alkyl substituted with 0–3 $R^{11}$;
$C_{1-5}$ alkoxycarbonyl substituted with 0–3 $R^{11}$;
benzoyl substituted with 0–3 $R^{12}$; or any group that, when administered to a mammalian subject, cleaves to form a free hydroxyl, amino or sulfhydryl;

$R^{22}$ and $R^{23}$ are independently selected from the following:
$C_{1-8}$ alkyl substituted with 1–3 $R^{31}$;
$C_{2-6}$ alkenyl substituted with 1–3 $R^{31}$;
$C_{2-4}$ alkynyl substituted with 0–3 $R^{31}$;
a $C_{3-10}$ carbocyclic ring system substituted with 1–5 $R^{31}$; and,
a 5- to 10-membered heterocyclic ring system containing 1 to 3 heteroatoms independently selected from oxygen, nitrogen or sulfur, said heterocyclic ring system being substituted with 0–2 $R^{32}$;

$R^{22}$ and $R^{23}$ can independently be unsubstituted $C_{2-8}$ alkenyl when either $R^5$ or $R^6$ or both are halogen;

$R^{31}$ is selected from the following: halogen; cyano; —$CH_2NR^{33}R^{14}$; —$NR^{33}R^{14}$; —$CO_2R^{13}$; —C(=O)$R^{33}$; —OC(=O)$R^{33}$; —$OR^{33}$; —C(=O)$NR^{13}R^{14}$; $C_3$–$C_{10}$ cycloalkyl; nitro; formyl; $C_{1-4}$ haloalkyl; $C_{1-4}$ haloalkoxy; —$OCH_2CO_2R^{13}$; 2-(1-morpholino)ethoxy; a $C_{5-10}$ carbocyclic residue substituted with 1–5 $R^{32}$; and, a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:
phenyl; phenethyl; phenoxy; benzyloxy; $C_3$–$C_{10}$ cycloalkyl; $C_3$–$C_6$ cycloalkylmethyl; $C_{2-6}$ alkoxy-$C_{2-6}$ alkyl; halogen; —$CO_2R^{13}$; —$CONR^{13}NR^{13}R^{14}$; cyano; —CHO; $C_3$–$C_6$ cycloalkoxy; —$NR^{13}R^{14}$; —$C(R^{14})$=$N(OR^{14})$; $NO_2$; —$OR^{13}$; $NR^{14}(C=O)R^{11}$; —C(=O)$NR^{11}R^{14}$; —C(=O)$NR^{13}R^{14}$; —OC(=O)$NR^{13}R^{14}$; —C(=O)$R^{11}$; —OC(=O)$R^{11}$; —$OCO_2R^{13}$; $C_1$–$C_4$ haloalkyl; $C_1$–$C_4$ haloalkoxy; $C_1$–$C_4$ alkyl substituted with 1–2 groups selected from: $R^{11}$, =$NR^{14}$, =$NNR^{13}C(=O)NR^{13}R^{14}$ =$NNR^{13}C(=O)OR^{13}$, or —$NR^{13}R^{14}$;

$C_{2-4}$ alkenyl substituted with 1–2 $R^{11}$;
$C_{2-4}$ alkynyl substituted with 1–2 $R^{11}$; or
a 5- to 10-membered heterocyclic ring containing from 1 to 3 heteroatoms independently selected from oxygen, nitrogen or sulfur, said heterocyclic ring being substituted with 0–2 $R^{12}$;

$R^{33}$ is selected from the following:
phenyl substituted with 0–3 $R^{11a}$;
benzyl substituted with 0–3 $R^{11a}$;
$C_{1-4}$ alkyl substituted with 1–3 $R^{11a}$; $C_{2-4}$ alkenyl substituted with 0–3 $R^{11a}$; and, an amine protecting group when $R^{33}$ is bonded to N; a hydroxy protecting group when $R^{33}$ is bonded to O;

provided that $R^4$ and $R^5$ together do not represent unsubstituted straight or branched alkyl.

[3] In an even more preferred embodiment, the present invention provides novel compounds of formula (IIb):

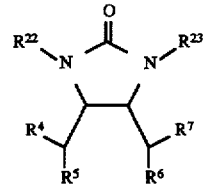

(IIb)

or pharmaceutically acceptable salt or prodrug forms thereof, wherein;

$R^4$ and $R^7$ are independently selected from the following: —$NOR^{13}R^{13}$;
$C_{1-6}$ alkyl substituted with 0–2 $R^{11}$;
$C_{2-4}$ alkenyl substituted with 0–2 $R^{11}$; or
a $C_5$–$C_{10}$ carbocyclic ring system substituted with 0–2 $R^{11}$ or $R^{12}$;

$R^5$ and $R^6$ are independently selected from the following: hydrogen, halogen, —$N(R^{20})_2$, —$OR^{20}$, =O, or $C_{1-4}$ alkyl substituted with 0–2 $R^{11}$;

$R^{11}$ is selected from the following:
hydrogen; halogen; cyano; —$NR^{13}R^{14}$; —$OR^{13}$; $C_{1-2}$ haloalkyl; $C_{1-2}$
alkyl substituted with 0–2 $R^{12}$;
a $C_{5-7}$ carbocyclic residue substituted with 0–2 $R^{12}$;
a 5- to 10-membered heterocyclic ring system containing 1 to 3 heteroatoms independently selected from oxygen, nitrogen or sulfur, said heterocyclic ring system being substituted with 0–2 $R^{12}$;

$R^{11a}$ is selected from the following:

halogen; cyano; —$CH_2NH_2$; —$NH_2$; —$NH(C_1$-$C_3$ alkyl); —OH;

—$C(=O)NH_2$; $C_3$-$C_6$ cycloalkyl; $C_3$-$C_6$ cycloalkylmethyl; phenoxy;

benzyloxy; nitro; $C_1$-$C_4$ hydroxyalkyl; $C_1$-$C_4$ haloalkyl; or $C_1$-$C_4$ alkylcarbonyl;

$R^{12}$ is selected from the following:

phenyl; halogen; hydroxy; nitro; cyano; $C_1$-$C_4$ alkyl substituted with 0–2 $OR^{13}$, $SR^{13}$, or $NR^{11}R^{13}$; $C_3$-$C_6$ cycloalkylmethyl; $C_1$-$C_4$ alkoxy; —$CO_2H$; $C_3$-$C_6$ cycloalkoxy; —$OR^{13}$; —$NR^{13}R^{14}$; $C_{1-6}$ alkoxy $C_{1-6}$ alkyl; $C_1$-$C_4$ hydroxyalkyl; $C_1$-$C_4$ haloalkyl; $C_1$-$C_4$ alkylcarbonyloxy; or $C_1$-$C_4$ alkylcarbonyl;

$R^{13}$ is selected from the following:

hydrogen;

phenyl substituted with 0–2 $R^{11a}$;

benzyl substituted with 0–2 $R^{11a}$;

$C_{1-4}$ alkyl substituted with 0–2 $R^{11a}$; or $C_{2-4}$ alkenyl substituted with 0–3 $R^{11a}$;

$R^{14}$ is selected from the following:

hydrogen; phenyl; benzyl; an amine protecting group when $R^{14}$ is bonded to N; or $C_{1-4}$ alkyl substituted with 0–3 groups selected from OH or halogen;

$R^{20}$ is selected from the following:

hydrogen;

$C_{1-5}$ alkoxycarbonyl substituted with 0–3 $R^{11}$;

benzoyl substituted with 0–3 $R^{12}$; or any group that, when administered to a mammalian subject, cleaves to form a free hydroxyl, amino or sulfhydryl;

m is 0, 1 or 2;

$R^{22}$ and $R^{23}$ are independently selected from the following:

$C_{1-6}$ alkyl substituted with 1–3 $R^{31}$;

$C_{2-4}$ alkenyl substituted with 1–3 $R^{31}$; or a $C_{3-10}$ carbocyclic ring system substituted with 1–2 $R^{31}$ or $R^{32}$;

$R^{22}$ and $R^{23}$ can independently be unsubstituted $C_{2-8}$ alkenyl when either $R^5$ or $R^6$ or both are halogen;

$R^{31}$ is selected from the following:

halogen; cyano; —$NR^{33}R^{14}$; —$CO_2R^{13}$; —$C(=O)R^{33}$; —$OC(=O)R^{33}$;

—$OR^{33}$; —$C(=O)NR^{13}R^{14}$; $C_{3-7}$ cycloalkyl; nitro; $C_{1-4}$ haloalkyl;

a $C_{5-8}$ carbocyclic residue substituted with 1–3 $R^{32}$; or a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:

phenyl; phenethyl; phenoxy; benzyloxy; $C_{3-6}$ cycloalkyl; halogen; —$CO_2R^{13}$; cyano; $C_{3-6}$ cycloalkoxy; —$NR^{13}R^{14}$; $NO_2$; —$OR^{13}$; $NR^{14}(C=O)R^{11}$; —$C(=O)NR^{11}R^{14}$; —$C(=O)NR^{13}R^{14}$; —$C(=O)R^{11}$; —$OC(=O)R^{11}$; —$OCO_2R^{13}$; $C_1$-$C_4$ haloalkyl; $C_1$-$C_4$ haloalkoxy; $C_1$-$C_4$ alkyl substituted with 1–2 groups selected from: $R^{11}$, =$NR^{14}$, or —$NR^{13}R^{14}$;

$C_{2-4}$ alkenyl substituted with 1–2 $R^{11}$; or a 5- to 10-membered heterocyclic ring containing from 1 to 3 heteroatoms independently selected from oxygen, nitrogen or sulfur, said heterocyclic ring being substituted with 0–2 $R^{12}$;

$R^{33}$ is selected from the following:

phenyl substituted with 0–2 $R^{11a}$;

benzyl substituted with 0–2 $R^{11a}$;

$C_{1-4}$ alkyl substituted with 1–2 $R^{11a}$; and, $C_{2-4}$ alkenyl substituted with 0–2 $R^{11a}$;

provided that $R^4$ and $R^5$ together do not represent unsubstituted straight or branched alkyl.

[4] In a still more preferred embodiment, the present invention provides novel compounds of formula (IIb) or pharmaceutically acceptable salt or prodrug forms thereof, wherein;

$R^4$ and $R^7$ are independently $C_{1-4}$ alkyl substituted with 0–2 $R^{11}$ or —$N(CH_3)(OCH_3)$ ;

$R^5$ and $R^6$ are independently selected from the following: hydrogen, halogen, =O, $C_{1-2}$ alkyl substituted with 0–2 $R^{11}$ or —$OR^{20}$;

$R^{11}$ is selected from the following:

hydrogen;

$C_{1-2}$ alkyl substituted with 0–2 $OR^{13}$;

phenyl substituted with 0–2 $R^{12}$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{12}$ is selected from the following:

$C_1$-$C_4$ alkyl; —$NR^{13}R^{14}$; —$OR^{13}$; $C_{1-2}$ alkoxy-$C_{1-2}$ alkyl-; or $R^{13}O$-$C_{1-2}$ alkyl-;

$R^{13}$ is selected from the following:

hydrogen;

phenyl substituted with 0–2 $R^{11a}$;

benzyl substituted with 0–2 $R^{11a}$; or $C_{1-2}$ alkyl substituted with 0–2 $R^{11a}$;

$R^{14}$ is selected from the following: hydrogen or $C_{1-2}$ alkyl substituted with 0–2 OH or halogen $R^{20}$ is hydrogen or any group that, when administered to a mammalian subject, cleaves to form a free hydroxyl;

$R^{22}$ and $R^{23}$ are independently selected from the following:

$C_1$-$C_6$ alkyl substituted with $R^{31}$, or $C_2$-$C_3$ alkenyl substituted with $R^{31}$;

$R^{22}$ and $R^{23}$ can independently be unsubstituted $C_{2-8}$ alkenyl when either $R^5$ or $R^6$ or both are halogen;

$R^{31}$ is selected from the following:

$C_{3-5}$ cycloalkyl; $C_{5-7}$ carbocyclic substituted with 1–2 $R^{32}$; and, a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:

—$C(=O)NR^{11}R^{14}$; —$NR^{14}C(=O)R^{11}$; halogen; cyano; —$NR^{13}R^{14}$; —$OR^{13}$; —$CO_2R^{13}$; —$C(=O)R^{11}$;

$C_1$-$C_2$ alkyl substituted with 0–2 groups selected from: —$OR^{13}$, =$NR^{14}$, or —$NR^{13}R^{14}$; or a 5- to 10-membered heterocyclic ring system containing 1 to 3 heteroatoms independently selected from oxygen, nitrogen or sulfur, said heterocyclic ring system being substituted with 0–2 $R^{12}$;

provided that $R^4$ and $R^5$ together do not represent unsubstituted straight or branched alkyl.

[5] In an even further preferred embodiment, the present invention provides novel compounds of formula (IIc):

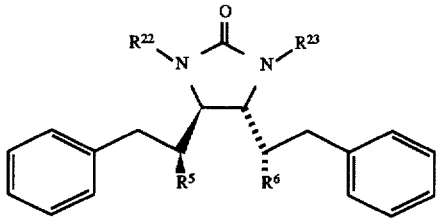
(IIc)

or pharmaceutically acceptable salt or prodrug forms thereof, wherein;

$R^5$ and $R^6$ are independently selected from the following: hydrogen, hydroxy, F, Cl, Br, I, or $CH_2OH$;

$R^{22}$ and $R^{23}$ are independently —$CH_2$—$R^{31}$;

$R^{22}$ and $R^{23}$ independently may also be allyl when either $R^5$ or $R^6$ or both are halogen;

$R^{31}$ is selected from the following: cyclopropyl, phenyl substituted with 1–2 $R^{32}$, naphthyl, pyridyl; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{12}$ is selected from the following: methyl, ethyl, propyl, n-butyl, t-butyl, amino, methylamino, dimethylamino, ethylamino, diethylamino, methoxy, ethoxy, OH, $CH_3OCH_2$—, $CH_3CH_2OCH_2$—, phenoxymethyl, or benzyloxymethyl;

$R^{32}$ is selected from the following: —$C(=O)NR^{11}R^{14}$; —$NHC(=O)R^{11}$; F; I; cyano; methyl, —$CH_2OH$; —$CH_2CH_2OH$; —OH, —$CO_2CH_3$; —$C(O)CH_3$; pyridyl; ($CH_3C(=NOH)$); ($H_2NC(=NOH)$); or a 5- to 10-membered heterocyclic ring system containing 1 to 3 heteroatoms independently selected from oxygen, nitrogen or sulfur, said heterocyclic ring system being substituted with 0–2 $R^{12}$;

$R^{11}$ is selected from the following: hydrogen; —$CH_2OH$; —$CH_2CH_2OH$; or a 5- to 10-membered heterocyclic ring system containing 1 to 3 heteroatoms independently selected from oxygen, nitrogen or sulfur, said heterocyclic ring system being substituted with 0–2 $R^{12}$; and $R^{14}$ is selected from the following: hydrogen, —$CH_2OH$, or —$CH_2CH_2OH$.

[6] In a specifically preferred embodiment, the present invention provides novel compounds of formula (IIc) or pharmaceutically acceptable salt or prodrug forms thereof, wherein;

$R^5$ and $R^6$ are independently selected from H, OH, F, Br, or $CH_2OH$; and $R^{22}$ and $R^{23}$ are as follows:

$R^{22}$ is cyclopropylmethyl and $R^{23}$ is benzyl;
$R^{22}$ is cyclopropylmethyl and $R^{23}$ is 3-hydroxybenzyl;
$R^{22}$ is cyclopropylmethyl and $R^{23}$ is 4-hydroxybenzyl;
$R^{22}$ is cyclopropylmethyl and $R^{23}$ is 3-aminobenzyl;
$R^{22}$ is cyclopropylmethyl and $R^{23}$ is 4-pyridylmethyl;
$R^{22}$ is 3-aminobenzyl and $R^{23}$ is 2-naphthylmethyl;
$R^{22}$ is 3-aminobenzyl and $R^{23}$ is 4-hydroxymethylbenzyl;
$R^{22}$ is 3-aminobenzyl and $R^{23}$ is 3-hydroxybenzyl;
$R^{22}$ is 4-hydroxymethylbenzyl and $R^{23}$ is 3-hydroxybenzyl;
$R^{22}$ is 2-naphthylmethyl and $R^{23}$ is 4-hydroxymethylbenzyl;
$R^{22}$ is allyl and $R^{23}$ is benzyl;
$R^{22}$ is benzyl and $R^{23}$ is 3-hydroxybenzyl;
$R^{22}$ is benzyl and $R^{23}$ is 2-naphthylmethyl; or
$R^{22}$ is benzyl and $R^{23}$ is 4-pyridylmethyl;

$R^{22}$ and $R^{23}$ are independently the same group and are selected from the following:

cyclopropylmethyl;
4-fluorobenzyl;
3-iodobenzyl;
2-napthylmethyl;
2-pyridylmethyl;
3-pyridylmethyl;
4-pyridylmethyl;
3-(2-pyridyl)benzyl;
3-(3'-pyridyl)benzyl;
3-(4-pyridyl)benzyl;
3-methylbenzyl;
3-ethylbenzyl;
3-cyanobenzyl;
3-hydroxybenzyl;
4-hydroxybenzyl;
3,4-dihydroxybenzyl;
3-hydroxymethylbenzyl;
4-hydroxymethylbenzyl;
3-(2-hydroxyethyl)benzyl;
3-acetylbenzyl;
3-carbomethoxybenzyl;
3-($CH_3C(=NOH)$)benzyl;
3-($H_2NC(=N—OH)$)benzyl;
3-aminobenzyl;
4-aminobenzyl;
3-aminocarbonylbenzyl;
3-N-methylaminocarbonylbenzyl;
3-N,N-dimethylaminocarbonylbenzyl;
3-N-ethylaminocarbonylbenzyl;
3-N,N-diethylaminocarbonylbenzyl;
3-(2-hydroxymethylaminocarbonyl)benzyl;
3-(2-hydroxyethylaminocarbonyl)benzyl;
5-indazolylmethyl;
6-indazolylmethyl;
3-aminoindazol-5-ylmethyl;
3-(methylamino)indazol-5-ylmethyl;
3-(dimethylamino)indazol-5-ylmethyl;
3-(ethylamino)indazol-5-ylmethyl;
3-(diethylamino)indazol-5-ylmethyl;
3-methoxy-indazol-5-ylmethyl;
3-ethoxy-indazol-5-ylmethyl;
3-(phenoxymethyl)indazol-5-ylmethyl;
3-methylindazol-5-ylmethyl;
3-ethylindazol-5-ylmethyl;
indazolinon-5-ylmethyl;
indazolinon-6-ylmethyl;
benzoxazolinon-5-ylmethyl;
benzoxazolinon-6-ylmethyl;
5-benzisoxazolyl-5-methyl
3-methylbenzisoxazol-5-ylmethyl;
3-ethylbenzisoxazol-5-ylmethyl;
3-aminobenzisoxazol-5-ylmethyl;
3-(methylamino)benzisoxazol-5-ylmethyl;
3-(dimethylamino)benzisoxazol-5-ylmethyl;
3-(ethylamino)benzisoxazol-5-ylmethyl;
3-(diethylamino)benzisoxazol-5-ylmethyl;
5-benzisothiazolylmethyl;
3-methylbenzisothiazol-5-ylmethyl;
3-ethylbenzisothiazol-5-ylmethyl;
3-aminobenzisothiazol-5-ylmethyl;
3-(methylamino)benzisothiazol-5-ylmethyl;
3-(dimethylamino)benzisothiazol-5-ylmethyl;
3-(ethylamino)benzisothiazol-5-ylmethyl;
3-(diethylamino)benzisothiazol-5-ylmethyl;
3-(diazol-3'-yl)benzyl;
3-(4'-methyldiazol-3'-yl)benzyl;
3-(5'-methyldiazol-3'-yl)benzyl;
3-(4'-ethyldiazol-3'-yl)benzyl;

3-(5'-ethyldiazol-3'-yl)benzyl.;
3-(4',5'-dimethyldiazol-3'-yl)benzyl;
3-(4',5'-diethyldiazol-3'-yl)benzyl;
3-(4'-aminodiazol-3'-yl)benzyl;
3-(5'-aminodiazol-3'-yl)benzyl;
3-(4'-(methylamino)diazol-3'-yl)benzyl;
3-(51-(methylamino)diazol-3'-yl)benzyl;
3-(4'-(ethylamino)diazol-3'-yl)benzyl;
3-(5'-(ethylamino)diazol-3'-yl)benzyl;
3-(4'-(dimethylamino)diazol-3'-yl)benzyl;
3-(5'-(dimethylamino)diazol-3'-yl)benzyl;
3-(4'-(diethylamino)diazol-3'-yl)benzyl;
3-(5'-(diethylamino)diazol-3'-yl)benzyl;
3-oxazol-3'-ylbenzyl;
3-(4'-methyloxazol-3'-yl)benzyl;
3-(5'-methyloxazol-3'-yl)benzyl;
3-(4'-ethyloxazol-3'-yl)benzyl;
3-(5'-ethyloxazol-3'-yl)benzyl;
3-(4',5'-dimethyloxazol-3'-yl)benzyl;
3-(4',5'-diethyloxazol-3'-yl)benzyl;
3-(4'-aminooxazol-3'-yl)benzyl;
3-(5'-aminooxazol-3'-yl)benzyl;
3-(4'-(methylamino)oxazol-3'-yl)benzyl;
3-(5'-(methylamino)oxazol-3'-yl)benzyl;
3-(4'-(dimethylamino)oxazol-3'-yl)benzyl;
3-(5'-(dimethylamino)oxazol-3'-yl)benzyl;
3-(4'-(ethylamino)oxazol-3'-yl)benzyl;
3-(5'-(ethylamino)oxazol-3'-yl)benzyl;
3-(4'-(diethylamino)oxazol-3'-yl)benzyl;
3-(5'-(diethylamino)oxazol-3'-yl)benzyl;
3-isoxazol-3'-ylbenzyl;
3-(4'-methylisoxazol-3'-yl)berizyl;
3-(5'-methylisoxazol-3'-yl)benzyl;
3-(4'-ethylisoxazol-3'-yl)benzyl;
3-(5'-ethylisoxazol-3'-yl)benzyl;
3-(4',5'-dimethylisoxazol-3'-yl)benzyl;
3-(4',5'-diethylisoxazol-3'-yl)benzyl;
3-(4'-aminoisoxazol-3'-yl)benzyl;
3-(5'-aminoisoxazol-3'-yl)benzyl;
3-(4'-(methylamino)isoxazol-3'-yl)benzyl;
3-(5'-(methylamino)isoxazol-3'-yl)benzyl;
3-(4'-(dimethylamino)isoxazol-3'-yl)benzyl;
3-(5'-(dimethylamino)isoxazol-3'-yl)benzyl;
3-(4'-(ethylamino)isoxazol-3'-yl)benzyl;
3-(5'-(ethylamino)isoxazol-3'-yl)benzyl;
3-(4'-(diethylamino)isoxazol-3'-yl)benzyl;
3-(5'-(diethylamino)isoxazol-3'-yl)benzyl;
3-(2-triazoly)benzyl;
3-(5-methyltriazol-2-yl)benzyl;
3-(5-ethyltriazol-2-yl)benzyl,
3-(5-aminotriazol-2-yl)benzyl;
3-(5-(methylamino)triazol-2-yl)benzyl;
3-(5-(dimethylamino)triazol-2-yl)benzyl;
3-(5-(ethylamino)triazol-2-yl)benzyl;
3-(5-(diethylamino)triazol-2-yl)benzyl;
3-triazol-3'-ylbenzyl;
3-(5'-methyltriazol-3'-yl)benzyl;
3-(5'-ethyltriazol-3'-yl)benzyl;
3-(5'-aminotriazol-3'-yl)benzyl;
3-(5'-(methylamino)triazol-3'-yl)benzyl;
3-(5'-(dimethylamino)triazol-3'-yl)bénzyl;
3-(5'-(ethylamino)triazol-3'-yl)benzyl;
3-(5'-(diethylamino)triazol-3'-yl)benzyl;
3-(2-imidazolyl)benzyl;
3-(4-methylimidazol-2-yl)benzyl;
3-(4,5-dimethylimidazol-2-yl)benzyl;
4-aminoimidazol-2-yl)benzyl;
3-(4-(methylamino)imidazol-2-yl)benzyl;
3-(4-(di-methylamino)imidazol-2-yl)benzyl;
3-(4-(ethylamino)imidazol-2-yl)benzyl;
3-(4-(diethylamino)imidazol-2-yl)benzyl;
3-(5-aminoimidazol-2-yl)benzyl;
3-(5-(methylamino)imidazol-2-yl)benzyl;
3-(5-(dimethylamino)imidazol-2-yl)benzyl;
3-(5-(ethylamino)imidazol-2-yl)benzyl;
3-(5-(diethylamino)imidazol-2-yl)benzyl;
3-(2-imidazolyl-aminocarbonyl)benzyl;
3-(4-methylimidazol-2-yl-aminocarbonyl)benzyl;
3-(4,5-dimethylimidazol-2-yl-aminocarbonyl)benzyl;
3-(4-aminoimidazol-2-yl-aminocarbonyl)benzyl;
3-(4-(methylamino)imidazol-2-yl-aminocarbonyl)benzyl;
3-(4-(dimethylamino)imidazol-2-yl-aminocarbonyl)benzyl;
3-(4-(ethylamino)imidazol-2-y-amiinocarbonyl)benzyl;
3-(4-(diethylamino)imidazol-2-yl-aminocarbonyl)benzyl;
3-(5-aminoimidazol-2-yl-aminocarbonyl)benzyl;
3-(5-(methylamino)imidazol-2-yl-aminocarbonyl)benzyl;
3-(5-(dimethylamino)imidazol-2-yl-aminocarbonyl)benzyl;
3-(5-(ethylamino)imidazol-2-yl-aminocarbonyl)benzyl;
3-(5-(diethylamino)imidazol-2-yl-aminocarbonyl)benzyl;
3-(2-pyridyl-aminocarbonyl)benzyl;
3-(3'-pyridyl-aminocarbonyl)benzyl;
3-(4-pyridyl-aminocarbonyl)benzyl;
3-(1',3',4'-thiadiazol-2'-yl-aminocarbonyl)benzyl;
3-(5-methylthiadiazol-2-yl-aminocarbonyi)benzyl;
3-(5-ethylthiadiazol-2-yl-aminocarbonyl)benzyl;
3-(5-t-butylthiadiazol-2-yl-aminocarbonyl)benzyl;
3-(5-aminothiadiazol-2-yl-aminocarbonyl)benzyl;
3-(5-(methylamino)thiadiazol-2-yl-aminocarbonyl)benzyl;
3-(5-(dimethylamino)thiadiazol-2-yl-aminocarbonyl) benzyl;
3-(5-(ethylamino)thiadiazol-2-yl-aminocarbonyl)benzyl;
3-(5-(diethylamino)thiadiazol-2-yl-aminocarbonyl)benzyl;
3-(2-thiazolyl-aminocarbonyl)benzyl;
3-(4-methylthiazol-2-yl-aminocarbonyl)benzyl;
3-(5-methylthiazol-2-yl-aminocarbonyl)benzyl;
3-(4,5-dimethylthiazol-2-yl-aminocarbonyl)benzyl;
3-(4-ethylthiazol-2-yl-aminocarbonyl)benzyl;
3-(5-ethylthiazol-2-yl-aminocarbonyl)benzyl;
3-(4,5-diethylthiazol-2-yl-aminocarbonyl)benzyl;
3-(4-aminothiazol-2-yl-aminocarbonyl)benzyl;
3-(5-aminothiazol-2-yl-aminocarbonyl)benzyl;
3-(4-(methylamino)thiazol-2-yl-aminocarbonyl)benzyl;
3-(5-(methylamino)thiazol-2-yl-aminocarbonyl)benzyl;
3-(4-(ethylamino)thiazol-2-yl-aminocarbonyl)benzyl;
3-(5-(ethylamino)thiazol-2-yl-aminocarbonyl)benzyl;
3-(2-triazolyl-aminocarbonyl)benzyl;
3-(5-methyltriazol-2-yl-aminocarbonyl)benzyl;
3-(5-ethyltriazol-2-yl-aminocarbonyl)benzyl;
3-(5-aminotriazol-2-yl-aminocarbonyl)benzyl;
3-(5-(methylamino)triazol-2-yl-aminocarbonyl)benzyl;
3-(5-(dimethylamino)triazol-2-yl-aminocarbonyl)benzyl;
3-(5-(ethylamino)triazol-2-yl-aminocarbonyl)benzyl; or
3-(5-(diethylamino)triazol-2-yl-aminocarbonyl)benzyl; or
when at least on of $R^5$ or $R^6$ is other than H, $R^{22}$ or $R^{23}$ may, independently, both be allyl.

[7] Most preferred compounds of the present invention are wherein $R^5$ and $R^6$ are as follows:

$R^5$ and $R^6$ are both F;

$R^5$ and $R^6$ are both H;

$R^5$ and $R^6$ are both $CH_2OH$;

$R^5$ is H and $R^6$ is $CH_2OH$;

$R^5$ is H and $R^6$ is OH; or $R^5$ is H and $R^6$ is Br.

[8] In another more preferred embodiment, the present invention provides novel compounds of formula (II) or pharmaceutically acceptable salt or prodrug forms thereof, wherein;

$R^1$ and $R^2$, together, are —C(H)($R^4$)C(H)($R^5$)C(H)($R^6$)C(H)($R^7$)—;

J is C(=O), S(O), or S(O)$_2$;

$R^5$ and $R^6$ are independently H, F, Br, =O, or OH;

$R^4$ and $R^7$ are independently $C_{1-2}$ alkyl substituted with 0–1 $R^{11}$;

$R^{11}$ is selected from the following:
hydrogen;
$C_{1-2}$ alkyl substituted with 0–2 $OR^{13}$;
phenyl substituted with 0–2 $R^{12}$; or
a 5- to 10-membered heterocyclic ring system containing 1 to 3 heteroatoms independently selected from oxygen, nitrogen or sulfur, said heterocyclic ring system being substituted with 0–2 $R^{12}$;

$R^{12}$ is selected from the following:
$C_1$–$C_4$ alkyl; —$NR^{13}R^{14}$; —$OR^{13}$; $C_{1-2}$ alkoxy-$C_{1-2}$ alkyl-; or $R^{13}$O—$C_{1-2}$ alkyl-;

$R^{13}$ is selected from the following:
hydrogen;
phenyl substituted with 0–2 $R^{11a}$;
benzyl substituted with 0–2 $R^{11a}$; or
$C_{1-2}$ alkyl substituted with 0–2 $R^{11a}$;

$R^{14}$ is selected from the following: hydrogen or $C_{1-2}$ alkyl substituted with 0–2 OH or halogen $R^{22}$ and $R^{23}$ are independently selected from the following:
$C_1$–$C_6$ alkyl substituted with 0–1 $R^{31}$; or
a 5- to 10-membered heterocyclic ring system containing 1 to 3 heteroatoms independently selected from oxygen, nitrogen or sulfur, said heterocyclic ring system being substituted with 0–2 $R^{12}$;

$R^{31}$ is selected from the following:
OH; $C_{3-5}$ cycloalkyl;
$C_{5-7}$ carbocyclic substituted with 0–2 $R^{32}$; or
a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following: —C(=O)$NR^{11}R^{14}$; —$NR^{14}$C(=O)$R^{11}$; halogen; cyano; —$NR^{13}R^{14}$; —$OR^{13}$; —$CO_2R^{13}$; —C(=O) $R^{11}$;
$C_1$–$C_2$ alkyl substituted with 0–2 groups selected from: —$OR^{13}$, =$NR^{14}$, or —$NR^{13}R^{14}$; or
a 5- to 10-membered heterocyclic ring system containing 1 to 3 heteroatoms independently selected from oxygen, nitrogen or sulfur, said heterocyclic ring system being substituted with 0–2 $R^{12}$.

[9] In a preferred embodiment, the present invention provides novel compounds of formula (IId):

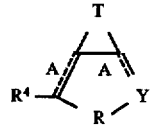

(IId)

or a pharmaceutically acceptable salt form or prodrug thereof, wherein:

R is $CR^5$=X;
X is $CR^6$, C—$OR^{13}$, or N;
Y is $CR^7$, C—$OR^{13}$, or N;

each A is a double bond;

$R^4$ and $R^7$ are independently selected from the following:
hydrogen; —$CO_2R^{13}$; —$NR^{11}R^{13}$;
$C_1$–$C_8$ alkyl substituted with 0–3 $R^{11}$;
$C_2$–$C_8$ alkenyl substituted with 0–3 $R^{11}$;
$C_2$–$C_8$ alkynyl substituted with 0–3 $R^{11}$;
a $C_3$–$C_{14}$ carbocyclic ring system substituted with 0–3 $R^{11}$ or $R^{12}$; or
a 5- to 10-membered heterocyclic ring system containing 1 to 3 heteroatoms independently selected from oxygen, nitrogen or sulfur, said heterocyclic ring system being substituted with 0–2 $R^{12}$;

$R^5$ and $R^6$ are independently selected from the following:
hydrogen, halogen, —N($R^{20}$)$_2$, —$SR^{20}$, —$OR^{20}$, or $C_1$–$C_6$ alkyl substituted with 0–3 $R^{11}$;

$R^5$ and $R^6$ can alternatively join to form —OCH$_2$SCH$_2$O—, —OS(=O)O—, —OC(=O)O—, —OCH$_2$O—, —OC(=S)O—, —OC(=O)C(=O)O—, —OC(CH$_3$)$_2$O—, —OC((CH$_2$)$_3$NH$_2$)(CH$_3$)O—, —OCH$_2$OCH$_2$O—, —OC(OCH$_3$)(CH$_2$CH$_2$CH$_3$)O—, —NHC(=O)NH—, —OC(=O)NH—, —NHC(=O)O—, —NHCH$_2$O—, —OCH$_2$NH—, —NHC(=S)O—, —OS(=O)NH—, —NHC(=O)C(=O)O—, —OC(=O)C(=O)NH—, —NHC(=O)C(=O)NH—, —NHC(CH$_3$)$_2$O—, —OC(CH$_3$)$_2$NH—
or any group that, when administered to a mammalian subject, cleaves to form a free dihydroxyl or diamino or hydroxyl and amino;

$R^{11}$ is selected from the following:
hydrogen; keto; halogen; cyano; —CH$_2$$NR^{13}R^{14}$; —$NR^{13}R^{14}$; —$CO_2R^{13}$; —OC(=O) $R^{13}$; $OR^{13}$; —S(O)$_m$ $R^{13}$; —C(=O)$NR^{13}R^{14}$; —SO$_2$$NR^{13}R^{14}$; $C_2$–$C_4$ alkenyl; $C_3$–$C_6$ cycloalkylmethyl; nitro; $C_7$–$C_{10}$ arylalkyl; formyl; $C_3$–$C_6$ cycloalkoxy; methylenedioxy; ethylenedioxy; $C_1$–$C_4$ haloalkyl; $C_1$–$C_4$ haloalkoxy, $C_1$–$C_4$ alkoxycarbonyl; pyridylcarbonyloxy; $C_1$–$C_4$ alkylcarbonyl;
$C_3$–$C_{10}$ cycloalkyl substituted with 0–2 $R^{12}$;
$C_1$–$C_4$ alkyl substituted with 0–2 $R^{12}$;
aryl-$C_1$–$C_3$ alkyl substituted with 0–2 $R^{12}$;
$C_{2-6}$ alkoxy-$C_{2-6}$ alkyl substituted with 0–2 $R^{12}$;
a $C_5$–$C_{14}$ carbocyclic residue substituted with 0–3 $R^{12}$;
a 5- to 10-membered heterocyclic ring system containing 1 to 3 heteroatoms independently selected from oxygen, nitrogen or sulfur, said heterocyclic ring system being substituted with 0–3 $R^{12}$;

$R^{11a}$ is selected from the following:
hydrogen; keto; halogen; cyano; —CH$_2$NH$_2$; —NH$_2$; —NH($C_1$–$C_3$ alkyl); —CO$_2$H; —OC(=O)($C_1$–$C_3$ alkyl); —OH; $C_{1-6}$ alkoxy-$C_{1-6}$ alkyl; —C(=O)NH$_2$; —SO$_2$NH$_2$; $C_1$–$C_4$ alkyl; $C_2$–$C_4$ alkenyl; $C_3$–$C_{10}$ cycloalkyl; $C_3$–$C_6$ cycloalkylmethyl; phenoxy; benzyloxy; nitro; $C_3$–$C_6$ cycloalkoxy; $C_1$–$C_4$ alkyl substituted with —NH$_2$; $C_1$–$C_4$ hydroxyalkyl; methylenedioxy; ethylenedioxy; $C_1$–$C_4$ haloalkyl;
$C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; 2-(1-morpholino)ethoxy; aryl-$C_1$–$C_3$ alkyl;
a $C_5$–$C_{14}$ carbocyclic residue; a 5- to 10-membered heterocyclic ring system containing 1 to 3 heteroatoms independently selected from oxygen, nitrogen or sulfur, said heterocyclic ring system substituted with 0–3 $R^{12a}$;

$R^{12}$, when a substituent on carbon, is selected from the following:
phenyl; halogen; hydroxy; nitro; cyano; $C_1$–$C_4$ alkyl substituted with 0–2 $OR^{13}$; $C_3$–$C_6$ cycloalkyl; $C_3$–$C_6$ cycloalkylmethyl; $C_7$–$C_{10}$ arylalkyl; $C_1$–$C_4$ alkoxy; —$CO_2H$; hydroxamic acid; hydrazide; boronic acid; sulfonamide; formyl; $C_3$–$C_6$ cycloalkoxy; —$OR^{13}$; —$NR^{13}R^{14}$; $C_1$–$C_4$ alkyl substituted with —$NR^{13}R^{14}$; $C_{1-6}$ alkoxy $C_{1-6}$ alkyl substituted with 0 or 1 —$Si(CH_3)_3$; $C_1$–$C_4$ hydroxyalkyl; methylenedioxy; ethylenedioxy; $C_1$–$C_4$ haloalkyl; $C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; —$S(O)_mR^{13}$; —$SO_2NR^{13}R^{14}$; —$NHSO_2R^{14}$; —$OCH_2CO_2R^{13}$; 2-(1-morpholino)ethoxy; —$C(R^{14})$=$N(OR^{13})$;

a 5- or 6-membered heterocyclic ring containing from 1 to 3 heteroatoms independently selected from oxygen, nitrogen or sulfur, the heterocyclic ring system being substituted with 0–3 $R^{12a}$;

a 3- or 4-carbon chain attached to adjacent carbons on the ring to which it is appended to form a fused 5- or 6-membered ring, said 5- or 6-membered ring being optionally substituted on any of the aliphatic carbons with halogen, $C_1$–$C_4$ alkyl, $C_1$–$C_4$ alkoxy, hydroxy, —$NR^{13}R^{14}$; or when $R^{12}$ is attached to a saturated carbon atom, it may be =O or =S, or when $R^{12}$ is attached to sulfur it may be =O;

$R^{12}$, when a substituent on nitrogen, is selected from the following:

phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —$CH_2NR^{13}R^{14}$; —$NR^{13}R^{14}$; $C_{1-6}$ alkoxy-$C_{1-6}$ alkyl; $C_1$–$C_4$ haloalkyl; $C_1$–$C_4$ alkoxycarbonyl; —$CO_2H$; $C_1$–$C_4$ alkylcarbonyloxy; $C_1$–$C_4$ alkylcarbonyl;

$R^{12a}$, when a substituent on carbon, is selected from one or more of the following:

phenyl; benzyl; phenethyl; phenoxy; benzyloxy; halogen; hydroxy; nitro; cyano; $C_1$–$C_4$ alkyl; $C_3$–$C_6$ cycloalkyl; $C_3$–$C_6$ cycloalkylmethyl; $C_7$–$C_{10}$ arylalkyl; $C_1$–$C_4$ alkoxy; —$CO_2H$; formyl; $C_3$–$C_6$ cycloalkoxy; —$OH^{13}$; $C_1$–$C_4$ alkyl substituted with —$NH_2$ or —$NHMe$; $C_{1-6}$ alkoxy-$C_{1-6}$ alkyl optionally substituted with —$Si(CH_3)_3$; $C_1$–$C_4$ hydroxyalkyl; $C_1$–$C_4$ haloalkyl; $C_1$–$C_4$ haloalkoxy; $C_1$–$C_4$ alkoxycarbonyl; $C_1$–$C_4$ alkylcarbonyloxy; $C_1$–$C_4$ alkylcarbonyl; $C_1$–$C_4$ alkylcarbonylamino; —$S(O)_mMe$; —$SO_2NH_2$; —$NHSO_2Me$; —$OCH_2CO_2R^{13}$; or 2-(1-morpholino)ethoxy;

$R^{12a}$, when a substituent on nitrogen, is selected from the following:

phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; $C_1$–$C_4$ haloalkyl; $C_1$–$C_4$ alkoxycarbonyl; or $C_1$–$C_4$ alkylcarbonyl;

$R^{13}$ is selected from the following:

hydrogen;

phenyl substituted with 0–3 $R^{11a}$;

benzyl substituted with 0–3 $R^{11a}$;

$C_1$–$C_6$ alkyl substituted with 0–3 $R^{11a}$;

$C_1$–$C_6$ alkylcarbonyl substituted with 0–3 $R^{11a}$;

$C_1$–$C_6$ alkoxycarbonyl substituted with 0–3 $R^{11a}$;

$C_1$–$C_6$ alkylaminocarbonyl substituted with 0–3 $R^{11a}$;

$C_3$–$C_6$ alkoxyalkyl substituted with 0–3 $R^{11a}$;

an amine protecting group when $R^{13}$ is bonded to N;

a hydroxy protecting group when $R^{13}$ is bonded to O; or, a 5- to 10-membered heterocyclic ring system containing 1 to 3 heteroatoms independently selected from oxygen, nitrogen or sulfur, the heterocyclic ring system being substituted with 0–3 $R^{12a}$;

$R^{14}$ is selected from the following: hydrogen; hydroxy; $C_1$–$C_6$ alkoxy; $NH_2$; —$NH(C_1$–$C_4$ alkyl); $C_2$–$C_6$ alkenyl; phenyl; benzyl; an amine protecting group when $R^{14}$ is bonded to N; or $C_1$–$C_6$ alkyl substituted with 0–3 groups selected from OH, $C_1$–$C_4$ alkoxy, halogen, $NH_2$;

$R^{13}$ and $R^{14}$, when attached to the same N atom, can alternatively join to form: —$(CH_2)_4$—; —$(CH_2)_5$—; —$CH_2CH_2N(R^{15})CH_2CH_2$—; or —$CH_2CH_2OCH_2CH_2$—;

$R^{15}$ is hydrogen or methyl;

$R^{20}$ is selected from the following:

hydrogen;

$C_1$–$C_6$ alkyl substituted with 0–3 $R^{11}$;

$C_3$–$C_6$ alkoxyalkyl substituted with 0–3 $R^{11}$;

$C_1$–$C_6$ alkoxycarbonyl substituted with 0–3 $R^{11}$;

$C_1$–$C_6$ alkylaminocarbonyl substituted with 0–3 $R^{11}$;

benzoyl substituted with 0–3 $R^{12}$;

phenoxycarbonyl substituted with 0–3 $R^{12}$;

phenylaminocarbonyl substituted with 0–3 $R^{12}$; or any group that, when administered to a mammalian subject, cleaves to form a free hydroxyl, amino or sulfhydryl;

m is 0, 1 or 2;

T is selected from:

—$N(R^{22})C(=Z)N(R^{23})$—;

—$N(R^{22})P(=O)(R^{24a})N(R^{23})$—;

Z is O, S, or $NR^{24}$;

$R^{22}$ and $R^{23}$ are independently selected from the following:

—$OR^{22a}$; —$N(R^{22a})(R^{22b})$;

$C_1$–$C_8$ alkyl substituted with 1–3 $R^{31}$;

$C_2$–$C_8$ alkenyl substituted with 1–3 $R^{31}$;

$C_2$–$C_8$ alkynyl substituted with 0–3 $R^{31}$;

a $C_3$–$C_{14}$ carbocyclic ring system substituted with 1–5 $R^{31}$;

a 5- to 10-membered heterocyclic ring system containing 1 to 3 heteroatoms independently selected from oxygen, nitrogen or sulfur, said heterocyclic ring system being substituted with 0–2 $R^{32}$;

$R^{22}$ and $R^{23}$ may both be hydrogen when at least one of X or Y is N;

$R^{22}$ and $R^{23}$ may, when at least one of X or Y is C—$OR^{13}$ or N, independently be $C_{2-8}$ alkenyl substituted with 1–3 $C_3$–$C_{14}$ carbocyclic ring systems each ring system being substituted with 1–5 $R^{31}$;

$R^{22a}$ and $R^{22b}$ are independently selected from the following:

$C_{1-8}$ alkyl substituted with 1–3 $R^{31}$;

$C_{1-8}$ alkyl substituted with from 1–3 $C_{3-14}$ carbocyclic ring systems each ring system being substituted with 0–5 $R^{12}$;

$C_{2-8}$ alkenyl substituted with 0–3 $R^{31}$;

$C_{2-8}$ alkynyl substituted with 0–3 $R^{31}$;

a $C_3$–$C_{14}$ carbocyclic ring system substituted with 0–5 $R^{31}$ or $R^{32}$; or a 5- to 10-membered heterocyclic ring system containing 1 to 3 heteroatoms independently selected from oxygen, nitrogen or sulfur, said heterocyclic ring system being substituted with 0–2 $R^{32}$;

$R^{24}$ is selected from the following: hydrogen; hydroxy; amino; $C_1$–$C_4$ alkyl; $C_1$–$C_4$ alkoxy; mono-($C_1$–$C_6$ alkyl)amino; di-($C_1$–$C_6$ alkyl)amino; cyano; nitro; benzyloxy; or —$NHSO_2$aryl, aryl being substituted with 0–1 ($C_1$–$C_6$)alkyl;

$R^{24a}$ is selected from the following:

hydroxy; amino; $C_1$–$C_4$ alkyl; $C_1$–$C_4$ alkoxy; mono-($C_1$–$C_6$ alkyl)amino; di-($C_1$–$C_6$ alkyl)amino; benzyloxy; or phenoxy;

$R^{31}$ is selected from the following:

halogen; —OC(=O)$R^{13}$; $C_{1-6}$ alkoxy-$C_{1-6}$ alkoxy; —S(O)$_m$ $R^{13}$; —NHC(=NH)NHR$^{13}$; —C(=NH)NHR$^{13}$; —C(=NOR$^{11}$)NR$^{13}$R$^{14}$; —NR$^{14}$C(=O)R$^{13}$; =NOR$^{14}$; —NR$^{14}$C(=O)OR$^{14}$; —OC(=O)NR$^{13}$R$^{14}$; —NR$^{13}$C(=S)NR$^{13}$R$^{14}$; —NR$^{14}$SO$_2$NR$^{13}$R$^{14}$; —NR$^{14}$SO$_2$R$^{13}$; —SO$_2$NR$^{13}$R$^{14}$; nitro; hydroxamic acid; hydrazide; oxime; boronic acid; sulfonamide; formyl; $C_3$–$C_6$ cycloalkoxy; methylenedioxy; ethylenedioxy; $C_{1-4}$ haloalkyl; $C_{1-4}$ haloalkoxy; —OCH$_2$CO$_2$R$^{13}$; 2-(1-morpholino)ethoxy; azido; —C(R$^{14}$)=N(OR$^{14}$); and, 1-3 amino acids, linked together via amide bonds, said amino acid being linked via the amine or carboxylate terminus;

$R^{32}$, when a substituent on carbon, is selected from the following:

phenyl; phenoxy; phenethyl; $C_3$–$C_{10}$ cycloalkyl; $C_3$–$C_6$ cycloalkylmethyl; $C_7$–$C_{10}$ arylalkyl; hydrazide; hydroxamic acid; boronic acid; oxime; $C_{1-6}$ alkoxy-$C_{1-6}$ alkyl; methylenedioxy; ethylenedioxy; $C_1$–$C_4$ alkylcarbonyloxy; —NHSO$_2$R$^{14}$; phenylmethoxy; halogen; 2-(1-morpholino)ethoxy; —CO$_2$R$^{13}$; —CONR$^{13}$NR$^{13}$R$^{14}$; cyano; —CHO; $C_3$–$C_6$ cycloalkoxy; —NR$^{13}$R$^{14}$; —C(R$^{14}$)=N(OR$^{14}$); NO$_2$; —NR$^{40}$R$^{41}$; —SO$_m$R$^{13}$; —SO$_m$NR$^{13}$R$^{14}$; $^{NR14}$(C=O)R$^{11}$; —C(=O)NR$^{11}$R$^{14}$; —C(=O)NR$^{13}$R$^{14}$; —OC(=O)NR$^{13}$R$^{14}$; —C(=O) R$^{11}$; —OC(=O) R$^{11}$; —OCO$_2$R$^{13}$; phenyl; —C(=O)NR$^{13}$—(C$_1$–C$_4$ alkyl)-NR$^{13}$R$^{14}$; —C(=O)NR$^{40}$R$^{41}$; $C_1$–$C_4$ haloalkyl; $C_1$–$C_4$ haloalkoxy; $C_2$–$C_4$ haloalkenyl; $C_1$–$C_4$ haloalkynyl; —C(=O).NR$^{13}$C(R$^{11}$)$_2$NR$^{13}$R$^{14}$; —C(=O) NR$^{13}$C(R$^{11}$)$_2$NR$^{13}$NR$^{14}$ —C(=O)NR$^{13}$C(R$^{11}$)$_2$ NR$^{13}$CO$_2$R$^{13}$; —C(=O)NR$^{13}$—(C$_1$–C$_4$ alkyl)-NR$^{13}$CO$_2$R$^{13}$; —C(=O)N(R$^{13}$)—(C$_1$–C$_4$ alkyl)—R$^{11}$; —C(=O)C(R$^{11}$)$_2$NR$^{13}$R$^{14}$; —C(=O) C(R$^{11}$)$_2$ NR$^{13}$NR$^{14}$; —C(=O)C(R$^{11}$)$_2$NR$^{13}$CO$_2$R$^{13}$; —C(=O)-(C$_1$–C$_4$ alkyl)-NR$^{13}$R$^{14}$—C(=O)-(C$_1$–C$_4$ alkyl)-NR$^{13}$CO$_2$R$^{13}$;

$C_1$–$C_4$ alkoxy substituted with 0-4 groups selected from: $R^{11}$, $C_3$–$C_6$ cycloalkyl, —CO$_2$R$^{13}$, —C(=O)NR$^{13}$R$^{14}$, —NR$^{13}$R$^{14}$ or OH;

$C_2$–$C_4$ alkenyl substituted with 0-4 R$^{11}$;

$C_2$–$C_4$ alkynyl substituted with 0-4 R$^{11}$;

a 5- to 10-membered heterocyclic ring containing from 1 to 3 heteroatoms independently selected from oxygen, nitrogen or sulfur, said heterocyclic ring being substituted with 0-2 R$^{12}$;

a 3- or 4-carbon chain wherein 0, 1 or 2 of the carbon atoms are replaced with a heteroatom independently selected from oxygen, nitrogen or sulfur, attached to an adjacent carbon on the ring to which it is appended to form a fused 5- or 6-membered ring, said 5- or 6-membered ring being optionally substituted on the aliphatic carbons with 0-3 halogen, $C_1$–$C_4$ alkyl, $C_1$–$C_4$ alkoxy, hydroxy, or —NR$^{13}$R$^{14}$; or, when R$^{32}$ is attached to a saturated carbon atom, it may be =O =S or =NOH; or when R$^{32}$ is attached to sulfur it may be =O;

$R^{32}$, when a substituent on nitrogen, is selected from the following: phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —CH$_2$NR$^{13}$R$^{14}$; —NR$^{13}$R$^{14}$; $C_{1-6}$ alkoxy-$C_{1-6}$ alkyl; $C_1$–$C_4$ haloalkyl; $C_1$–$C_4$ alkoxycarbonyl; —CO$_2$H; $C_1$–$C_4$ alkylcarbonyloxy; and, —C(R$^{14}$)=N(OR$^{14}$);

$R^{40}$ is hydrogen or $C_1$–$C_3$ alkyl; and, $R^{41}$ is selected from the following:

—C(=O)NR$^{13}$R$^{14}$; —C(=O)NR$^{13}$NR$^{13}$R$^{14}$; —C(=O)C(R$^{11}$)$_2$NR$^{13}$R$^{14}$; —C(=O)C(R$^{11}$)$_2$NR$^{13}$NR$^{13}$R$^{14}$; —C(=O)C(R$^{11}$)$_2$NR$^{13}$CO$_2$R$^{13}$; —C(=O)H;

—C(=O) R$^{11}$; —C(=O)-(C$_1$–C$_4$ alkyl)-NR$^{13}$R$^{14}$; —C(=O)-(C$_1$–C$_4$ alkyl)-NR$^{13}$CO$_2$R$^{13}$; and 1-3 amino acids linked together via amide bonds and linked to the N atom via the carboxylate terminus;

provided that when neither $R^{22}$ nor $R^{23}$ are thiadiazole.

[10] In another more preferred embodiment, the present invention provides novel compounds of formula (IId) or pharmaceutically acceptable salt or prodrug forms thereof, wherein:

T is —N(R$^{22}$)C(=O)N(R$^{23}$)—

R is CH=X;

X is CH, C—OR$^{13}$, or N;

Y is CH, C—OR$^{13}$, or N;

each A is a double bond;

$R^4$ is hydrogen;

$R^{22}$ and $R^{23}$ are independently selected from the following: OR$^{22a}$ and $C_{1-2}$ alkyl substituted with R$^{31}$;

$R^{22}$ and $R^{23}$ may both be hydrogen when at least one of X or Y is N;

$R^{22}$ and $R^{23}$ may, when at least one of X or Y is C—OR$^{13}$ or N, independently be $C_{2-8}$ alkenyl substituted with 1-3 $C_3$–$C_{14}$ carbocyclic ring systems each ring system being substituted with 1-5 R$^{31}$;

$R^{22a}$ is selected from the following: $C_{1-2}$ alkyl substituted with phenyl substituted with 0-2 R$^{12}$ or $C_{1-2}$ alkyl substituted with naphthyl substituted with 0-2 R$^{12}$;

$R^{12}$ is selected from the following: $C_{1-4}$ alkyl substituted with 0-2 OR$^{13}$, amino, methylamino, dimethylamino, ethylamino, diethylamino, methoxy, ethoxy;

$R^{13}$ is selected from the following: hydrogen, methyl, ethyl, phenyl, $C_{1-2}$ alkoxy-$C_{1-2}$ alkyl or a 5- to 10-membered heterocyclic ring system containing 1 to 3 heteroatoms independently selected from oxygen, nitrogen or sulfur, said heterocyclic ring system being substituted with 0-2 R$^{32}$;

$R^{31}$ is $C_{1-3}$ alkoxy-$C_{1-3}$ alkoxy; and, $R^{32}$ is $C_{1-2}$ alkyl substituted with 0-2 OR$^{13}$.

[11] In a another preferred embodiment, the present invention provides novel compounds of formula (IId):

(IId)

or a pharmaceutically acceptable salt form or prodrug thereof, wherein:

R is O, S(O)$_m$, NH, or NOR$^{13}$;

Y is C(H)(R$^7$);

each A is a single bond;

$R^4$ and $R^7$ are independently selected from the following: hydrogen; —CO$_2$R$^{13}$; —NR$^{11}$R$^{13}$;

$C_1$–$C_8$ alkyl substituted with 0-3 R$^{11}$;

$C_2$–$C_8$ alkenyl substituted with 0-3 R$^{11}$;

$C_2$–$C_8$ alkynyl substituted with 0-3 R$^{11}$;

a $C_3$–$C_{14}$ carbocyclic ring system substituted with 0-3 R$^{11}$ or R$^{12}$; or a 5- to 10-membered heterocyclic ring system containing 1 to 3 heteroatoms independently selected from oxygen, nitrogen or sulfur, said heterocyclic ring system being substituted with 0-2 R$^{12}$;

$R^{11}$ is selected from the following:

hydrogen; keto; halogen; cyano; —CH$_2$NR$^{13}$R$^{14}$; —NR$^{13}$R$^{14}$; —CO$_2$R$^{13}$; —OC(=O)R$^{13}$; —OR$^{13}$;

—S(O)$_m$R$^{13}$; —C(=O)NR$^{13}$R$^{14}$; —SO$_2$NR$^{13}$R$^{14}$; C$_2$–C$_4$ alkenyl; C$_3$–C$_6$ cycloalkylmethyl; nitro; C$_7$–C$_{10}$ arylalkyl; formyl; C$_3$–C$_6$ cycloalkoxy; methylenedioxy; ethylenedioxy; C$_1$–C$_4$ haloalkyl; C$_1$–C$_4$ haloalkoxy; pyridylcarbonyloxy; C$_1$–C$_4$ alkylcarbonyl;

C$_3$–C$_{10}$ cycloalkyl substituted with 0–2 R$^{12}$;

C$_1$–C$_4$ alkyl substituted with 0–2 R$^{12}$;

aryl-C$_1$–C$_3$ alkyl substituted with 0–2 R$^{12}$;

C$_{2-6}$ alkoxy-C$_{2-6}$ alkyl substituted with 0–2 R$^{12}$;

a C$_5$–C$_{14}$ carbocyclic residue substituted with 0–3 R$^{12}$;

a 5- to 10-membered heterocyclic ring system containing 1 to 3 heteroatoms independently selected from oxygen, nitrogen or sulfur, said heterocyclic ring system being substituted with 0–3 R$^{12}$;

R$^{11a}$ is selected from the following:

hydrogen; keto; halogen; cyano; —CH$_2$NH$_2$; —NH$_2$; —NH (C$_1$–C$_3$ alkyl); —CO$_2$H; —OC(=O)(C$_1$–C$_3$ alkyl); —OH; C$_{1-6}$ alkoxy-C$_{1-6}$ alkyl; —C(=O)NH$_2$; —SO$_2$NH$_2$; C$_1$–C$_4$ alkyl; C$_2$–C$_4$ alkenyl; C$_3$–C$_{10}$ cycloalkyl; C$_3$–C$_6$ cycloalkylmethyl; phenoxy; benzyloxy; nitro; C$_3$–C$_6$ cycloalkoxy; C$_1$–C$_4$ alkyl substituted with —NH$_2$; C$_1$–C$_4$ hydroxyalkyl; methylenedioxy; ethylenedioxy; C$_1$–C$_4$ haloalkyl; C$_1$–C$_4$ haloalkoxy; C$_1$–C$_4$ alkoxycarbonyl; C$_1$–C$_4$ alkylcarbonyloxy; C$_1$–C$_4$ alkylcarbonyl; C$_1$–C$_4$ alkylcarbonylamino; 2-(1-morpholino)ethoxy; aryl-C$_1$–C$_3$ alkyl;

a C$_5$–C$_{14}$ carbocyclic residue; a 5- to 10-membered heterocyclic ring system containing 1 to 3 heteroatoms independently selected from oxygen, nitrogen or sulfur, said heterocyclic ring system substituted with 0–3 R$^{12a}$;

R$^{12}$, when a substituent on carbon, is selected from the following:

phenyl; halogen; hydroxy; nitro; cyano; C$_1$–C$_4$ alkyl substituted with 0–2 OR$^{13}$; C$_3$–C$_6$ cycloalkyl; C$_3$–C$_6$ cycloalkylmethyl; C$_7$–C$_{10}$ arylalkyl; C$_1$–C$_4$ alkoxy; —CO$_2$H; hydroxamic acid; hydrazide; boronic acid; sulfonamide; formyl; C$_3$–C$_6$ cycloalkoxy; —OR$^{13}$; —NR$^{13}$R$^{14}$; C$_1$–C$_4$ alkyl substituted with —NR$^{13}$R$^{14}$; C$_{1-6}$ alkoxy C$_{1-6}$ alkyl substituted with 0 or 1 —Si(CH$_3$)$_3$; C$_1$–C$_4$ hydroxyalkyl; methylenedioxy; ethylenedioxy; C$_1$–C$_4$ haloalkyl; C$_1$–C$_4$ haloalkoxy; C$_1$–C$_4$ alkoxycarbonyl; C$_1$–C$_4$ alkylcarbonyloxy; C$_1$–C$_4$ alkylcarbonyl; C$_1$–C$_4$ alkylcarbonylamino; —S(O)$_m$R$^{13}$; —SO$_2$NR$^{13}$R$^{14}$; —NHSO$_2$R$^{14}$; —OCH$_2$CO$_2$R$^{13}$; 2-(1-morpholino)ethoxy; —C(R$^{14}$)=N(OR$^{13}$); a 5- or 6-membered heterocyclic ring containing from 1 to 3 heteroatoms independently selected, from oxygen, nitrogen or sulfur, the heterocyclic ring system being substituted with 0–3 R$^{12a}$;

a 3- or 4-carbon chain attached to adjacent carbons on the ring to which it is appended to form a fused 5- or 6-membered ring, said 5- or 6-membered ring being optionally substituted on any of the aliphatic carbons with halogen, C$_1$–C$_4$ alkyl, C$_1$–C$_4$ alkoxy, hydroxy, —NR$^{13}$R$^{14}$; or when R$^{12}$ is attached to a saturated carbon atom, it may be =O or =S, or when R$^{12}$ is attached to sulfur it may be =O;

R$^{12}$, when a substituent on nitrogen, is selected from the following:

phenyl; benzyl; phenethyl; hydroxy; C$_1$–C$_4$ hydroxyalkyl; C$_1$–C$_4$ alkoxy; C$_1$–C$_4$ alkyl; C$_3$–C$_6$ cycloalkyl; C$_3$–C$_6$ cycloalkylmethyl; —CH$_2$NR$^{13}$R$^{14}$; —NR$^{13}$R$^{14}$; C$_{1-6}$ alkoxy-C$_{1-6}$ alkyl; C$_1$–C$_4$ haloalkyl; C$_1$–C$_4$ alkoxycarbonyl; —CO$_2$H; C$_1$–C$_4$ alkylcarbonyloxy; C$_1$–C$_4$ alkylcarbonyl;

R$^{12a}$, when a substituent on carbon, is selected from one or more of the following:

phenyl; benzyl; phenethyl; phenoxy; benzyloxy; halogen; hydroxy; nitro; cyano; C$_1$–C$_4$ alkyl; C$_3$–C$_6$ cycloalkyl; C$_3$–C$_6$ cycloalkylmethyl; C$_7$–C$_{10}$ arylalkyl; C$_1$–C$_4$ alkoxy; —CO$_2$H; formyl; C$_3$–C$_6$ cycloalkoxy; —OH$^{13}$; C$_1$–C$_4$ alkyl substituted with —NH$_2$ or —NHMe; C$_{1-6}$ alkoxy-C$_{1-6}$ alkyl optionally substituted with —Si(CH$_3$)$_3$; C$_1$–C$_4$ hydroxyalkyl; C$_1$–C$_4$ haloalkyl; C$_1$–C$_4$ haloalkoxy; C$_1$–C$_4$ alkoxycarbonyl; C$_1$–C$_4$ alkylcarbonyloxy; C$_1$–C$_4$ alkylcarbonyl; C$_1$–C$_4$ alkylcarbonylamino; —S(O)$_m$Me; —SO$_2$NH$_2$; —NHSO$_2$Me; —OCH$_2$CO$_2$R$^{13}$; or 2-(1-morpholino)ethoxy;

R$^{12a}$, when a substituent on nitrogen, is selected from the following:

phenyl; benzyl; phenethyl; hydroxy; C$_1$–C$_4$ hydroxyalkyl; C$_1$–C$_4$ alkoxy; C$_1$–C$_4$ alkyl; C$_3$–C$_6$ cycloalkyl; C$_3$–C$_6$ cycloalkylmethyl; C$_1$–C$_4$ haloalkyl; C$_1$–C$_4$ alkoxycarbonyl; or C$_1$–C$_4$ alkylcarbonyl;

R$^{13}$ is selected from the following:

hydrogen;

phenyl substituted with 0–3 R$^{11a}$;

benzyl substituted with 0–3 R$^{11a}$;

C$_1$–C$_6$ alkyl substituted with 0–3 R$^{11a}$;

C$_2$–C$_4$ alkenyl substituted with 0–3 R$^{11a}$;

C$_1$–C$_6$ alkylcarbonyl substituted with 0–3 R$^{11a}$;

C$_1$–C$_6$ alkoxycarbonyl substituted with 0–3 R$^{11a}$;

C$_1$–C$_6$ alkylaminocarbonyl substituted with 0–3 R$^{11a}$;

C$_3$–C$_6$ alkoxyalkyl substituted with 0–3 R$^{11a}$;

an amine protecting group when R$^{13}$ is bonded to N;

a hydroxy protecting group when R$^{13}$ is bonded to O; or, a 5- to 10-membered heterocyclic ring system containing 1 to 3 heteroatoms independently selected from oxygen, nitrogen or sulfur, the heterocyclic ring system being substituted with 0–3 R$^{12a}$;

R$^{14}$ is selected from the following:

hydrogen; hydroxy; C$_1$–C$_6$ alkoxy; NH$_2$; —NH (C$_1$–C$_4$ alkyl) ; C$_2$–C$_6$ alkenyl; phenyl; benzyl; an amine protecting group when R$^{14}$ is bonded to N; or C$_1$–C$_6$ alkyl substituted with 0–3 groups selected from OH, C$_1$–C$_4$ alkoxy, halogen, NH$_2$;

R$^{13}$ and R$^{14}$, when attached to the same N atom, can alternatively join to form: —(CH$_2$)$_4$—; —(CH$_2$)$_5$—; —CH$_2$CH$_2$N(R$^{15}$)CH$_2$CH$_2$—; or —CH$_2$CH$_2$OCH$_2$CH$_2$—;

R$^{15}$ is: hydrogen or methyl;

R$^{20}$ is selected from the following:

hydrogen;

C$_1$–C$_6$ alkyl substituted with 0–3 R$^{11}$;

C$_3$–C$_6$ alkoxyalkyl substituted with 0–3 R$^{11}$;

C$_1$–C$_6$ alkylcarbonyl substituted with 0–3 R$^{11}$;

C$_1$–C$_6$ alkoxycarbonyl substituted with 0–3 R$^{11}$;

C$_1$–C$_6$ alkylaminocarbonyl substituted with 0–3 R$^{11}$;

benzoyl substituted with 0–3 R$^{12}$;

phenoxycarbonyl substituted with 0–3 R$^{12}$;

phenylaminocarbonyl substituted with 0–3 R$^{12}$; or any group that, when administered to a mammalian subject, cleaves to form a free hydroxyl, amino or sulfhydryl;

m is 0, 1 or 2;

T is selected from:

—N(R$^{22}$)C(=Z)N(R$^{23}$)—;

—N(R$^{22}$)S(=Z')N(R$^{23}$)—;

—N(R$^{22}$)S(=Z)$_2$N(R$^{23}$)—; or

—N(R$^{22}$)P(=O)(R$^{24a}$)N(R$^{23}$)—;

Z is O, S, NR$^{24}$;

Z' is O or NR$^{24}$;

R$^{22}$ and R$^{23}$ are independently selected from the following:

—OR$^{22a}$; —N(R$^{22a}$) (R$^{22b}$);

C$_1$–C$_8$ alkyl substituted with 1–3 R$^{31}$;

C$_2$–C$_8$ alkenyl substituted with 1–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$;

a 5- to 10-membered heterocyclic ring system containing 1 to 3 heteroatoms independently selected from oxygen, nitrogen or sulfur, said heterocyclic ring system being substituted with 0–2 R$^{32}$;

R$^{22a}$ and R$^{22b}$ are independently selected from the following:

hydrogen;

C$_1$–C$_8$ alkyl substituted with 0–3 R$^{31}$;

C$_2$–C$_8$ alkenyl substituted with 0–3 R$^{31}$;

C$_2$–C$_8$ alkynyl substituted with 0–3 R$^{31}$;

a C$_3$–C$_{14}$ carbocyclic ring system substituted with 0–5 R$^{31}$ or R$^{32}$; or a 5- to 10-membered heterocyclic ring system containing 1 to 3 heteroatoms independently selected from oxygen, nitrogen or sulfur, said heterocyclic ring system being substituted with 0–2 R$^{32}$;

R$^{24}$ is selected from the following:

hydrogen; hydroxy; amino; C$_1$–C$_4$ alkyl; C$_1$–C$_4$ alkoxy; mono-(C$_1$–C$_6$ alkyl)amino; di-(C$_1$–C$_6$ alkyl)amino; cyano; nitro; benzyloxy; or —NHSO$_2$aryl, aryl being substituted with 0–1 (C$_1$–C$_6$)alkyl;

R$^{24a}$ is selected from the following:

hydroxy; amino; C$_1$–C$_4$ alkyl; C$_1$–C$_4$ alkoxy; mono-(C$_1$–C$_6$ alkyl)amino; di-(C$_1$–C$_6$ alkyl)amino; benzyloxy; or phenoxy;

R$^{31}$ is selected from the following: halogen; cyano; —NR$^{13}$R$^{14}$; —CO$_2$R$^{13}$; —C(=O)R$^{11}$; —OC(=O)R$^{13}$; —S(O)$_m$R$^{13}$; —NHC(=NH)NHR$^{13}$; —C(=NH)NHR$^{13}$; —C(=O)NR$^{13}$R$^{14}$; —C(=NOR$^{11}$)NR$^{13}$R$^{14}$; —NR$^{14}$C(=O)R$^{13}$; =NOR$^{14}$; —NR$^{14}$C(=O)OR$^{14}$; —OC(=O)NR$^{13}$R$^{14}$; —NR$^{13}$C(=S)NR$^{13}$R$^{14}$; —NR$^{14}$SO$_2$NR$^{13}$R$^{14}$; —NR$^{14}$SO$_2$R$^{13}$; —SO$_2$NR$^{13}$R$^{14}$; C$_3$–C$_{10}$ cycloalkyl; C$_3$–C$_6$ cycloalkylmethyl; phenoxy; benzyloxy; nitro; hydroxamic acid; hydrazide; oxime; boronic acid; sulfonamide; formyl; C$_3$–C$_6$ cycloalkoxy; C$_1$–C$_4$ alkyl substituted with —NR$^{13}$R$^{14}$; C$_1$–C$_4$ hydroxyalkyl; methylenedioxy; ethylenedioxy; C$_{1-4}$ haloalkyl; C$_{1-4}$ haloalkoxy; —OCH$_2$CO$_2$R$^{13}$; 2-(1-morpholino)ethoxy; azido; —C(R$^{14}$)=N(OR$^{14}$); 1–3 amino acids, linked together via amide bonds, said amino acid being linked via the amine or carboxylate terminus; a C$_5$–C$_{14}$ carbocyclic residue substituted with 1–5 R$^{32}$; or a 5- to 10-membered heterocyclic ring system containing 1 to 3 heteroatoms independently selected from oxygen, nitrogen or sulfur, said heterocyclic ring system being substituted with 0–2 R$^{12}$;

R$^{32}$, when a substituent on carbon, is independently:

phenyl; phenethyl; phenoxy; C$_3$–C$_{10}$ cycloalkyl; C$_3$–C$_6$ cycloalkylmethyl; C$_7$–C$_{10}$ arylalkyl; hydrazide; hydroxamic acid; boronic acid; oxime; C$_{1-6}$ alkoxy-C$_{1-6}$ alkyl; C$_1$–C$_4$ alkylcarbonyloxy; —NHSO$_2$R$^{14}$; phenylmethoxy; halogen; 2-(1-morpholino)ethoxy; —CO$_2$R$^{13}$; —CONR$^{13}$NR$^{13}$R$^{14}$; cyano; —CHO; —NR$^{13}$R$^{14}$; —C(R$^{14}$)=N(OR$^{14}$); NO$_2$; —NR$^{40}$R$^{41}$; —SO$_m$R$^{13}$; —SO$_m$NR$^{13}$R$^{14}$; NR$^{14}$(C=O)R$^{11}$; —C(=O)NR$^{11}$R$^{14}$; —C(=O)NR$^{13}$R$^{14}$; —OC(=O)NR$^{13}$R$^{14}$; —C(=O)R$^{11}$; —OC(=O)R$^{11}$; —OCO$_2$R$^{13}$; phenyl; —C(=O)NR$^{13}$—(C$_1$–C$_4$ alkyl)-NR$^{13}$R$^{14}$; —C(=O)NR$^{40}$R$^{41}$; C$_1$–C$_4$ haloalkyl; C$_1$–C$_4$ haloalkoxy; C$_2$–C$_4$ haloalkenyl; C$_1$–C$_4$ haloalkynyl; —C(=O) NR$^{13}$C(R$^{11}$)$_2$NR$^{13}$R$^{14}$; —C(=O) NR$^{13}$C(R$^{11}$)$_2$NR$^{13}$NR$^{14}$; —C(=O) NR$^{13}$C(R$^{11}$)$_2$NR$^{13}$CO$_2$R$^{13}$; —C(=O)NR$^{13}$—(C$_1$–C$_4$ alkyl)-NR$^{13}$CO$_2$R$^{13}$; —C(=O)N(R$^{13}$)-(C$_1$–C$_4$ alkyl)-R$^{11}$; —C(=O)C(R$^{11}$)$_2$NR$^{13}$R$^{14}$; —C(=O)C(R$^{11}$)$_2$NR$^{13}$NR$^{14}$; —C(=O)C(R$^{11}$)$_2$NR$^{13}$CO$_2$R$^{13}$; —C(=O)-(C$_1$–C$_4$ alkyl)-NR$^{13}$R$^{14}$; —C(=O)-(C$_1$–C$_4$ alkyl)-NR$^{13}$CO$_2$R$^{13}$;

C$_1$–C$_4$ alkyl substituted with 1–4 groups selected from: OR$^{13}$, =NR$^{14}$, =NNR$^{13}$C(=O)NR$^{13}$R$^{14}$ =NNR$^{13}$C(=O)OR$^{13}$, or —NR$^{13}$R$^{14}$;

C$_2$–C$_4$ alkenyl substituted with 0–4 R$^{11}$;

C$_2$–C$_4$ alkynyl substituted with 0–4 R$^{11}$;

a 5- to 10-membered heterocyclic ring containing from 1 to 3 heteroatoms independently selected from oxygen, nitrogen or sulfur, said heterocyclic ring being substituted with 0–2 R$^{12}$; and, a 3- or 4-carbon chain, wherein 0, 1 or 2 of the carbon atoms are replaced with a heteroatom independently selected from oxygen, nitrogen or sulfur, attached to an adjacent carbon on the ring to which it is appended to form a fused 5- or 6-membered ring, said 5- or 6-membered ring being substituted on the aliphatic carbons with 0–3 halogen, C$_1$–C$_4$ alkyl, C$_1$–C$_4$ alkoxy, hydroxy, —NR$^{13}$R$^{14}$;

when R$^{32}$ is attached to a saturated carbon atom, it may be =O =S or =NOH; or when R$^{32}$ is attached to sulfur it may be =O;

R$^{32}$, when a substituent on nitrogen, is independently:

phenyl; benzyl; phenethyl; hydroxy; C$_1$–C$_4$ hydroxyalkyl; C$_1$–C$_4$ alkoxy; C$_1$–C$_4$ alkyl; C$_3$–C$_6$ cycloalkyl; C$_3$–C$_6$ cycloalkylmethyl; —CH$_2$NR$^{13}$R$^{14}$; —NR$^{13}$R$^{14}$; C$_{1-6}$ alkoxy-C$_{1-6}$ alkyl; C$_1$–C$_4$ haloalkyl; C$_1$–C$_4$ alkoxycarbonyl; —CO$_2$H; C$_1$–C$_4$ alkylcarbonyloxy; C$_1$–C$_4$ alkylcarbonyl; —C(R$^{14}$)=N(OR$^{14}$);

R$^{40}$ is hydrogen or C$_1$–C$_3$ alkyl;

R$^{41}$ is selected from —C(=O)NR$^{13}$R$^{14}$; —C(=O)NR$^{13}$NR$^{13}$R$^{14}$; —C(=O)C(R$^{11}$)$_2$NR$^{13}$R$^{14}$; —C(=O)C(R$^{11}$)$_2$NR$^{13}$NR$^{13}$R$^{14}$; —C(=O)C(R$^{11}$)$_2$NR$^{13}$CO$_2$R$^{13}$; —C(=O)H; —C(=O)R$^{11}$; —C(=O)-(C$_1$–C$_4$ alkyl)-NR$^{13}$R$^{14}$; —C(=O)-(C$_1$–C$_4$ alkyl)-NR$^{13}$CO$_2$R$^{13}$; or 1–3 amino acids linked together via amide bonds, and linked to the N atom via the carboxylate terminus.

[12] In another more preferred embodiment, the present invention provides novel compounds of formula (IId) or pharmaceutically acceptable salt or prodrug forms thereof, wherein:

each A is a single bond;

R is O, S(O)$_m$, NH, or NOR$^{13}$;

R$^4$ is H;

T is —N(R$^{22}$)C(=O)N(R$^{23}$)—;

m is 0, 1, or 2;

R$^7$ is C$_{1-6}$ alkyl substituted with 0–2 R$^{11}$;

R$^{11}$ is selected from the following:

—OR$^{13}$; —CO$_2$R$^{13}$; —C(=O)OR$^{13}$; —C(=O)R$^{13}$;

aryl(substituted with 0–2 R$^{12}$)-C$_{1-2}$ alkyl

R$^{12}$ is halogen, C$_{1-2}$ alkyl or SEM;

R$^{13}$ is selected from the following:

hydrogen;

C$_{1-2}$ alkyl substituted with 0–1 R$^{11a}$; or benzyl substituted with 0–1 R$^{11a}$;

R$^{11a}$ is selected from the following:

halogen, C$_{1-2}$ alkylcarbonyl, C$_{1-2}$ alkyl substituted with 0–2 OR$^{13}$ or =NOR$^{13}$;

R$^{22}$ and R$^{23}$ are —CH$_2$—R$^{31}$;

31

$R^{31}$ is phenyl substituted with 1-2 $R^{32}$; and, $R^{32}$ is selected from the following: Br, —C(O)CH$_3$, C$_{1-2}$ alkyl substituted with 1-2 groups selected from —OH or =NOR$^{13}$; or a 5- to 10-membered heterocyclic ring system containing 1 to 3 heteroatoms independently selected from oxygen, nitrogen or sulfur, said heterocyclic ring system being substituted with 0-2 $R^{12}$.

[13] In a another preferred embodiment, the present invention provides novel compounds of formula (IId):

(IId)

or a pharmaceutically acceptable salt form or prodrug thereof, wherein:

R is O, S(O)$_m$, NH, NOH, or NOR$^{13}$;

Y is C(R$^7$);

each A is a double bond;

$R^4$ and $R^7$ are independently selected from the following: hydrogen; —CO$_2$R$^{13}$; —NR$^{11}$R$^{13}$;

C$_1$–C$_8$ alkyl substituted with 1-3 $R^{11}$;

C$_2$–C$_8$ alkenyl substituted with 0-3 $R^{11}$;

C$_2$–C$_8$ alkynyl substituted with 0-3 $R^{11}$;

a C$_3$–C$_{14}$ carbocyclic ring system substituted with 0-3 $R^{11}$ or $R^{12}$; or a 5- to 10-membered heterocyclic ring system containing 1 to 3 heteroatoms independently selected from oxygen, nitrogen or sulfur, said heterocyclic ring system being substituted with 0-2 $R^{12}$;

$R^{11}$ is selected from the following:

keto; halogen; cyano; —CH$_2$NR$^{13}$R$^{14}$; —NR$^{13}$R$^{14}$; —CO$_2$R$^{13}$; —OC(=O)R$^{13}$; —OR$^{13}$; —S(O)$_m$R$^{13}$; —C(=O)NR$^{13}$R$^{14}$; —SO$_2$NR$^{13}$R$^{14}$; C$_2$–C$_4$ alkenyl; C$_3$–C$_6$ cycloalkylmethyl; nitro; C$_7$–C$_{10}$ arylalkyl; formyl; C$_3$–C$_6$ cycloalkoxy; methylenedioxy; ethylenedioxy; C$_1$–C$_4$ haloalkyl; C$_1$–C$_4$ haloalkoxy; pyridylcarbonyloxy; C$_1$–C$_4$ alkylcarbonyl;

C$_3$–C$_{10}$ cycloalkyl substituted with 0-2 $R^{12}$;

C$_1$–C$_4$ alkyl substituted with 1-2 $R^{12}$;

aryl-C$_1$–C$_3$ alkyl substituted with 0-2 $R^{12}$;

C$_{2-6}$ alkoxy-C$_{2-6}$ alkyl substituted with 0-2 $R^{12}$;

a C$_5$–C$_{14}$ carbocyclic residue substituted with 0-3 $R^{12}$;

a 5- to 10-membered heterocyclic ring system containing 1 to 3 heteroatoms independently selected from oxygen, nitrogen or sulfur, said heterocyclic ring system being substituted with 0-3 $R^{12}$;

$R^{11a}$ is selected from the following:

hydrogen; keto; halogen; cyano; —CH$_2$NH$_2$; —NH$_2$; —NH(C$_1$–C$_3$ alkyl) ; —CO$_2$H; —OC(=O) (C$_1$–C$_3$ alkyl) ; —OH; —C(=O)NH$_2$; —SO$_2$NH$_2$; C$_1$–C$_4$ alkyl; C$_2$–C$_4$ alkenyl; C$_3$–C$_{10}$ cycloalkyl; C$_3$–C$_6$ cycloalkylmethyl; nitro; C$_1$–C$_4$ alkyl substituted with —NH$_2$; C$_1$–C$_4$ hydroxyalkyl; C$_{1-4}$ haloalkyl; C$_1$–C$_4$ alkoxycarbonyl; C$_1$–C$_4$ alkylcarbonyl; C$_1$–C$_4$ alkylcarbonylamino;

2-(1-morpholino)ethoxy; aryl-C$_1$–C$_3$ alkyl; a C$_5$–C$_{14}$ carbocyclic residue; a 5- to 10-membered heterocyclic ring system containing 1 to 3 heteroatoms independently selected from oxygen, nitrogen or sulfur, said heterocyclic ring system substituted with 0-3 $R^{12a}$;

$R^{12}$, when a substituent on carbon, is selected from the following:

phenyl; halogen; hydroxy; nitro; cyano; C$_1$–C$_4$ alkyl substituted with 0-2 OR$^{13}$; C$_3$–C$_6$ cycloalkyl; C$_3$–C$_6$ cycloalkylmethyl; C$_7$–C$_{10}$ arylalkyl; C$_1$–C$_4$ alkoxy;

32

—CO$_2$H; hydroxamic acid; hydrazide; boronic acid; sulfonamide; formyl; C$_3$–C$_6$ cycloalkoxy; —OR$^{13}$; —NR$^{13}$R$^{14}$; C$_1$–C$_4$ alkyl substituted with —NR$^{13}$R$^{14}$; C$_{1-6}$ alkoxy C$_{1-6}$ alkyl substituted with 0 or 1 —Si(CH$_3$)$_3$; C$_1$–C$_4$ hydroxyalkyl; methylenedioxy; ethylenedioxy; C$_1$–C$_4$ haloalkyl; C$_1$–C$_4$ haloalkoxy; C$_1$–C$_4$ alkoxycarbonyl; C$_1$–C$_4$ alkylcarbonyloxy; C$_1$–C$_4$ alkylcarbonyl; C$_1$–C$_4$ alkylcarbonylamino; —S(O)$_m$R$^{13}$; —SO$_2$NR$^{13}$R$^{14}$; —NHSO$_2$R$^{14}$; —OCH$_2$CO$_2$R$^{13}$; 2-(1-morpholino)ethoxy; —C(R$^{14}$)=N(OR$^{13}$);

a 5- or 6-membered heterocyclic ring containing from 1 to 3 heteroatoms independently selected from oxygen, nitrogen or sulfur, the heterocyclic ring system being substituted with 0-3 $R^{12a}$;

a 3- or 4-carbon chain attached to adjacent carbons on the ring to which it is appended to form a fused 5- or 6-membered ring, said 5- or 6-membered ring being optionally substituted on any of the aliphatic carbons with halogen, C$_1$–C$_4$ alkyl, C$_1$–C$_4$ alkoxy, hydroxy, —NR$^{13}$R$^{14}$; or when $R^{12}$ is attached to a saturated carbon atom, it may be =O or =S, or when $R^{12}$ is attached to sulfur it may be =O;

$R^{12}$, when a substituent on nitrogen, is selected from the following:

phenyl; benzyl; phenethyl; hydroxy; C$_1$–C$_4$ hydroxyalkyl; C$_1$–C$_4$ alkoxy; C$_1$–C$_4$ alkyl; C$_3$–C$_6$ cycloalkyl; C$_3$–C$_6$ cycloalkylmethyl; —CH$_2$NR$^{13}$R$^{14}$; —NR$^{13}$R$^{14}$; C$_{1-6}$ alkoxy-C$_{1-6}$ alkyl; C$_1$–C$_4$ haloalkyl; C$_1$–C$_4$ alkoxycarbonyl; —CO$_2$H; C$_1$–C$_4$ alkylcarbonyloxy; C$_1$–C$_4$ alkylcarbonyl;

$R^{12a}$, when a substituent on carbon, is selected from one or more of the following:

phenyl; benzyl; phenethyl; phenoxy; benzyloxy; halogen; hydroxy; nitro; cyano; C$_1$–C$_4$ alkyl; C$_3$–C$_6$ cycloalkyl; C$_3$–C$_6$ cycloalkylmethyl; C$_7$–C$_{10}$ arylalkyl; C$_1$–C$_4$ alkoxy; —CO$_2$H; formyl; C$_3$–C$_6$ cycloalkoxy; —OH$^{13}$; C$_1$–C$_4$ alkyl substituted with —NH$_2$ or —NHMe; C$_{1-6}$ alkoxy-C$_{1-6}$ alkyl optionally substituted with —Si(CH$_3$)$_3$; C$_1$–C$_4$ hydroxyalkyl; C$_1$–C$_4$ haloalkyl; C$_1$–C$_4$ haloalkoxy; C$_1$–C$_4$ alkoxycarbonyl; C$_1$–C$_4$ alkylcarbonyloxy; C$_1$–C$_4$ alkylcarbonyl; C$_1$–C$_4$ alkylcarbonylamino; —S(O)$_m$Me; —SO$_2$NH$_2$; —NHSO$_2$Me; —OCH$_2$CO$_2$R$^{13}$; or 2-(1-morpholino)ethoxy;

$R^{12a}$, when a substituent on nitrogen, is selected from the following:

phenyl; benzyl; phenethyl; hydroxy; C$_1$–C$_4$ hydroxyalkyl; C$_1$–C$_4$ alkoxy; C$_1$–C$_4$ alkyl; C$_3$–C$_6$ cycloalkyl; C$_3$–C$_6$ cycloalkylmethyl; C$_1$–C$_4$ haloalkyl; C$_1$–C$_4$ alkoxycarbonyl; or C$_1$–C$_4$ alkylcarbonyl;

$R^{13}$ is selected from the following:

phenyl substituted with 0-3 $R^{11a}$;

benzyl substituted with 0-3 $R^{11a}$;

C$_1$–C$_6$ alkyl substituted with 0-3 $R^{11a}$;

C$_2$–C$_4$ alkenyl substituted with 0-3 $R^{11a}$;

C$_1$–C$_6$ alkylcarbonyl substituted with 0-3 $R^{11a}$;

C$_1$–C$_6$ alkoxycarbonyl substituted with 0-3 $R^{11a}$;

C$_1$–C$_6$ alkylaminocarbonyl substituted with 0-3 $R^{11a}$;

an amine protecting group when $R^{13}$ is bonded to N;

a hydroxy protecting group when $R^{13}$ is bonded to O; or, a 5- to 10-membered heterocyclic ring system containing 1 to 3 heteroatoms independently selected from oxygen, nitrogen or sulfur, the heterocyclic ring system being substituted with 0-3 $R^{12a}$;

$R^{14}$ is selected from the following:

hydrogen; hydroxy; C$_1$–C$_6$ alkoxy; NH$_2$; —NH(C$_1$–C$_4$ alkyl); C$_2$–C$_6$ alkenyl; phenyl; benzyl; an amine protecting group when $R^{14}$ is bonded to N; or C$_1$–C$_6$ alkyl substituted with 0–3 groups selected from OH, $C_1$–$C_4$ alkoxy, halogen, $NH_2$;

$R^{13}$ and $R^{14}$, when attached to the same N atom, can alternatively join to form: —$(CH_2)_4$—; —$(CH_2)_5$—; —$CH_2CH_2N(R^{15})CH_2CH_2$—; or —$CH_2CH_2OCH_2CH_2$—;

$R^{15}$ is: hydrogen or methyl;

$R^{20}$ is selected from the following:
hydrogen;
$C_1$–$C_6$ alkyl substituted with 0–3 $R^{11}$;
$C_3$–$C_6$ alkoxyalkyl substituted with 0–3 $R^{11}$;
$C_1$–$C_6$ alkylcarbonyl substituted with 0–3 $R^{11}$;
$C_1$–$C_6$ alkoxycarbonyl substituted with 0–3 $R^{11}$;
$C_1$–$C_6$ alkylaminocarbonyl substituted with 0–3 $R^{11}$;
benzoyl substituted with 0–3 $R^{12}$;
phenoxycarbonyl substituted with 0–3 $R^{12}$;
phenylaminocarbonyl substituted with 0–3 $R^{12}$; or
any group that, when administered to a mammalian subject, cleaves to form a free hydroxyl, amino or sulfhydryl;

m is 0, 1 or 2;

T is selected from:
—$N(R^{22})C(=Z)N(R^{23})$—;
—$N(R^{22})S(=Z')N(R^{23})$
—$N(R^{22})S(=Z')_2N(R^{23})$—; or
—$N(R^{22})P(=O)(R^{24a})N(R^{23})$—;

Z is O, S, $NR^{24}$;

Z' is O or $NR^{24}$;

$R^{22}$ and $R^{23}$ are independently selected from the following:
—$OR^{22a}$; —$N(R^{22a})(R^{22b})$;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$;
a 5- to 10-membered heterocyclic ring system containing 1 to 3 heteroatoms independently selected from oxygen, nitrogen or sulfur, said heterocyclic ring system being substituted with 0–2 $R^{32}$;

$R^{23}$ can also be hydrogen;

$R^{22a}$ and $R^{22b}$ are independently selected from the following:
hydrogen;
$C_1$–$C_8$ alkyl substituted with 0–3 $R^{31}$;
$C_2$–$C_8$ alkenyl substituted with 0–3 $R^{31}$;
$C_2$–$C_8$ alkynyl substituted with 0–3 $R^{31}$;
a $C_3$–$C_{14}$ carbocyclic ring system substituted with 0–5 $R^{31}$ or $R^{32}$; or
a 5- to 10-membered heterocyclic ring system containing 1 to 3 heteroatoms independently selected from oxygen, nitrogen or sulfur, said heterocyclic ring system being substituted with 0–2 $R^{32}$;

$R^{24}$ is selected from the following:
hydrogen; hydroxy; amino; $C_1$–$C_4$ alkyl; $C_1$–$C_4$ alkoxy; mono-($C_1$–$C_6$ alkyl)amino; di-($C_1$–$C_6$ alkyl)amino; cyano; nitro; benzyloxy; or —$NHSO_2$aryl, aryl being substituted with 0–1 ($C_1$–$C_6$)alkyl;

$R^{24a}$ is selected from the following:
hydroxy; amino; $C_1$–$C_4$ alkyl; $C_1$–$C_4$ alkoxy; mono-($C_1$–$C_6$ alkyl)amino; di-($C_1$–$C_6$ alkyl)amino; benzyloxy; or phenoxy;

$R^{31}$ is selected from the following:
halogen; cyano; —$CH_2NR^{13}R^{14}$; —$NR^{13}R^{14}$; —$CO_2R^{13}$; —$OC(=O)R^{13}$; —$OR^{13}$; —$S(O)_mR^{13}$; —$NHC(=NH)NHR^{13}$; —$C(=NH)NHR^{13}$; —$C(=O)NR^{13}R^{14}$; —$C(=NOR^{11})NR^{13}R^{14}$; —$NR^{14}C(=O)R^{13}$; =$NOR^{14}$; —$NR^{14}C(=O)OR^{14}$; —$OC(=O)NR^{13}R^{14}$; —$NR^{13}C(=S)NR^{13}R^{14}$; —$NR^{14}SO_2NR^{13}R^{14}$; —$NR^{14}SO_2R^{13}$; $SO_2NR^{13}R^{14}$; $C_2$–$C_4$ alkenyl; $C_3$–$C_{10}$ cycloalkyl; $C_3$–$C_6$ cycloalkylmethyl; benzyl; phenethyl; benzyloxy; nitro; $C_7$–$C_{10}$ arylalkyl; hydroxamic acid; hydrazide; oxime; boronic acid; sulfonamide; formyl; $C_3$–$C_6$ cycloalkoxy; $C_1$–$C_4$ alkyl substituted with —$NR^{13}R^{14}$; $C_1$–$C_4$ hydroxyalkyl; methylenedioxy; ethylenedioxy; $C_1$–$C_4$ haloalkyl; $C_1$–$C_4$ haloalkoxy; —$OCH_2CO_2R^{13}$; 2-(1-morpholino)ethoxy; azido; —$C(R^{14})=N(OR^{14})$; 1–3 amino acids, linked together via amide bonds, said amino acid being linked via the amine or carboxylate terminus; a $C_5$–$C_{14}$ carbocyclic residue substituted with 0–5 $R^{32}$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{32}$, when a substituent on carbon, is independently:
phenyl; phenethyl; phenoxy; $C_3$–$C_{10}$ cycloalkyl; $C_3$–$C_6$ cycloalkylmethyl; $C_7$–$C_{10}$ arylalkyl; hydrazide; hydroxamic acid; boronic acid; oxime; $C_{1-6}$ alkoxy-$C_{1-6}$ alkyl; methylenedioxy; ethylenedioxy; $C_1$–$C_4$ alkylcarbonyloxy; —$NHSO_2R^{14}$; phenylmethoxy; halogen; 2-(1-morpholino)ethoxy; —$CO_2R^{13}$; —$CONR^{13}NR^{13}R^{14}$; cyano; —CHO; $C_3$–$C_6$ cycloalkoxy; —$NR^{13}R^{14}$; —$C(R^{14})=N(OR^{14})$; $NO_2$; —$OR^{13}$; —$NR^{40}R^{41}$; —$SO_mR^{13}$; —$SO_mNR^{13}R^{14}$; $NR^{14}(C=O)R^{11}$; —$C(=O)NR^{11}R^{14}$; —$C(=O)NR^{13}R^{14}$; —$OC(=O)NR^{13}R^{14}$; —$C(=O)R^{11}$; —$OC(=O)R^{11}$; —$OCO_2R^{13}$; phenyl; —$C(=O)NR^{13}$-($C_1$–$C_4$ alkyl)-$NR^{13}R^{14}$; —$C(=O)NR^{40}R^{41}$; $C_1$–$C_4$ haloalkyl; $C_1$–$C_4$ haloalkoxy; $C_2$–$C_4$ haloalkenyl; $C_1$–$C_4$ haloalkynyl; —$C(=O)NR^{13}C(R^{11})_2NR^{13}R^{14}$;
—$C(=O)NR^{13}C(R^{11})_2NR^{13}NR^{14}$; —$C(=O)NR^{13}C(R^{11})_2NR^{13}CO_2R^{13}$; —$C(=O)NR^{13}$—($C_1$–$C_4$ alkyl)-$NR^{13}CO_2R^{13}$; —$C(=O)N(R^{13})$-($C_1$–$C_4$ alkyl)-$R^{11}$; —$C(=O)C(R^{11})_2NR^{13}R^{14}$; —$C(=O)C(R^{11})_2NR^{13}NR^{14}$; —$C(=O)C(R^{11})_2NR^{13}CO_2R^{13}$; —$C(=O)$-($C_1$–$C_4$ alkyl)-$NR^{13}R^{14}$; —$C(=O)$—($C_1$–$C_4$ alkyl)-$NR^{13}CO_2R^{13}$;

$C_1$–$C_4$ alkoxy substituted with 0–4 groups selected from: $R^{11}$, $C_3$–$C_6$ cycloalkyl, —$CO_2R^{13}$, —$C(=O)NR^{13}R^{14}$, —$NR^{13}R^{14}$ or OH; $C_1$–$C_4$ alkyl substituted with 0–4 groups selected from: $R^{11}$, =$NR^{14}$, =$NNR^{13}C(=O)NR^{13}R^{14}$ =$NNR^{13}C(=O)OR^{13}$, or —$NR^{13}R^{14}$;
$C_2$–$C_4$ alkenyl substituted with 0–4 $R^{11}$;
$C_2$–$C_4$ alkynyl substituted with 0–4 $R^{11}$;
a 5- to 10-membered heterocyclic ring containing from 1 to 3 heteroatoms independently selected from oxygen, nitrogen or sulfur, said heterocyclic ring being substituted with 0–2 $R^{12}$; and,
a 3- or 4-carbon chain, wherein 0, 1 or 2 of the carbon atoms are replaced with a heteroatom independently selected from oxygen, nitrogen or sulfur, attached to an adjacent carbon on the ring to which it is appended to form a fused 5- or 6-membered ring, said 5- or 6-membered ring being substituted on the aliphatic carbons with 0–3 halogen, $C_1$–$C_4$ alkyl, $C_1$–$C_4$ alkoxy, hydroxy, —$NR^{13}R^{14}$;
when $R^{32}$ is attached to a saturated carbon atom, it may be =O =S or =NOH; or when $R^{32}$ is attached to sulfur it may be =O;

$R^{32}$, when a substituent on nitrogen, is independently:
phenyl; benzyl; phenethyl; hydroxy; $C_1$–$C_4$ hydroxyalkyl; $C_1$–$C_4$ alkoxy; $C_1$–$C_4$ alkyl; $C_3$–$C_6$ cycloalkyl; $C_3$–$C_6$ cycloalkylmethyl; —$CH_2N^{13}R^{14}$; —$NR^{13}R^{14}$; $C_{1-6}$ alkoxy-$C_{1-6}$ alkyl; $C_1$–$C_4$ haloalkyl; $C_1$–$C_4$ alkoxycarbonyl; —CO₂H; C₁–C₄ alkylcarbonyloxy; C₁–C₄ alkylcarbonyl; —C(R¹⁴)=N(OR¹⁴);

R⁴⁰ is hydrogen or C₁–C₃ alkyl;

R⁴¹ is selected from —C(=O)NR¹³R¹⁴; —C(=O)NR¹³NR¹³R¹⁴; —C(=O)C(R¹¹)₂NR¹³R¹⁴; —C(=O)C(R¹¹)₂NR¹³NR¹³R¹⁴; —C(=O)C(R¹¹)₂NR¹³CO₂R¹³; —C(=O)H; —C(=O) R¹¹; —C(=O)-(C₁–C₄ alkyl)-NR¹³R¹⁴; —C(=O)-(C₁₋₄ alkyl)-NR¹³CO₂R¹³; or 1–3 amino acids linked together via amides bonds, and linked to the N atom via the carboxylate terminus.

[14] In another more preferred embodiment, the present invention provides novel compounds of formula (IId) or pharmaceutically acceptable salt or prodrug forms thereof, wherein:

T is —N(R²²)C(=O)N(R²³)—

R is O, NH, NOH, N(O)CH₃, NCH₂CH₂OH, or S(O)ₘ;

m is 0, 1, or 2;

R⁴ and R⁷ are independently C₁₋₄ alkyl substituted with 0–2 R¹¹;

R¹¹ is phenyl;

R²² and R²³ are independently C₁₋₂ alkyl substituted with 0–1 R³¹; and,

R³¹ is phenyl or C₃₋₅ cycloalkyl.

[15] In a second embodiment, the present invention provides novel compounds, or a pharmaceutically acceptable salt or prodrug forms thereof, selected from the following formulae:

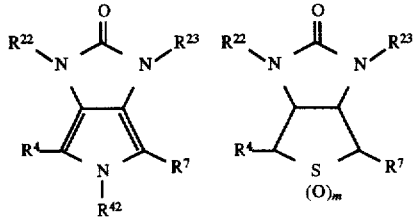

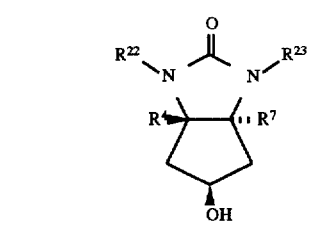

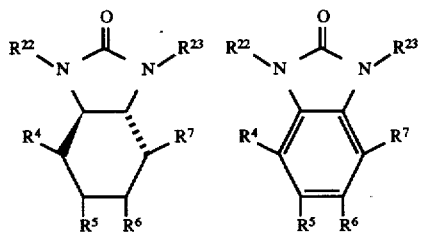

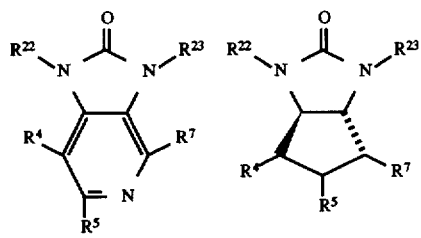

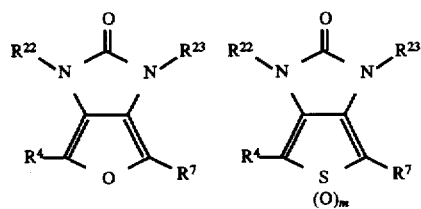

wherein:

R⁴ and R⁷ are independently selected from the following: hydrogen,

C₁–C₃ alkyl substituted with 0–1 R¹¹

R⁵ is hydrogen or —OR²⁰;

R⁶ is hydrogen or —OR²¹;

R²⁰ and R²¹ are independently hydrogen or any group that, when administered to a mammalian subject, cleaves to form a free hydroxyl;

R¹¹ is independently selected from the following: H, halogen; —OR¹³;

C₃–C₁₀ cycloalkyl substituted with 0–2 R¹²;

C₁–C₄ alkyl substituted with 0–2 R¹²;

aryl-C₁–C₃ alkyl substituted with 0–2 R¹²;

aryl substituted with 0–2 R¹²; or a heterocyclic ring system selected from pyridyl, pyrimidinyl, triazinyl, furanyl, thienyl, pyrrolyl, pyrazolyl, imidazolyl, tetrazoyl, benzofuranyl, indolyl, quinolinyl, isoquinolinyl, oxazolidinyl, said heterocyclic ring system being substituted with 0–2 R¹²;

R¹², when a substituent on carbon, is independently selected from the following:

benzyloxy, halogen, methyl, C₁–C₄ alkoxy, CF₃, 2-(1-morpholino)ethoxy, —CO₂H, hydroxamic acid, hydrazide, —C(R¹⁴)=N(OR¹³), cyano, boronic acid, sulfonamide, formyl, C₃–C₆ cycloalkoxy, C₁–C₄ alkyl substituted with —NR¹³R¹⁴, —NR¹³R¹⁴, hydroxy, hydroxymethyl;

R¹², when a substituent on nitrogen, is methyl;

R¹³ is independently selected from the following: hydrogen; C₁–C₄ alkyl; C₂–C₄ alkenyl; benzyl; or a heterocyclic ring system selected from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring system being substituted with 0–2 R¹²;

R¹⁴ is independently selected from the following: hydrogen, hydroxy, CF₃, C₁–C₄ alkyl, C₁–C₄ alkoxy, NH₂, C₂–C₄ alkenyl, or benzyl;

R¹³ and R¹⁴ can alternatively join to form —(CH₂)₄—, —(CH₂)₅—, —CH₂CH₂N(R¹⁵)CH₂CH₂—, or —CH₂CH₂OCH₂CH₂—;

R¹⁵ is hydrogen or methyl;

R²² and R²³ are independently selected from the following:

hydrogen, $C_1$–$C_8$ alkyl substituted with 0–3 $R^{31}$, $C_2$–$C_6$ alkenyl substituted with 0–3 $R^{31}$, $C_2$–$C_4$ alkynyl substituted with 0–3 $R^{31}$;

$R^{31}$ is selected from the following: halogen, —$OR^{13}$, $C_1$–$C_4$ alkyl, $C_3$–$C_{10}$ cycloalkyl, —$C(R^{14})$=$N(OR^{14})$, —$CO_2R^{13}$, —$S(O)_mR^{13}$, aryl substituted with 0–5 $R^{32}$, or a heterocyclic ring system chosen from pyridyl, pyrimidinyl, triazinyl, furanyl, thienyl, pyrrolyl, pyrazolyl, imidazolyl, tetrazolyl, benzofuranyl, indolyl, quinolinyl, isoquinolinyl, oxazolidinyl, said heterocyclic ring being substituted with 0–2 $R^{32}$;

$R^{32}$, when a substituent on carbon, is independently selected from the following:

benzyloxy, halogen, 2-(1-morpholino)ethoxy, —$CO_2R^{13}$, hydroxamic acid, —$CONR^{13}NR^{13}R^{14}$, cyano, boronic acid, sulfonamide, —CHO, $C_3$–$C_6$ cycloalkoxy, —$NR^{13}R^{14}$, —$C(R^{14})$=$N(OR^{13})$, $NO_2$, —$OR^{13}$, $NR^{40}R^{41}$, —$SO_mR^{13}$, —$SO_mNR^{13}R^{14}$, —C(=O) $NR^{13}R^{14}$, —$NHC(=O)R^{11}$, —$OC(=O)NR^{13}R^{14}$, —$C(=O)R^{11}$, —$OC(=O)R^{11}$, —$OCO_2R^{13}$, phenyl, —$C(=O)NR^{13}$—($C_1$–$C_4$ alkyl)-$NR^{13}R^{14}$, —C(=O) $NR^{40}R^{41}$, $C_1$–$C_4$ haloalkyl, $C_1$–$C_4$ haloalkoxy, $C_2$–$C_4$ haloalkenyl, $C_1$–$C_4$ haloalkynyl, —$C(=O)C(R^{11})_2$ $NR^{13}R^{14}$, —$C(=O)C(R^{11})_2NR^{13}NR^{13}R^{14}$, —$C(=O)C$ $(R^{11})_2NR^{13}CO_2R^{13}$; —C(=O)-($C_1$–$C_4$ alkyl)-$NR^{13}R^{14}$; —C(=O)-($C_1$–$C_4$ alkyl)-$NR^{13}CO_2R^{13}$; $C_1$–$C_4$ alkoxy substituted with 0–3 groups selected from: $R^{11}$, $C_3$–$C_6$ cycloalkyl, —$C(=O)NR^{13}R^{14}$, —$NR^{13}R^{14}$ or OH, $C_1$–$C_4$ alkyl substituted with 0–3 groups selected from: $R^{11}$, =$NR^{14}$, =$NNR^{13}C(=O)NR^{13}R^{14}$ or —$NR^{13}R^{14}$, $C_2$–$C_4$ alkenyl substituted with 0–3 $R^{11}$, $C_2$–$C_4$ alkynyl substituted with 0–3 $R^{11}$, a 5- or 6-membered heterocyclic ring containing from 1 to 3 heteroatoms independently selected from oxygen, nitrogen or sulfur;

$R^{32}$, when a substituent on nitrogen, is methyl;

m is 0, 1, or 2;

$R^{40}$ is hydrogen or $C_1$–$C_3$ alkyl;

$R^{41}$ is —$C(=O)NR^{13}R^{14}$, —$C(=O)NR^{13}NR^{13}R^{14}$, —$C(=O)C(R^{11})_2NR^{13}R^{14}$, —$C(=O)C(R^{11})_2$ $NR^{13}R^{14}$, —$C(=O)C(R^{11})_2NR^{13}CO_2R^{13}$, —C(=O) H, —$C(=O)R^{11}$, —C(=O)-($C_1$–$C_4$ alkyl)-$NR^{13}R^{14}$, —C(=O)-($C_1$–$C_4$ alkyl)-$NR^{13}CO_2R^{13}$, or 1–3 amino acids linked together via amide bonds, and linked to the N atom via the carboxylate terminus; and, $R^{42}$ is H, OH, $C_1$–$C_4$ alkoxy, benzyloxy, hydrogen or $C_1$–$C_3$ alkyl.

[16] In a third embodiment, the present invention provides novel pharmaceutical compositions comprising a pharmaceutically acceptable carrier and a therapeutically effective amount of a compound of formula (I) or a pharmaceutically acceptable salt or prodrug form thereof.

[17] In a fourth embodiment, the present invention provides a novel method for treating viral infections which comprises administering to a host in need of such treatment a therapeutically effective amount of a compound of formula (I) or a pharmaceutically acceptable salt or prodrug form thereof.

In a fifth embodiment, the present invention provides novel standards and reagents for determining the ability of a potential pharmaceutical to inhibit viral replication and/or HIV protease. These could be provided in a commercial kit comprising a compound provided by this invention and, optionally, a carrier. By using a compound of formula (I) as a standard or reagent in an in vitro or in vivo assay one of ordinary skill in the art would be able to determine is an assay was being run properly, compare a known activity with an unknown activity (e.g., for developing structure activity relationships) and/or determine if test samples (e.g., blood) were contaminated.

DEFINITIONS

As used herein, the following terms and expressions have the indicated meanings.

"Alkenyl" is intended to include hydrocarbon chains of either a straight or branched configuration having one or more carbon-carbon double bonds which may occur at any point along the chain that results in a stable structure, examples of which include, but are not limited to, ethenyl, propenyl, butenyl and the like.

"Alkoxy" is intended to include a straight or branched-chain alkyl group of an indicated number of carbon atoms attached through an oxygen bridge to the residue of the compound at the designated location, examples of which include, but are not limited to, methoxy, ethoxy, propoxy and butoxy.

"Alkoxycarbonyl" is intended to include an alkoxy group of an indicated number of carbon atoms attached through its oxygen atom to a carbonyl bridge, where the bridge is attached to the residue of the compound at the designated location, examples of which include, but are not limited to, methoxycarbonyl, ethoxycarbonyl, propoxycarbonyl and butoxycarbonyl.

"Alkyl" is intended to include both branched and straight-chain saturated aliphatic hydrocarbon groups having the specified number of carbon atoms, examples of which include, but are not limited to, methyl, ethyl, propyl, butyl, pentyl and hexyl.

"Alkylcarbonyl" is intended to include an alkyl group of an indicated number of carbon atoms attached through a carbonyl group to the residue of the compound at the designated location, examples of which include, but are not limited to, methyl carbonyl, ethyl carbonyl, propyl carbonyl and butyl carbonyl.

"Alkylcarbonylamino" is intended to include an alkyl group of an indicated number of carbon atoms attached through a carbonyl group to an amino bridge, where the bridge is attached to the residue of the compound at the designated location, examples of which include, but are not limited to, acetyl amino, ethyl carbonyl amino, propyl carbonyl amino and butyl carbonyl amino.

"Alkylcarbonyloxy" is intended to include an alkyl group of an indicated number of carbon atoms attached to a carbonyl group, where the carbonyl group is attached through an oxygen atom to the residue of the compound at the designated location, examples of which include, but are not limited to, methyl carboxy, ethyl carboxy, propyl carboxy and butyl carboxy.

"Alkynyl" is intended to include hydrocarbon chains of either a straight or branched configuration having one or more carbon-carbon triple bonds which may occur at any point along the chain that results in a stable structure, examples of which include, but are not limited to, ethynyl and propynyl.

"Amine protecting group" is intended to include any group known in the art of organic synthesis for the protection of amine groups. Such amine protecting groups include those listed in Greene et al. *Protective Groups in Organic Synthesis*; John Wiley & Sons: New York, 1991 and *The*

*Peptides: Analysis, Synthesis, Biology*; Roberts et al. Eds.; Academic Press: New York, 1981; Vol. 3., the disclosures of which are hereby incorporated herein by reference. Examples of amine protecting groups include, but are not limited to, the following: (1) acyl types such as formyl, trifluoroacetyl, phthalyl, and p- toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane types such as trimethylsilane; and (7) thiol containing types such as phenylthiocarbonyl and dithiasuccinoyl.

"Amino acid" is intended to include an organic compound containing both a basic amino group and an acidic carboxyl group. Included within this term are natural amino acids, modified and unusual amino acids, and amino acids which are known to occur biologically in free or combined form but usually do not occur in proteins. Among the modified and unusual amino acids are those disclosed in, for example, *The Peptides: Analysis, Synthesis, Biology*; Roberts et al. Eds.; Academic Press: New York, 1983; Vol. 5, p 342, the disclosure of which is hereby incorporated herein by reference. Modified or unusual amino acids which can be used to practice the invention include, but are not limited to, D-amino acids, hydroxylysine, 4-hydroxyproline, an N-Cbz-protected amino acid, ornithine, 2,4-diaminobutyric acid, homoarginine, norleucine, N-methylaminobutyric acid, naphthylalanine, phenylglycine, β-phenylproline, tert-leucine, 4-aminocyclohexylalanine, N-met-hylnorleucine, 3,4-dehydroproline, N,N-dimethylaminoglycine, N-methylaminoglycine, 4-aminopiperidine-4-carboxylic acid, 6-aminocaproic acid, trans-4-(aminomethyl) cyclohexanecarboxylic acid, 2-, 3-, and 4-(aminomethyl) benzoic acid, 1-aminocyclopentanecarboxylic acid, 1-aminocyclopropanecarboxylic acid and 2-benzyl-5-aminopentanoic acid.

"Amino acid residue" is meant to indicate that portion of an amino acid (as defined herein) that is present in a peptide.

"Any group that, when administered to a mammalian subject as part of a compound of formula (I), cleaves to form a free hydroxyl, free amino or free sulfhydryl" is intended to include an OH, $NH_2$ or SH group wherein a hydrogen atom is replaced with a masking group such that the O—, NH—, or S-masking group combination, when administered to a mammalian subject, cleaves to form a compound having a free hydroxyl (OH), free amino ($NH_2$), or free sulfhydryl (SH) group, respectively. Examples of masking groups include, but are not limited to, $C_1$–$C_6$ alkyl substituted with 0–3 $R^{11}$, $C_3$–$C_6$ alkoxyalkyl substituted with 0–3 $R^{11}$, $C_1$–$C_6$ alkylcarbonyl substituted with 0–3 $R^{11}$, $C_1$–$C_6$ alkoxycarbonyl substituted with 0–3 $R^{11}$, $C_1$–$C_6$ alkylaminocarbonyl substituted with 0–3 $R^{11}$, benzoyl substituted with 0–3 $R^{12}$, phenoxycarbonyl substituted with 0–3 $R^{12}$, phenylaminocarbonyl substituted with 0–3 $R^{12}$, amine protecting groups, hydroxyl protecting groups and sulfhydryl protecting groups, where the masking group is subject to enzymatic cleavage or cleavage by other conditions present within the mammalian subject.

"Any group that, when administered to a mammalian subject as part of a compound of formula (I), cleaves to form a compound having two free hydroxyl groups, or two free amino groups, or one free hydroxyl and one free amino group", and "any group that, when administered to a mammalian subject as part of a compound of formula (I), cleaves to form a free hydroxyl" includes the O-masking group and NH-masking groups referred to above.

"Aryl" or "aromatic residue" is intended to include phenyl, naphthyl and biphenyl.

"$C_7$–$C_{10}$ arylalkyl" is intended to refer to an aryl group attached through a $C_1$–$C_4$ alkyl bridge to the residue of the indicated compound.

"($C_1$–$C_3$ alkyl)aryl" is intended to refer to a $C_1$–$C_3$ alkyl group which is attached through an aryl ring to the residue of the indicated compound.

"Aryl-$C_1$–$C_3$ alkyl" is intended to refer to an aryl group attached through a $C_1$–$C_3$ alkyl group to the residue of the indicated compound.

If a keto group "=O" is contained in the definition of a variable, then when the keto group is present both bonds are attached to the carbon the variable depends from and, if necessary, a hydrogen or other variable is not present in order to maintain a tetracoordinate carbon.

"Bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and the like.

"Carbocycle" or "carbocyclic residue" or "carbocyclic ring system" is intended to include any stable 3- to 7-membered monocyclic or bicyclic ring, or any stable 7- to 14-membered bicyclic or tricyclic ring, or any stable polycyclic carbon ring having up to 26 members, any ring of which may be saturated, partially unsaturated, or aromatic. Examples of such carbocycles include, but are not limited to, cyclopropyl, cyclobutyl, cyclopentyl, cyclohexyl, phenyl, biphenyl, naphthyl, indanyl, adamantyl, and tetrahydronaphthyl (tetralin).

"Counterion" is intended to include small, negatively charged species such as chloride, bromide, hydroxide, acetate, sulfate, and the like.

"Cycloalkoxy" is intended to include cycloalkyl groups of indicated carbon number attached through an oxygen bridge to the designated position.

"Cycloalkyl" is intended to include saturated ring groups, including mono-, bi-and poly-cyclic ring systems, such as cyclopropyl, cyclobutyl, cyclopentyl, cyclohexyl, cycloheptyl, cyclooctyl and adamantyl. "Cycloalkylmethyl" is intended to include cycloalkyl groups of indicated carbon number attached through a methylene group to the designated position.

"Haloalkyl" is intended to include both branched and straight-chain saturated aliphatic hydrocarbon groups having the specified number of carbon atoms, substituted with 1 or more halogen atoms. "Halo" or "halogen" is intended to include fluoro, chloro, bromo, and iodo.

"Heterocycle" is intended to include stable 5- to 7-membered monocyclic or bicyclic rings and stable 7- to 10-membered bicyclic rings where the heterocycle may be either saturated or unsaturated, and where the heterocycle comprises from 1 to 3 heteroatoms independently selected from the group consisting of N, O and S, wherein the nitrogen and sulfur heteroatoms may optionally be oxidized, and the nitrogen heteroatom may optionally be quaternized, including a bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on a carbon or nitrogen atom if the resulting compound is stable. Examples of such heterocycles include, but are not limited to, acridinyl, azocinyl, benzimidazolyl, benzofuranyl, benzothiophenyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindolinyl, isoindolyl, isoquinolinyl, isothiazolyl, isoxazolyl, morpholinyl, naphthyridinyl, octahydroisoquinolinyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, 4-piperidonyl, pteridinyl, purinyl, pyranyl, pyrazinyl, pyrazolidinyl, pyrazolinyl, pyrazolyl, pyridazinyl, pyridyl, pyridyl, pyridooxazole, pyridoimidazole, pyridothiazole, thienothiazole, thienooxazole, thienoimidazole, pyrimidinyl, pyrrolidinyl, pyrrolinyl, 2-pyrrolidonyl, pyrrolinyl, pyrrolyl, 2H-pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, thianthrenyl, thienyl, thiophenyl, triazinyl and xanthenyl. Also included are fused ring and spiro compounds containing, for example, the above heterocycles.

"Hydroxy" and "hydroxyl" are used interchangeably, and both are intended to include the "—OH" group.

"Hydroxy protecting group" is intended to include any group known in the art of organic synthesis for the protection of hydroxyl groups. Such hydroxy protecting groups include those listed in Greene et al. *Protective Groups in Organic Synthesis*; John Wiley & Sons: New York, 1991, the disclosure of which is hereby incorporated herein by reference. Examples of hydroxy protecting groups include, without limitation, acyl types, aromatic carbamate types and alkyl types. Exemplary hydroxy protecting groups include, without limitation, methyl, met-hoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl (SEM), tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

"Ketal group" or "ketal ring" is intended to include any ketal protecting group which can be hydrolyzed to form a carbonyl. Such ketal rings or ketal protecting groups are well known in the art of organic synthesis and typically include, for example, substituted or unsubstituted carbocyclic diethers, dithioethers, or mixed ethers. Such ketal protecting groups include those listed in Greene et al. *Protective Groups in Organic Synthesis*; John Wiley & Sons: New York, 1991.

"Peptide" is meant to include a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

"Peptide bond" means a covalent amide linkage formed by loss of a molecule of water upon the joining of the carboxyl group of a first amino acid and the amino group of a second amino acid.

"Pharmaceutically acceptable salt" is intended to include all derivatives of the subject compound wherein the compound is modified by formation of its acid or base salt. Examples of pharmaceutically acceptable salts include, but are not limited to, mineral or organic acid salts of basic residues such as amines. Examples of pharmaceutically acceptable salts also include, but are not limited to, alkali or organic salts of acidic residues such as carboxylic acids, and the like. Pharmaceutically acceptable salts of the compounds of the invention can be prepared, for example, by reacting the free acid or base forms of these compounds with stoichiometric amount of the appropriate base or acid in water or in an organic solvent, or in a mixture of the two. Nonaqueous media like ether, ethyl acetate, ethanol, isopropanol, or acetonitrile are preferred. Lists of suitable salts are found in *Remington's Pharmaceutical Sciences* 1985, 1418 (17th ed., Mack Publishing Company, Easton, Pa.,) the disclosure of which is hereby incorporated herein by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group(s), provided that the indicated atom's normal valency is not exceeded, and that the substitution results in a stable compound. When a substituent is keto (i.e., =O) group, then 2 hydrogens on the atom are replaced.

"Therapeutically effective amount" is intended to include an amount of a compound of the present invention effective to inhibit HIV infection or treat the symptoms of HIV infection in a host.

The compounds described herein may have asymmetric centers. All chiral, diastereomeric, and racemic forms of the compounds of formulas (I) through (XI), and of any other structural formulas present in Schemes 1 through 5 below, relating to the synthesis of the compounds, are intended. Compounds of the present invention containing an asymmetrically substituted atom may be isolated in optically active or racemic forms. It is well known in the art how to prepare optically active forms, such as by resolution of racemic forms or by synthesis from optically active starting materials.

The compounds described herein may have geometric isomers. All stable forms of geometric isomers of the compounds of formulas (I) through (XI), and of any other structural formulas present in Schemes 1 through 5 are intended. Geometric isomers include the geometric isomers of carbon-carbon double bonds, carbon-nitrogen double bonds, rings, and the like, including both cis and trans isomers. All chiral, diastereomeric, racemic forms and all geometric isomeric forms of a structure are intended, unless the specific stereochemistry or isomeric form is specifically indicated.

When any variable (e.g., $R^4$ through $R^{41}$, $R^{4a}$ through $R^{24a}$, etc.) occurs more than one time in any constituent or in formulas (I) through (XI), or in any other formula herein, its definition on each occurrence is independent of its definition at any other occurrence. Thus, for example, if a group is substituted with 0–3 $R^{11}$, then said group may optionally be substituted with up to three $R^{11}$, and $R^{11}$ at each occurrence is selected independently from the defined list of possible $R^1$1. Also, for example, in —$N(R^{20})_2$, each of the $R^{20}$ substituents may be independently selected from the list of possible $R^{20}$ groups defined. Also, combinations of substituents and/or variables are permissible only if such combinations result in stable compounds.

Compounds of the invention have the formula (I) where $R^4$, $R^{4a}$, $R^5$, $R^{5a}$, $R^6$, $R^{6a}$, $R^7$, $R^{7a}$, $R^8$, $R^{11}$, $R^{11a}$, $R^{12}$ when a substituent on either carbon or nitrogen, $R^{13}$, $R^{14}$, $R^{15}$, m, T, $R^{20}$, $R^{21}$, $R^{22}$, $R^{23}$, Z, $R^{24a}$, $R^{25}$, $R^{26}$, $R^{27}$, $R^{28}$, $R^{31}$, $R^{32}$ when a substituent on either carbon or nitrogen, $R^{40}$, $R^{41}$, and n are defined as provided in the preceding Summary of the Invention, with the proviso as also provided in the preceding Summary of the Invention. In addition to compounds of formula (I), compounds of the invention include pharmaceutically acceptable salt or prodrug forms thereof.

SYNTHESIS

The compounds of the present invention can be prepared in a number of ways well known - to one skilled in the art of organic synthesis. The compounds of the present invention can be synthesized using the methods described below, together with synthetic methods known in the art of synthetic organic chemistry, or variations thereon as appreciated by those skilled in the art. Preferred methods include but are not limited to those methods described below. Each of the references cited below are hereby incorporated herein by reference. All the temperatures are reported herein in degrees Celsius.

Compounds of the invention of the formula (Ia):

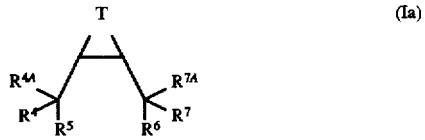

can be formed from diamines of formula (III):

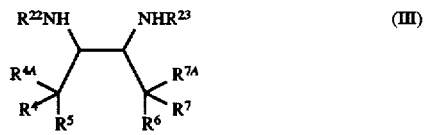

by cyclization with an appropriate cyclizing agent to give the corresponding cyclic urea, sulfinamide, sulfonamide, phosphoramide and cyanoguanidine compounds.

The diamines of formula (III) are either commercially available or can be synthesized either (a) from the corresponding diols using one of several procedures that are known to one skilled in the art for converting alcohols to amines (see for example, *Tet. Lett.* 1991, 32, 999; *Tetrahedron:. Asymmetry.* 1991, 2, 981; Synthesis 1990, 1023); or (b) using the methods described below. As outlined in Scheme 1, diamines (III) can be synthesized from amino acid amides (IV) by alkylation with an organometallic reagent, for example, an orgaomagnesium halide, to yield an amino ketone which upon reduction using standard methods known in the art gives the amino alcohol (V). The resulting alcohol can be converted to the desired diamine by displacement with azide ion and subsequent reduction using standard procedures well known to one skilled in the art of organic synthesis. Combined with the many procedures for making both natural and unnatural amino acids that are known to one skilled in the art, this route provides a wide variety of possible diamines.

The diamines of formula (III) can be cyclized with suitable cyclizing reagents of formula J-(C=Z)-J', where J and J' are leaving groups, in a suitable solvent, optionally in the presence of a base, thereby to form a compound of formula (I) wherein T is $R^{22}NC(=Z)NR^{23}$. For compounds of formula (I) wherein T is —$N(R^{22})C(=O)N(R^{23})$—, the suitable cyclizing reagent may be selected from, but is not limited to, phenyl chloroformate, phenyl tetrazoylformate, urea, phosgene, triphosgene, oxalyl chloride, N,N'-disuccinimidyl carbonate, 1,1'-carbonyldiimidazole, trichloromethyl chloroformate, and 2(S),3-pyridinediyl thiocarbonate. A preferred cyclizing reagent, when T is —$N(R^{22})C(=O)NR^{23}$—, is 1,1'-carbonyl diimidazole.

For compounds of formula (I) wherein T is —$N(R^{22})C(=S)N(R^{23})$—, the suitable cyclizing reagent may be selected from, but is not limited to, 1,1'-thiocarbonyl diimidazole or carbon disulfide. Preferably, the cyclizing reagent is 1,1'-thiocarbonyldiimidazole.

For compounds of formula I) wherein T is —$N(R^{22})S(=O)_2N(R^{23})$—, the suitable cyclizing reagent may be selected from, but is not limited to, sulfamide.

For compounds where T is —$N(R^{22})P(=O)(R^{24}—)N(R^{25})$—, the suitable applying agent may be selected from, but is not limited to phenydichlorophosphate.

A base may optionally be included in the above-described cyclizations in order to account for any acid-labile protecting groups that may be present. The base may be selected from organic bases which include, but are not limited to, pyridine, diisopropylethylamine, and triethylamine. The base may alternatively be selected from inorganic bases, such as, for example, sodium hydroxide.

Suitable solvents for the above cyclization include organic solvents or a biphasic suspension of water and an organic solvent. Suitable organic solvents include, but are not limited to, chloroform, methylene chloride, tetrachloroethane, butyl chloride, dichloroethane, tetrahydrofuran, N,N-dimethylformamide and toluene. Preferred solvents are toluene or chloroform.

As used herein, the term "hydroxyl protecting group" means any group known in the art of organic synthesis for the protection of hydroxyl groups. Such protecting groups include those listed in Greene and Wuts, "Protective Groups in Organic Synthesis", John Wiley & Sons, New York (1991), the disclosure of which is hereby incorporated by reference. The hydroxyl protecting groups are base-stable and can include, but are not limited to acyl types, aromatic carbamate types and alkyl types. Exemplary are methyl, methoxymethyl, methylthiomethyl, benzyloxymethyl, t-butoxymethyl, 2-methoxyethoxymethyl, 2,2,2-trichloroethoxymethyl, 2-(trimethylsilyl)ethoxymethyl, tetrahydropyranyl, tetrahydrofuranyl, t-butyl, triphenylmethyl, trimethylsilyl, triethylsilyl, t-butyldimethylsilyl, t-butyldiphenylsilyl, pivaloate or N-phenylcarbamate.

Another, preferred method to form compounds of formula (I), in cases wherein $R^{22}$ and $R^{23}$ are $CH_2R^{31}$, is to cyclize a compound of structure (III) where $R^{22}$ and $R^{23}$ are hydrogen, and to alkylate the resulting product at nitrogen using a base and an alkylating agent, optionally in the presence of a phase transfer catalyst, using methods well known in the art. The preferred base is sodium hydride, and the preferred alkylating agents are $R^{22}Y$ and $R^{23}Y$, wherein Y is a halogen, triflate, or mesylate, preferably a bromide or iodide. The details of the above preferred alkylation conditions have been described in detailed in European patent application WO93/07128. Cleavage of protecting groups, if employed, yields structures of formula (I).

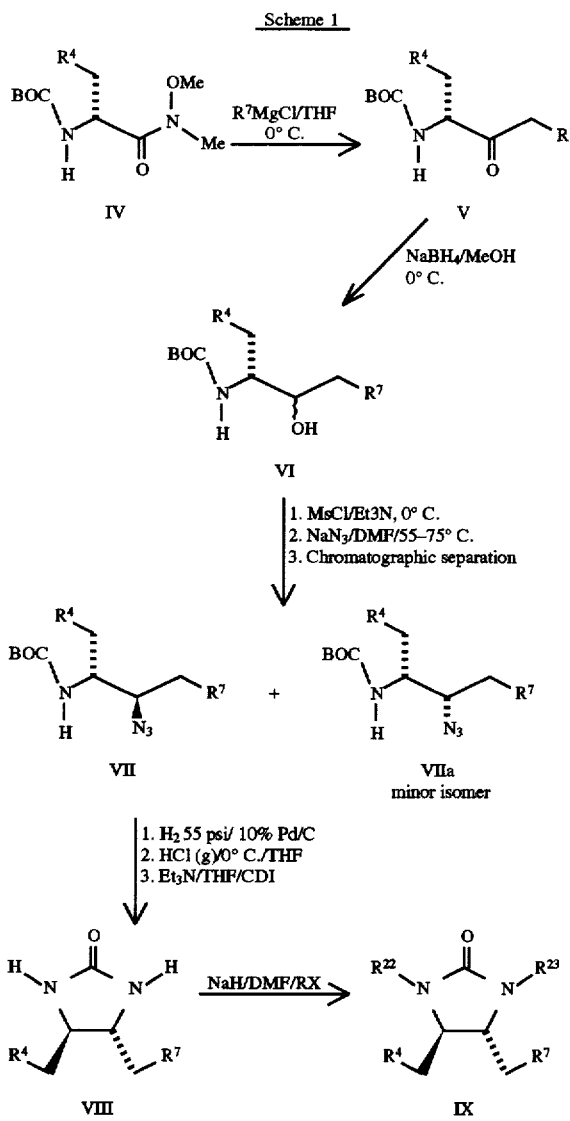

Alternately, diamines of formula III can be prepared from commercially-available 2,3-dibromosuccinic acid following the procedure described by Lavielle et al. (JACS 1978 100(5) 1558–1563). Displacement of bromine with an appropriate amine, such as, for example, benzylamine, gives the corresponding 2,3-bis(amino)succinic acid. Cyclization of the diamine with one of the cyclizing reagents described above gives a cyclic intermediate which is converted to a compound of formula I using procedures well known to one skilled in the art of organic synthesis. For example, as illustrations in Scheme 2, cyclization of diamine X with phosgene gives dicarboxyimidazolidinone XI. The carboxylic acid groups are then converted to N,O-dimethylhydroxyamides by treatment with 1,1-carbonyldiimidazole followed by N,O-dimethylhydroxylamine hydrochloride. Treatment of diamide XII with 2 equivalents of an organometallic reagent, for example, an organomagnesium halide, provides a diketone compound XIII. Further manipulation of the ketone functions using standard procedures for interconversion of functional groups gives additional compounds of formula I.

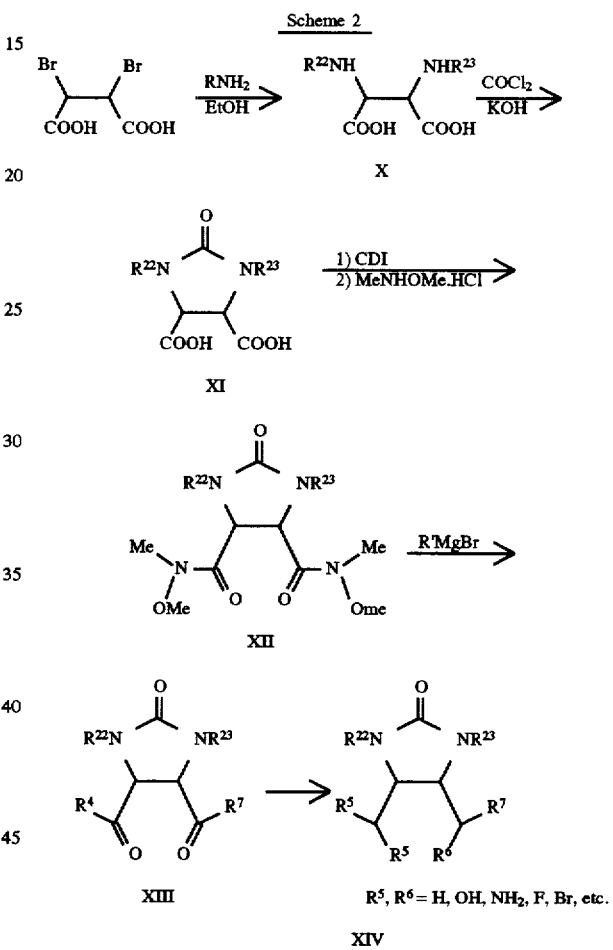

An alternate synthesis of diketone (XIII) is shown in Scheme 2a. Cyclization of dicyanoethylenediamine with phosgene followed by alkylation using conditions described above provides dinitrile XV. Reduction of the double bond and treatment with an appropriate organometallic reagent, i.e., an organomagnesium halide or organocadmium compound, gives diketone XIII.

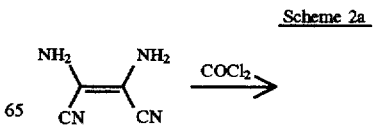

Scheme 2a

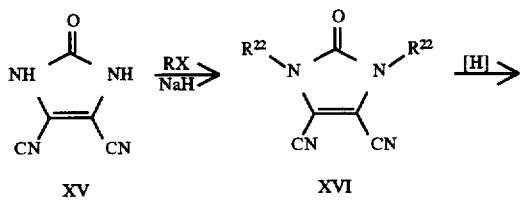

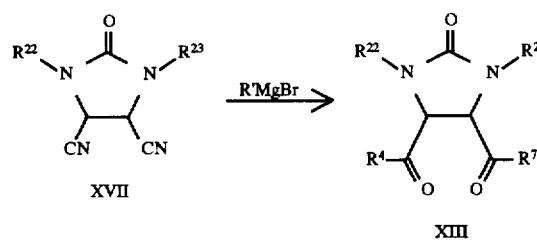

Alternately, the compounds of this invention may be synthesized by ring contraction of the corresponding 6- or 7-membered ring cyclic compounds XVIII and XIX. The 6- and 7-membered ring cyclic compounds are prepared according to the procedures described in European patent application W09307128. As outlined in Scheme 3 the 6-and 7-membered compounds can be converted to the corresponding fluoro-substituted 5-membered ring cyclic compounds of formula I by treatment with DAST or under Mitsunobu type conditions to give the hydroxy, bromo unsubstituted compounds of formula I XXI, XXIII, and IX respectively.

Scheme 3

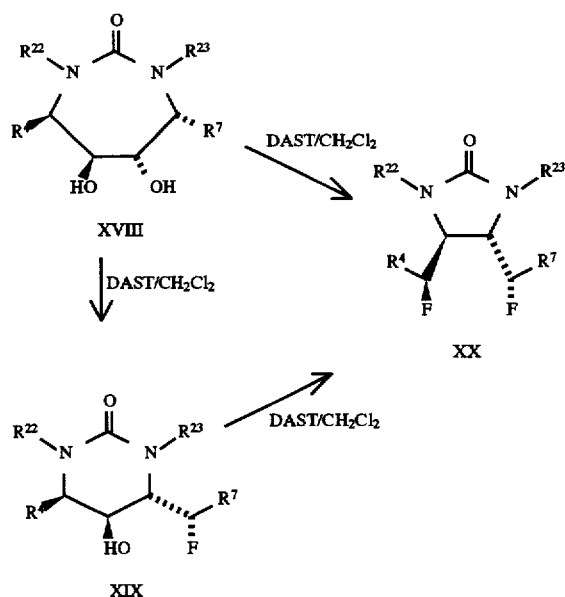

Scheme 3a

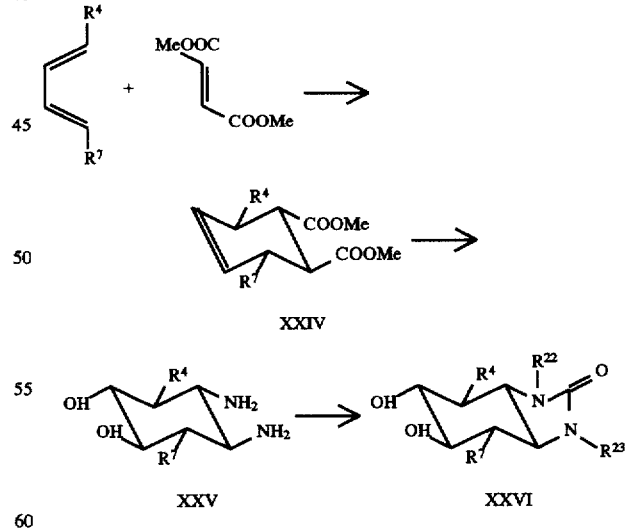

Compounds of formula I wherein $R^1$ and $R^2$ combine to form a 6-membered saturated carbocyclic ring can be prepared by utilizing a Diels-Alder cyclization to prepare the 6-membered ring. Diels-Alder condensation of the appropriately substituted diene and dienophile as depicted in Scheme 4 would provide a 4,5-dicarbomethoxycyclohexene system, XXIV. Conversion of the double bond to the trans diol (reference or reagents)!, hydrolysis of the diester and double Hofmann degradation would give the diamine XXV. Suitable protection of the diol, followed by cyclization and alkylation using procedures described above affords compounds of the invention of formula XXVI.

Scheme 4

Stereochemical control can be achieved via intramolecular cyclization as outlined in Scheme 4a. The synthesis of compound XVII is based on a procedure described by Ndibwami et al. (*Can. J. Chem.* 1993, 71, 695). The control of relative stereochemistry in the Diels-Alder cyclization can be achieved by judicious choice of cis/trans diene and trans dienophile. Catalysis with chiral Lewis acids can be used to control the absolute stereochemistry, if desired.

sulfonamide with CDI or sulfamide, respectively, followed by alkylation on nitrogen and deprotection of the diol provides XXXII.

Scheme 4a

XXVII

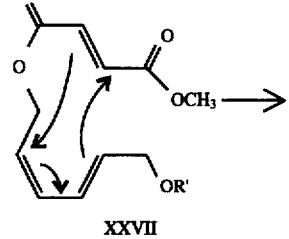

XXVIII → XXIX

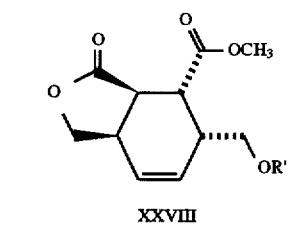

XXX

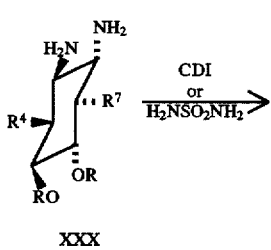

XXXI   XXXII

Compounds of formula I wherein $R^1$ and $R^2$ combine to form a 5-membered saturated carbocyclic ring can be prepared from an appropriately substituted cyclopentene compound via the series of steps outlined in Scheme 5. Treatment of a suitably protected 4-hydroxycyclohexene with osmium tetroxide gives a cis-diol, XXXIV. Oxidation of the diol to the diketone XXXV can be achieved by a number of methods known to one skilled in the art, for example, but not limited to, Swern oxidation (Manacuso & Swern, *Synthesis* 1981, 165) or Tempo oxidation (Leanna et al., *Tetrahedron Lett.*, 1992, 33, 5029). Conversion of the diketone to the bisoxime by treatment with hydroxylamine followed by alkylation with an apropriate organometallic reagent provides diamine XXVII. Cyclization to the cyclic urea or

Scheme 5

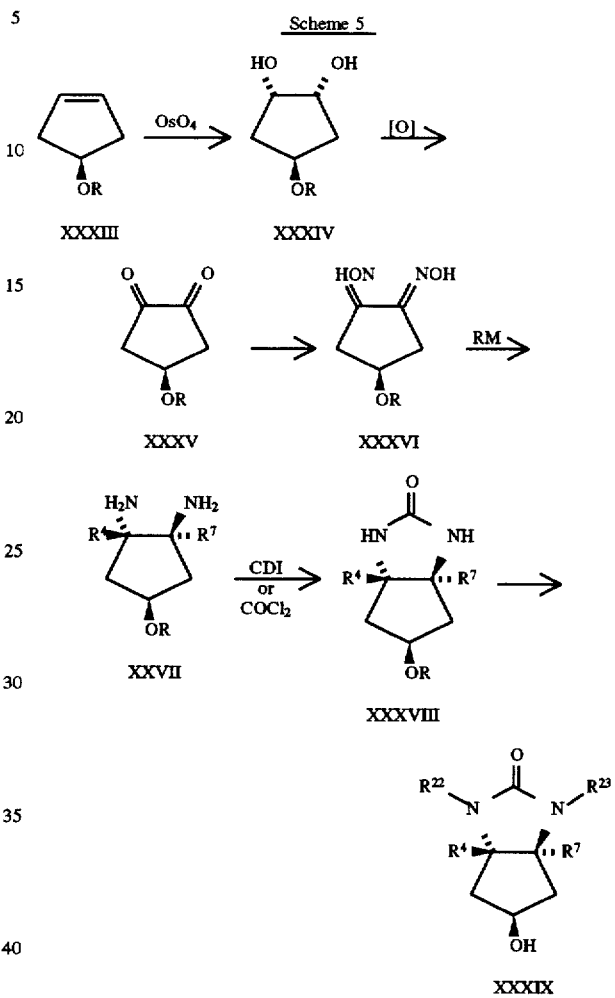

Compounds of formula I, wherein $R^1$ and $R^2$ are combined to form a six-membered aromatic carbocycle or heterocycle, can be prepared by cyclization of 1,2-phenylene diamines or the corresponding 1,2-diaminoheterocycles using the cyclization methods described above. Illustrative syntheses are depicted in schemes 6 and 6a.

Scheme 6

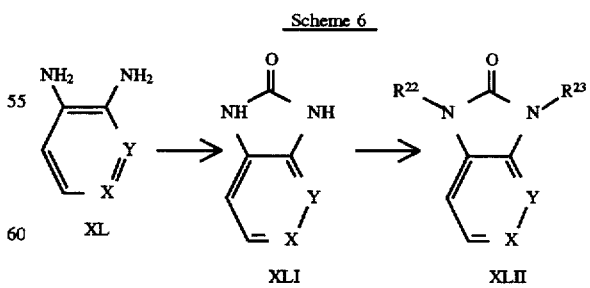

XL   XLI   XLII

Scheme 6 -continued

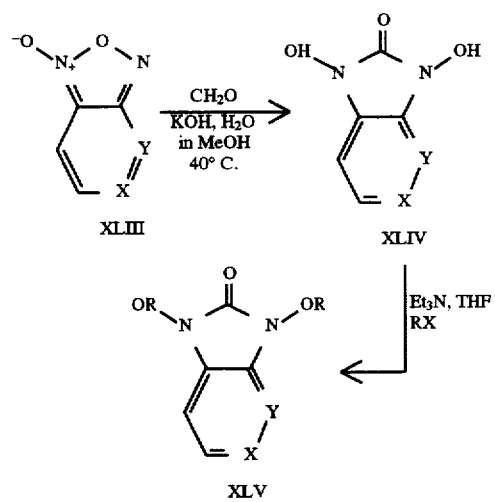

Compounds of formula I wherein T is —(R²²)NC(=O)N(R²³)— and R¹ and R² are combined to form a 5-membered sulfur containing heterocycle can be alkylation of biotin or derivatives thereof via the synthetic sequence depicted in Scheme 7. The resulting biotin derivative XLVII can be optionally oxidized to the corresponding sulfoxide XLVIII or sulfone XLIX using a variety of methods for oxidation of mercaptons well known in the art.

Scheme 8

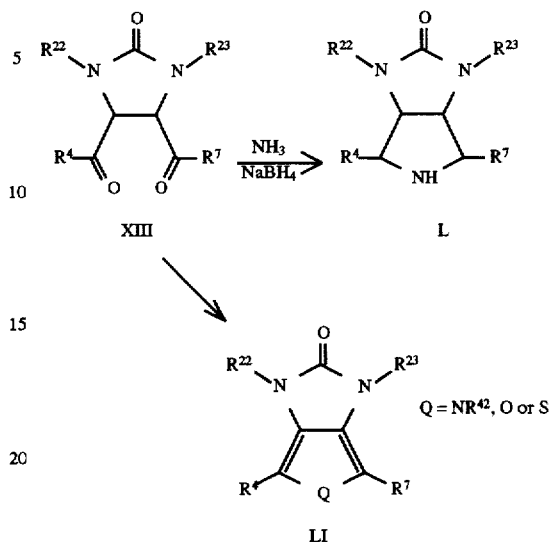

As illustrated in Scheme 9, treatment of diol XIVa with methanesulfonyl chloride provides a bismesylate which on treatment with sodium sulfide cyclizes to compound LII. Compounds of formula LII can be further converted to the corresponding sulfoxides, sulfones and sulfamoyl com-

Scheme 7

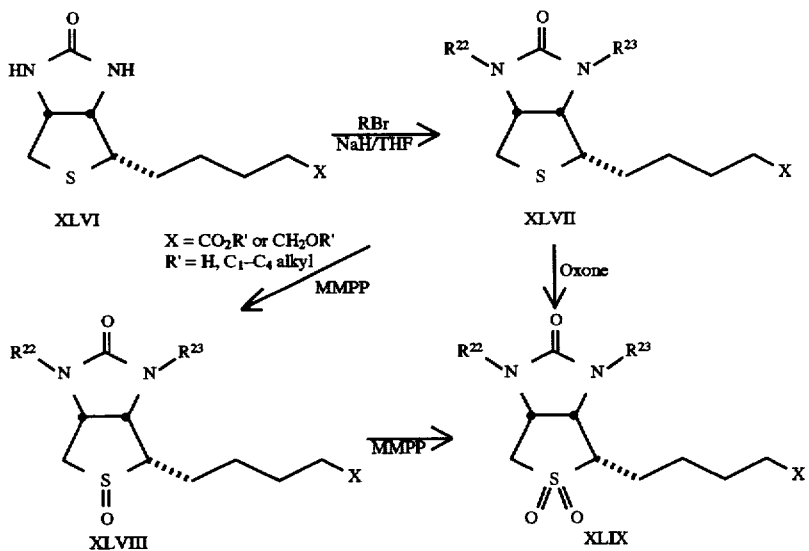

Reductive amination of diketone XIII will provide cyclic compounds of formula L. Alternately compounds wherein R¹ and R² are combined to form a 5-membered aromatic heterocycle can be prepared from diketone XIII by a modification of procedures described by R. Ramasseul and A. Rassat (Bull. Soc. Chim. Fr., 1970, No. 12, pp. 4330–4341).

pounds using standard methodology to give additional examples of the present invention.

Scheme 9

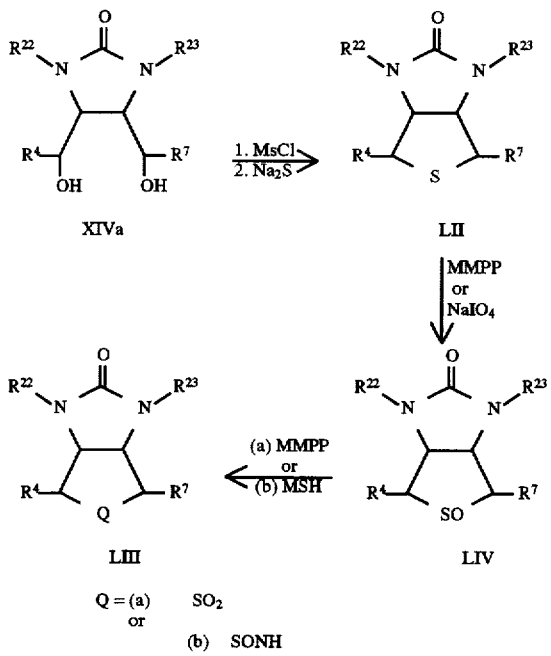

Q = (a) SO$_2$
or
(b) SONH

Other features of the invention will become apparent in the course of the following descriptions of exemplary embodiments which are given for illustration of the invention and are not intended to be limiting thereof.

EXAMPLES

The synthesis of representative compounds according to the invention is described in further detail below with reference to the following specific, but non-limiting examples.

Abbreviations used in the Examples are defined as follows: "°C." for degrees Celsius, "d" for doublet, "dd" for doublet of doublets, "DAST" for diethylaminosulfur trifluoride, "eq" for equivalent or equivalents, "g" for gram or grams, "mg" for milligram or milligrams, "mL" for milliliter or milliliters, "H" for hydrogen or hydrogens, "hr" for hour or hours, "m" for multiplet, "M" for molar, "min" for minute or minutes, "MHz" for megahertz, "MS" for mass spectroscopy, "nmr" or "NMR" for nuclear magnetic resonance spectroscopy, "t" for triplet, "TLC" for thin layer chromatography.

Example 1

(3S-trans)-1,3-bis[3-(phenylmethoxy)benzyl]-3,4,5-bis(1S-fluoro-2-phenylethyl)-2-imidazolidinone.

A solution of compound XVII, where $R^{22}=R^{23}=3$-benzyloxybenzyl and $R^4=R^7$=benzyl, (250 mg; 0.35 mmol) in methylene chloride was cooled to 0° C. in an ice bath and treated with DAST (0.13 mL; 1.04 mmol)). After stirring for a few minutes, analysis by TLC (silica gel 40% Ethyl acetate/hexane) showed no starting material remained. The mixture was quenched with sat'd NaHCO$_3$, the organic layer separated and washed with water and brine. The solution was dried over MgSO$_4$, and evaporated. The residue was chromatographed by HPLC on silica gel (40% Ethyl acetate/hexane) to give 110 mg of the title compound. MS m/z 723 (M+H)$^+$; HRMS Calc. for C$_{47}$H$_{45}$N$_2$O$_3$F$_2$: 723.339805; Found: 723.339825. NMR (CDCl$_3$) C2 symmetrical: δ 7.40–7.25 (m, 9H), 7.0–7.1 ( m, 5H), 5.1 (s, 2H), 5.05 (d, 15 Hz, 1H), 4.25 (d, 15 Hz, 1H), 4.7–4.5 (m) [total 1H, HF=50 Hz], 3.65 (t, 5.5 Hz, 1H), 2.8–2.4 (m, 2H).

Example 2

(3S-trans)-4,5-bis(1S-fluoro-2-phenylethyl)-1,3-bis[(3-hydroxyphenyl)methyl]-2-imidazolidinone A solution of the compound of Ex. 1 (110 mg, 0.15 mmol) in methanol was treated with 20 mg of 10% Pd/C and hydrogenated in a Parr aparatus for 24 hrs at 50 psi of H$_2$. The catalyst was filtered off through a pad of Celite, and the filtrate was concentrated. The residue was chromatographed on silica gel (50% ethyl acetate/hexane) to give 10 mg of the desired product. MS m/z 543 (M+H)$^+$ NMR (CDCl$_3$) C2 symmetrical: δ7.27–7.10 (m, 4H), 7.0 (s, 1H), 6.92 (d, 9 Hz, 2H), 6.78 (dd, 10 Hz, 1 Hz, 1H), 6.72 (d, 8 Hz, 1H), 6.65 (s, 1H), 4.72 (d, 15 Hz, 1H), 4.6–4.5 (m) [total 1H, HF=50 Hz], 4.15 (d, 15 Hz, 1H), 3.61 (t, 5.5 Hz, 1H) , 2.65–2.3 (m, 2H).

Example 3

(3S-trans)-1,3-bis(cyclopropylmethyl)-4,5-bis(1S-fluoro-2-phenylethyl)-2-imidazolidinone A solution of compound XIX, where $R^{22}=R^{23}=$ cyclopropylmethyl and $R^4=R^7$=benzyl, (78 mg, 0.18 mmol) in methylene chloride was cooled to 0° C. in an ice bath and treated with DAST (0.04 mL; 0.3 mmol). After stirring a few minutes, analysis by TLC (silica gel 40% ethyl acetate/hexane) showed no starting material remained. The mixture was quenched with sat'd NaHCO$_3$, the organic layer separated, and washed with water and brine. The solution was dried over MgSO$_4$ and evaporated. The residue was chromatographed by HPLC on silica gel (40% ethyl acetate/hexane) to give 50 mg of the desired product. MS m/z 439 (M+H)$^+$; NMR (CDCl$_3$) C2 symmetrical: δ 7.36–7.11 (m, 5H), 4.90–4.74 (m) [total 1H, HF=50 Hz], 4.06 (t, 5.5 Hz, 1H), 3.53 (dd, 7 Hz, 15 Hz, 1H), 2.99 (overlapping m, 3H), 0.95 (m, 1H), 0.59 (m, 1H), 0.48 (m, 1H), 0.31 (m, 1H), 0.22 (m, 1H).

Example 4

(3S-trans)-4,5-bis(1S-fluoro-2-phenylethyl)-1,3-bis(2-naphthalenylmethyl)-2-imidazolidinone A solution of compound XIX, where $R^{22}=R^{23}=$2-naphthyl and $R^4=R^7$=benzyl, (100 mg, 0.16 mmol) in methylene chloride was cooled to 0° C. in an ice bath and treated with DAST (0.04 mL; 0.3 mmol). After stirring a few minutes, analysis by TLC (silica gel 40% ethyl acetate/hexane) showed no starting material remained. The mixture was quenched with sat'd NaHCO$_3$, the organic layer separated and washed with water and brine. The solution was dried over MgSO$_4$ and evaporated. The residue was chromatographed by HPLC on silica gel (40% ethyl acetate/hexane) to give 50 mg of the title compound. MS m/z 611 (M+H)$^+$; NMR (CDCl$_3$) C2 syrmetrical: δ7.83 (m, 3H), 7.73 (s, 1H), 7.49 (m, 3H), 7.10 (m, 3H), 6.66 (d, 6 Hz, 2H), 4.57–4.42 (m) [total 1H, HF=46 Hz], 3.50 (t, 6 Hz, 1H)

Example 5

(3S-trans)-4,5-bis(1S-fluoro-2-phenylethyl)-1,3-bis(2-propenyl)-2-imidazolidinone A solution of compound XIX, where $R^{22}=R^{23}$=allyl and $R^4=R^7$=benzyl, (70 mg, 0.17 mmol) in methylene chloride was cooled to 0° C. in an ice bath and treated with DAST (0.04 mL; 0.3 mmol). After stirring a few minutes, analysis by TLC (silica gel 40% ethyl acetate/hexane) showed no starting material remained. The mixture was quenched with sat'd NaHCO$_3$, the organic layer separated and washed with water and brine. The solution was dried over MgSO$_4$ and evaporated. The residue was chromatographed by HPLC on silica gel (40% ethyl acetate/hexane) to give 40 mg of the desired product. MS m/z 411 (M+H)$^+$; NMR (CDCl$_3$) C2 symmetrical: δ 736–7.20 (m, 5H), 5.82 (m, 1H), 5.27 (d, 6 Hz, 1H), 5.23 (s, 1H), 4.79–4.62 (m) [total 1H, HF=48 Hz], 4.29 (dd, 5 Hz, 15 Hz, 1H), 3.80 (t, 6 Hz, 1H), 3.64 (dd, 8 Hz, 15 Hz, 1H), 2.90 (m, 2H).

Example 6

(3R-trans)-4,5-bis(1R-fluoro-2-phenylethyl)-1,3-bis (2-propenyl)-2-imidazolidinone A solution of the enantiomer of compound XIX, where $R^{22}=R^{23}$ Alkyl and $R^4=R^7$=benzyl, (80 mg, 0.17 mmol) in methylene chloride was cooled to 0° C. in an ice bath and treated with DAST (0.04 mL; 0.3 mmol). After stirring a few minutes analysis, by TLC (silica gel 40% ethyl acetate/ hexane) showed no starting material remained. The mixture was quenched with sat'd NaHCO$_3$, the organic layer separated and washed with water and brine. The solution was dried over MgSO$_4$ and evaporated. The residue was chromatographed by HPLC on silica gel (40% ethyl acetate/ hexane) to give 50 mg of the desired product. MS m/z 411 (M+H)$^+$; NMR (CDCl$_3$) C2 symmetrical: δ 7.36–7.20 (m, 5H), 5.82 (m, 1H), 5.27 (d, 6 Hz, 1H), 5.23 (s, 1H), 4.79–4.62 (m) [total 1H, HF=48 Hz], 4.29 (dd, 5 Hz, 15 Hz, 1H), 3.80 (t, 6 Hz, 1H), 3.64 (dd, 8 Hz, 15 Hz, 1H), 2.90 (m, 2H).

Example 7

(4S-trans)-dimethyl 3,3'-[[4-(1S-hydroxy-2-phenylethyl)-2-oxo-5-(2-phenylethyl)-1,3-imidazolidinyl]bis-(methylene)]bis [benzoate]

A solution of compound XXI, where $R^{22}=R^{23}$=3-carbomethoxybenyl and $R^4=R^7$=benzyl, (850 mg, 1.4 mmol) in THF was treated under Mitsunobu conditions with triphenylphosphine(TPP) (730 mg, 2.8 mmol), DEAD (490 mg, 2.8 mmol), and chloroacetic acid (CAA) (260 mg, 2.8 mmol) at rt for 24 hrs. To the mixture was added methanol (10 ml), and the whole was stirred for 1 hr. The solution was then concentrated, and the residue chromatographed on silica gel (40% ethyl acetate/hexane) to give 500 mg of the ester intermediate as a foam. MS (M+NH$_4$)$^+$=700.3 (100%), (M+H)$^+$=683.3 (87%);

This intermediate ester was dissolved in methanol and treated with a 1N solution of sodium hydroxide (1 ml). The resulting mixture was stirred at room temperature for 30 min. TLC analysis showed no starting material remained. The solution was evaporated to dryness, and the residue partitioned between water and ethyl acetate. The organic layer was separated and washed with water, brine, and dried over MgSO$_4$. Filtration and concentration gave a residue which was chromatographed on silica cell (50% ethyl acetate/hexane) to give 500 mg of the target compound as a foam. MS m/z 624.2 (32%, (M+NH$_4$)$^+$), 607.2 (100%, (M+H)$^+$); NMR (CDCl$_3$): δ 7.98 (m, 4H), 7.59 (d, 8 Hz, 1H), 7.41 (m, 3H), 7.21 (m, 6H), 6.91 (complex dd, 4H), 5.00 (d, 15 Hz, 1H), 4.93 (d, 15 Hz, 1H), 4.34 (d, 15 Hz, 1H), 4.05 ( d, 15 Hz, 1H), 3.84 (s, 3H), 3.8 (m, 1H), 3.78 (s, 3H), 3.48 (m, 1H), 3.38 (t, 4 Hz, 1H), 2.66 (dd, 1.8 Hz, 15 Hz, 1H), 2.43 (m, 1H), 2.30 (m, 1H), 2.17 (dd, 9 Hz, 14 Hz), 1.92 (d, 3 Hz, 1H), 1.78 (m, 2H).

Example 8

(4S-trans)-dimethyl 3,3'-[[4-(1S-bromo-2-phenylethyl)-2-oxo-5-(2-phenylethyl)-1,3-imidazolidinyl]bis-(methylene)]bis [benzoate]

A solution of compound XVI, where $R^{22}=R^{23}$=3-carbomethoxybenzyl and $R^4=R^7$=benzyl, (45 mg, 0.07 mmol) in methylene chloride was treated with triphenyphosphine (150 mg, 0.6 mmol), and carbon tetrabromide (175 mg, 0.5 mmol) at room temperature for 36 hrs. the solution was then concentrated, and the residue chromatographed on silica gel (40% ethyl acetate/hexane) to give 20 mg of the desired product as a colorless film. MS m/z 688.3/686.3 (100%/92%, (M+NH$_4$)$^+$) 671.2/669.2 (82%/75%, (M+H)$^+$). NMR (CDCl$_3$): δ 7.98 (m, 4H), 7.59 (d, 8 Hz, 1H), 7.41 (m, 3H), 7.21 (m, 6H), 7.01 (d, 2H), 6.80 (m, 2H), 5.08 (d, 15 Hz, 1H), 4.86 (d, 15 Hz, 1H), 4.36 (d, 15 Hz, 1H), 4.08 (d, 15 Hz, 1H), 4.08 (m, 1H), 3.84 (s, 3H), 3.76 (s, 3H), 3.67 (t, 4 Hz, 1H), 3.58 (m, 1H), 3.07 (dd, 1.8 Hz, 15 Hz, 1H), 2.50 (m, 1H), 2.32 (m, 1H), 2.32 (dd, 1.8 Hz, 15 Hz), 1.88 (m, 2H).

Example 9

(4R-trans)-dimethyl 3,3'-[[2-oxo-4,5-bis(2-phenylethyl)-1,3-imidazolidinedily]bis-(methylene)]bis[benzoate]

A solution of the compound of Ex. 7 (300 mg, 0.5 mmol) in THF was treated with thiocarbonyldiimidazole (178 mg, 1.0 mmol) and the resulting mixture was heated at reflux for 24 hrs. Solvent was removed on a rotary evaporator, and the residue was chromatographed on silica gel (40% ethyl acetate/hexane) to give 220 mg of intermediate thiocarbamate as a white foam. MS m/z 717.4/718.4 (100%/48%, (M+H)$^+$).

This intermediate thiocarbamate (220 mg, 0.3 mmol) was dissolved in tetrahydrofuran and treated with tributyltin hydride (0.18 mL, 0.6 mmol) and 50 mg of AIBN, and the resulting mixture was heated to reflux for 4 hrs. The solution was concentrated, and the residue dissolved in acetonitrile and extracted with hexane to remove tin compounds. The acetonitrile solution was concentrated, and the residue was chromatographed on silica gel (40% ethyl acetate/hexane) to give 50 mg of the desired product as a white foam. MS 591.3 (100%, (M+H)$^+$). NMR (CDCl$_3$) C2 symmetrical: δ7.95 (m, 2H), 7.52 (d, 8 Hz, 1H), 7.43 (t, 1H), 7.21 (m, 3H), 6.91 (complex dd, 2H), 5.00 (d, 15 Hz, 1H), 4.11 (d, 15 Hz, 1H), 3.85 (s, 3H), 3.38 (t, 3 Hz, 1H), 2.44 (m, 1H), 2.28 (m, 1H), 1.77 (m, 2H).

Example 10

(4S-trans)-3,3'-[[4-(1S-hydroxy-2-phenylethyl)-2-oxo-5-(2-phenylethyl)-1,3-imidazolidinyl]bis-(methylene)]bis [benzenemethanol]

A solution of the compound of Ex. 7 (100 mg, 0.17 mmol) in ether was treated with lithium aluminum hydride (37 mg, 1.0 mmol) at room temperature for 1 hr. The reaction was quenched with 1N HCl. The organic layer was separated, washed with water and brine, and then dried over MgSO$_4$. Filtration and concentration gave a residue which was chromatographed on silica gel 150% ethyl acetate/hexane)

to give 50 mg of the title compound as a white foam. MS m/z 551.2 (100%, (M+H)⁺); NMR (CDCl₃): δ 7.21 (m, 14H), 6.91 (complex dd, 4H), 4.83 (d, 15 Hz, 1H), 4.73 (d, 15 Hz, 1 H), 4.56 (s, 2H), 4.54 (s, 2H), 4.24 (d, 15 Hz, 1H), 3.95 (d, 15 Hz, 1H), 3.75 (m, 1H), 3.44 (m, 1H), 3.31(t, 4 Hz, 1H), 2.56 (dd, 1.5 Hz, 11 Hz, 1H), 2.43 (m, 1H), 2.30 (m, 1H), 2.11 (dd, 9 Hz, 14 Hz), 1.71 (m, 2H).

Example 11

(4R-trans)-3,3'-[[2-oxo-4,5-bis(2-phenylethyl)-1,3-imidazolidiny]bis-(methylene)]bis [benzenemethanol]

A solution of the compound of Ex. 9 (50 mg, 0.08mmol) in ether was treated with lithium aluminum hydride (37 mg, 1.0 mmol) at room temperature for 1 hr. The reaction was quenched with 1N HCl. The organic layer was separated, washed with water and brine, and then dried over MgSO₄. Filtration and concentration gave a residue which was chromatographed on silica gel (100% EtOAc) to give 20 mg of The desired product as a white foam. MS m/z 535.4 (100%, (M+H)⁺). NMR (CDCl₃) C2 symmetrical: δ 7.33–7.16 (m, 7H), 6.90 (d, 2H), 4.74(d, 15 Hz, 1H), 4.63 (s, 2H), 4.06 (d, 15 Hz, 1H), 3.23 (m, 1H), 2.42 (m, 1H), 2.28 (m, 1H), 1.74 (m, 2H).

Example 12

(4R-trans)-dimethyl 3,3'-[[2-oxo-4,5-bis(benzyl)-1,3-imidazolidiny]bis-(methylene) ]bis[benzoate]

A solution of amide IV (28 g, 90 mmol) in tetrahydrofuran was cooled in an ice bath and treated with a 2M solution of benzylmagnesium chloride (150 mL, 300 mmol). After stirring for 30 minutes, the reaction was quenched with 1N HCl and extracted into ether. The ether extract was washed with water, brine, and cried over MgSO₄. The solution was filtered, concentrated and the residue chromatographed on silica gel (10% EtOAc/Hex) to give 6.4 g of the benzyl ketone VIII as a white solid. MS m/z 340.0 (8%, (M+H)⁺), 301.0 (100%, (M+NH₄–C₄H₈)⁺), 240.1 (84%, (M+H–Boc)⁺).

A solution of ketone V (6.0g, 18.0 mmol) in methanol was cooled to 0° C. in an ice bath and treated with sodium borohydride (0.67 g, 18 mmol) and stirred for 3 hrs. A white suspension formed, and TLC analysis showed no starting material remained. The mixture was concentrated, and the residue was extracted into ethyl acetate and washed with 1N HCl, water, brine, then dried over MgSO₄ and concentrated to give 6 g of the mixture of alcohols IX as a white solid. MS m/z 342. 2 (8%, (M+H)⁺) , 286.0 (100%, (M+H–C₄H₈)⁺).

A solution of the mixture of alcohols VI (4.8 g, 14 mmol) in methylene chloride was cooled to 0° C. in an ice bath and treated with triethylamine (1.8 g, 18 mmol) and methanesulfonyl chloride (2 g, 17 mmol) . After all the starting material was consumed as judged by TLC, the solution was washed with 1N HCl, sat'd NaHCO₃, water, and brine. The mixture was dried over MgSO₄, filtered and concentrated to give the mesylate intermediate. The crude mesylate was dissolved in N,N-dimethylformamide, treated with sodium azide (6.5 g, 100 mmol) and heated between 55° to 75° C. for 6 hrs. The resulting mixture was poured into water, and the suspension extracted into ethyl acetate. The extract was washed water and brine, then dried over MgSO₄. The solution was filtered, concentrated and the residue chromatographed on silica gel (15% ethyl acetate/hexane) to give the two diastereomeric azides. The major isomer X eluted first and was obtained as an oil (1.8 gm). IR 2105 cm⁻¹ (N₃), MS m/z 367.1 (8%, (M+H)⁺), 311.0 (100%, (M+H–C₄H₈)⁺), 267.1 (68%, (M+H–Boc)⁺), 328 (43%, (M+NH₄–C₄H₈)⁺). This was followed by the minor isomer XI which was obtained as a white solid (0.5 gm). IR 2105 cm⁻¹ (N₃), MS m/z 367.1 (11%, (M+H)⁺), 311.0 (100%, (M+H–C₄H₈ )⁺), 267.1 (61%,, (M+H–Boc)⁺), 328 (42%, (M+NH₄–C₄H₈)⁺).

The major isomeric azide VII from above was dissolved in tetrahydrofuran and treated with 0.5 g of 10% Pd/C and hydrogenated in a Parr aparatus at 55 psi of H₂ for 5 hrs. The mixture was filtered through a pad of Celite and concentrated. The residue was redissolved in tetrahydrofuran and cooled to 0° C. in an ice bath and treated with HCl₍ₐ₎ for 1 hr. The solution was concentrated, and the residue was again redissolved in tetrahydrofuran, made basic with triethylamine and treated with carbonyldiimidazole (0.79 g, 4.9 mmol).The resulting mixture was stirred overnight at room temperature. The mixture was then concentrated, and the residue chromatographed on silica gel (50% ethyl acetate/ hexane to 100% ethyl acetate) to give 100 mg of imidazolidinone XII: MS m/z 267.0 (100%, (M+H)⁺), NMR (CDCl₃) C2 symmetrical: δ7.27 (m, 3H), 7.12 (d, 7 Hz, 2H), 4.92 (bs, 1H), 3.65 (t, 7 Hz, 1H), 2.72 (m, 2H).

The imidazolidinone VIII obtained above (100 mg, 0.38 mmol) was dissolved in N,N-dimethylformamide, and treated with sodium hydride (60% oil dispersion, 60 mg, 1.5 mmol) and stirred for 20 min. Methyl 3-(bromomethyl) benzoate (300 mg, 1.5 mmol) was added to the resulting mixture, and stirring was continued for 1 hr. The reaction mixture was poured in 1N HCl and extracted into ethyl acetate. The extract was washed with water and brine, dried and concentrated. The residue was chromatographed on silica gel (50% ethyl acetate/hexane) to give 100 mg of the target compound. MS m/z 563.2 (100%, (M+H)⁺), NMR (CDCl₃) C2 symmetrical: δ 7.99 (d, 7.7 Hz, 1H), 7.86 (s, 1H), 7.43 (t, 7.7 Hz, 1H), 7.31 (d, 7.7 Hz, 1H), 7.09 (m, 3H), 6.61 (complex dd, 2H), 4.99 (d, 15 Hz, 1H), 3.96 (d, 15 Hz, 1H), 3.95 (s, 3H), 3.26 (t, 5 Hz, 1H), 2.66 (dd, 4.4 Hz, 13 Hz, 1H), 2.34 (dd, 7.3 Hz, 13 Hz, 1H).

Example 13

(4R-trans)-3,3'-[[2-oxo-4,5-bis(benzyl)-1,3-imidazolidiny]bis-(methylene)]bis [benzenemethanol]

A solution of the compound of Ex. 12 (95 mg, 0.17 mmol) in ether was treated with lithium aluminum hydride (13 mg, 0.34 mmol), and the resulting mixture was stirred at rt for 1 hr. The reaction was quenched with 1N HCl, and the organic layer separated and washed with water and brine. The ether was removed on a rotary evaporator, and the residue was chromatographed on silica gel (80% ethyl acetate/hexane) to give 50 mg of the desired product as a white solid. The structure was confirmed by single crystal x-ray analysis. MS m/z 507.2 (100%, (M+H)⁺).

Example 14

(4R-trans)-3,3'-[[2-oxo-4,5-bis(2-phenylethyl)-1,3-imidazolidiny]bis-(methylene)]bis [N'-hydroxybenzenecarboximidamide]

A solution of compound XXI, where R²²=R²³=3-cyanobenzyl and R⁴=R⁷=benzyl, (1.7 g, 3.0 mmol) in tetrahydrofuran was treated under Mitsunobu conditions with triphenylphosphine(TPP) (1.57 g, 6.0 mmol), diethylazodicarboxylate (1.0 g, 6.0 mmol), and chloroacetic acid (600 mg, 6.0 mmol) at room temperature for 24 hrs. Methanol (10 ml) was added to the resulting mixture and the whole was stirred for 1 hr. The solution was then concentrated, and the residue chromatographed on silica gel (50% ethyl acetate/hexane) to give 500 mg of the ester intermediate as a foam. MS m/z 558.3 (25%,(M+NH$_4$)$^+$), 541.3 (100%, (M+H)$^+$);

This ester intermediate was dissolved in methanol and treated with 1N NaOH (3 ml). The resulting mixture was stirred at room temperature for 30 min. TLC analysis showed no starting material remained. The solution was evaporated to dryness, and the residue partioned between water and ethyl acetate. The organic layer was separated and washed with water, brine, and then dried over MgSO$_4$. Filtration and concentration gave alcohol Vb (400 mg) as a foam. MS 558.3 (25%, (M+NH$_4$)$^+$), 541.3 (100%, (M+H)$^+$).

A solution of the alcohol XXII, ($R^{22}=R^{23}$=3-carbomethoxybenzyl; $R^4=R^7$=benzyl), (400 mg, 0.8 mmol) in tetrahydrofuran was treated with thiocarbonyldiimidazole (200 mg, 1.1 mmol) and heated at reflux for 24 hrs. The mixture was concentrated, and the residue chromatographed on silica gel (40% ethyl acetate/hexane) to give 200 mg of the intermediate thiocarbamate as a white foam. MS m/z 651.4 (45%, (M+H)$^+$), 523.3 (100%, (M+H–C$_4$H$_4$OSN$_2$)$^+$).

This intermediate thiocarbamate (200 mg, 0.3 mmol) was dissolved in tetrahydrofuran and treated with tributyltin hydride (0.18 mL, 0.6 mmol) and 50 mg of AIBN, and the mixture was heated to reflux for 4 hrs. The solution was concentrated, and the residue dissolved in acetonitrile and extracted with hexane to remove tin compounds. The acetonitrile solution was concentrated and the residue was chromatographed on silica gel (50–65% ethyl acetate/hexane) to give 70 mg of ($R^{22}=R^{23}$=3-cyanobezyl; $R^4=R^7$=benzyl) as a film. MS m/z 525.3 (100%, (M+H)$^+$). NMR (CDCl$_3$) C2 symmetrical: δ7.52 (m, 4H), 7.24 (m, 3H), 6.94 (d, 7 Hz, 2H), 4.85 (d, 15 Hz, 1H), 4.09 (d, 15 Hz, 1H), 2.45 (m, 1H), 2.25 (m, 1H), 1.80 (m, 2H).

A solution of compound IX ($R^{22}=R^{23}$=3-cyanobenzyl; $R^4=R^7$=benzyl) (70 mg, 0.13 mmol) in ethanol was treated with hydroxylamine hydrochloride (70 mg, 1.1 mmol) and triethylamine (110 mg, 1.1 mmol) and heated to reflux until anlysis by TLC showed no starting material remained. The solution was concentrated, and the resulting white solid was partitioned between water and ethyl acetate. The organic layer was washed with water and brine, dried over MgSO$_4$ and concentrated to give 70 mg of the title compound as a white solid. MS m/z 591 (100%, (M+H)$^+$), 575 (70%, (M+H–O)$^+$). NMR (CDCl$_3$) C2 symmetrical: δ7.8–7.1 (m, 8H), 6.91 (d, 7 Hz, 2H), 4.95 (bs, 2H), 4.80 (d, 15 Hz, 1H), 4.15 (d, 15 Hz, 1H), 3.47 (t, 7 Hz, 1H), 2.42 (m, 1H), 2.26 (m, 1H), 1.75 (m, 2H).

Example 201

To a solution of (+)-biotin (11.5 g, 47 mmol, 1 eq) in DMF (50 mL) at 0° C. was added dropwise a suspension of 4 equivalents of sodium hydride (4.5 g, 188 mmol) in 10 ml DMF. The solution was then warmed to room temperature, and m-bromobenzyl bromide (32 g, 150 mmol, 3 eq) in 5 mL DMF was added. The mixture was stirred overnight, quenched with HCl (conc.) and extracted with ethyl acetate. Purification by column chromatography gave the title compound $^1$H NMR (CDCl$_3$): δ 1.2–1.7 (m, 6H), 2.2 (s,1H), 2.7 (m, 2H), 3.1 (m,1H), 3.6 (t, 2H), 3.8–4.0 (m, 3H), 4.1 (d, J=15.4 Hz, 1H), 4.7 (d, J=15.4 Hz, 1H), 5.0 (d, J=15.4 Hz, 1H), 7.1–7.4 (m, 8H); $^{13}$C NMR (CDCl$_3$): δ26.01, 29.25, 29.39, 32.93, 35.16, 46.29, 47.88, 55.08, 61.63, 62.96, 63.03, 123.20, 123.24, 127.05, 127.12, 130.83, 130.86, 130.99, 131.22, 131.37, 131.43, 139.62, 139.83, 161.28; LRMS: m/z 569.0 [M+1]$^+$; HRMS: Calcd for C$_{24}$H$_{28}$N$_2$O$_2$SBr$_2$ 569.0296. Found 569.0296.

Example 202

Using the procedure of Example 201 and substituting biotin-alcohol (prepared by reduction of (+)-biotin with LiBH(OMe)$_3$) for biotin provided the desired compound. (55%) $^1$H NMR (CDCl$_3$): δ1.2–1.7 (m, 6H), 2.2 (s, 1H), 2.7 (m, 2H), 3.1 (m, 1H), 3.6 (t, 2H), 3.8–4.0 (m, 3H), 4.1 (d, J=15.4 Hz, 1H), 4.7 (d, J=15.4 Hz, 1H), 5.0 (d, J=15.4 Hz, 1H), 7.1–7.4 (m, 8H); $^{13}$C NMR (CDCl$_3$): δ26.01, 29.25, 29.39, 32.93, 35.16, 46.29, 47.88, 55.08, 61.63, 62.96, 63.03, 123.20, 123.24, 127.05, 127.12, 130.83, 130.86, 130.99, 131.22, 131.37, 131.43, 139.62, 139.83, 161.28; LRMS: m/z 569.0 [M+1]$^+$; HRMS: calcd for C$_{24}$H$_{28}$N$_2$O$_2$SBr$_2$ 569.0296, found 569.0296.

Example 203

To a solution of the compound of example 201 (1.2 g, 2.0 mmol, 1 eq) in methanol (13 ml, 0.25M), cooled to 0° C., was added a suspension of OXONE (KHSO$_5$) (3.7 g, 6.1 mmol, 3 eq) in 11 mL H$_2$O was added. The reaction mixture was stirred overnight, extracted with ether, washed with water, and dried over MgSO$_4$. The residue was isolated by preparative TLC to give the product as a white solid (67%). $^1$H NMR (CDCl$_3$): δ 1.2–1.8 (m, 6H), 2.3 (t, J=7.0 Hz, 2H), 2.9–3.0 (m, 1H), 3.0–3.1 (m, 2H), 3.7 (s, 3H), 3.9 (d, J=15.4 Hz, 1H), 4.0–4.2 (m, 2H), 4.1 (d, J=15.4 Hz, 1H), 4.7 (d, J=15.4 Hz, 1H), 4.9 (d, J=15.4 Hz, 1H), 7.2–7.5 (m, 8H); LRMS: m/z 628.0 [M+NH$_4$]$^+$; HRMS: calcd for C$_{25}$H$_{29}$N$_2$O$_5$SBr$_2$ 627.0163, found 627.0168.

Example 204

Using the procedure of example 203 and substituting the compound of example 202 for the compound of example 201 gave the desired alcohol. (32%) $^1$H NMR (CDCl$_3$): δ 1.2–1.9 (m, 9H), 2.9–3.1 (m, 3H), 3.7 (t, J=6.6 Hz, 2H), 4.0 (d, J=15.4 Hz, 1H), 4.1 (d, J=15.0 Hz, 1H), 4.0–4.2 (m,2H), 4.7 (d, J=15.4 Hz, 1H), 4.9 (d, J=15.4 Hz, 1H), 7.2–7.5 (m, 8H); $^{13}$C NMR (CDCl$_3$): δ24.7, 25.7, 27.2, 32.2, 46.8, 47.6, 50.4, 51.9, 55.3, 61.5, 62.5, 123.2, 123.3, 126.8, 126.9, 130.7, 130.8, 131.2, 131.3, 131.4, 131.5, 137.9, 138.2, 159.8; LRMS: m/z 601.0 (96.64) [M+1]$^+$, 618 (100) [M+NH$_4$]$^+$; HRMS: calcd for C$_{24}$H$_{29}$N$_2$O$_4$SBr$_2$ 599.0214, found 599.0201.

Example 205

To a solution of (+)-biotin (11.5 g, 47 mmol, 1 eq) in DMF (50 mL) at 0° C. was added dropwise a suspension of 4 equivalents of sodium hydride (washed with toluene, 4.5 g, 188 mmol) in 10 ml DMF. The solution was then warmed to room temperature, and m-bromobenzyl bromide (32 g, 150 mmol, 3 eq) in 5 mL DMF was added. The mixture was stirred overnight, quenched with HCl (conc.) and extracted with ethyl acetate. Purification by column chromatography gave example 205 in 52% yield. Example 205: $^1$H NMR (CDCl$_3$): δ1.2–1.8 (m, 6H), 2.4 (t, J=7.0 Hz, 2H), 2.7 (m, 2H), 3.1 (m, 1H), 3.8–4.2 (m, 4H), 4.7 (d, J=15.3 Hz, 1H), 5.0 (d, J=15.3 Hz, 1H), 5.1 (s, 2H), 7.1–7.4 (m, 12H); $^{13}$C NMR (CDCl$_3$): δ24.5, 28.4, 28.5, 31.9, 33.9, 34.6, 45.9, 47.4, 54.2, 61.1, 62.6, 65.1, 71.4, 122.5, 122.8, 122.7, 126.1, 126.6, 126.7, 129.9, 130.0, 130.2, 130.4, 130.5, 130.7, 130.8, 130.9, 131.0, 131.2, 131.4, 131.9, 138.2, 139.1, 139.3, 160.7, 172.9; LRMS: m/z 753.0 [M+1]⁺; HRMS: calcd for $C_{31}H_{32}N_2O_3SBr_3$ 748.9683, found 748.9671.

Example 206

To a solution of compound of Example 205 (2 g, 2.6 mmol, 1 eq) and 1-ethoxy-1-(trimethylstannyl)ethylene (3.0 mL, 15.6 mmol, 6 eq) in dry THF (10 mL) in a tube was added tetrakis(triphenylphosphine) palladium(0) (460 mg, 0.4 mmol, 0.15 eq). The solution was degassed, and then the tube was sealed. After stirring at 75° overnight, the reaction mixture was concentrated in vacuo, and the residue purified via column chromatography to give the product (1 g, 40%) as a yellow solid. ¹H NMR (CDCl₃): δ1.2–1.8 (m, 6H), 2.4 (t, J=7.0 Hz, 2H), 2.59 (s, 3H), 2.60 (s, 3H), 2.62 (s, 3H), 2.7 (m, 2H), 3.1 (m, 1H), 3.9–4.0 (m, 2H), 4.0 (d, J=15.4 Hz, 1H), 4.2 (d, J=15.4 Hz, 1H), 4.7 (d, J=15.3 Hz, 1H), 5.1 (d, J=15.4 Hz, 1H), 5.2 (s, 2H), 7.4–8.0 (m, 12H); ¹³C NMR (CDCl₃):δ24.5, 26.5, 28.4, 33.9, 34.7, 46.2, 46.3, 47.6, 54.1, 61.3, 62.8, 65.5, 127.5, 127.7, 128.0, 128.7, 129.0, 132.6, 136.6, 137.43, 137.46137.5, 137.6, 160.8, 172.9, 197.6, 197.7; LRMS: m/z 641.4 (100) [M+1]⁺, 658.4 (71.87) [M+NH₄]⁺.

Example 207

Using the procedure of Example 206 was and substituting the compound of ex. 202 for the compound of Example 205 gave the product. (54%) ¹H NMR (CDCl₃): δ1.2–1.7 (m, 8H), 2.0 (s, 1H), 2.60 (s, 3H), 2.65 (s, 3H), 2.7 (m, 2H), 3.1–3.2 (m, 1H), 3.6 (t, J=6.6 Hz, 2H), 3.9–4.1 (m, 2H), 4.1 (d, J=15.4 Hz, 1H), 4.3 (d, J=15.4 Hz, 1H), 4.7 (d, J =15.4 Hz, 1H), 5.1 (d, J=15.4 Hz, 1H), 7.2–7.9 (m, 8H); ¹³C NMR (CDCl₃): δ25.9, 27.0, 29.2, 32.8, 35.3, 46.8, 48.2, 54.9, 62.0, 63.0, 63.3, 127.9, 128.0, 128.2, 128.3, 129.6, 129.7, 132.5, 133.0, 133.2, 137.9, 138.1, 138.2, 161.4; LRMS: m/z 495.2 (56.26) [M+1]⁺, 512.2 (100) [M+NH₄]⁺; HRMS: calcd for $C_{28}H_{35}N_2O_4S$ 495.2317, found 495.2326.

Example 208

A solution of the methylketone of Example 206 (95 mg, 0.15 mmol, 1 eq) in methanol (2.5 mL) was added dropwise to a mixture of NaBH₄ (39 mg, 10.0 mmol, 3.3 eq) in 2.5 mL methanol. After stirring at room temperature for two hours, quenching with concentrated HCl to pH 3, and purification by preparative tlc, the desired product was obtained (55% yield). ¹H NMR (CDCl₃): δ1.2–1.7 (m,12H), 2.1 (s, 1H), 2.3 (m, 2H), 2.7 (m, 3H), 3.1 (m, 1H), 3.7 (s, 2H), 3.8–4.1 (m, 3H), 4.7–5.0 (m, 3H), 7.1–7.4 (m, 8H); LRMS: m/z 509.2 (100) [M+1]⁺, 491.2 (47.71) [M-H₂O]⁺; HRMS: calcd for $C_{29}H_{37}N_2O_4S$ 411.2106, found 411.2107.

Example 209

To a solution of compound of Example 206 (300 mg, 0.5 mmol, 1 eq) in a 1:1 mixture of ethanol/pyridine (5 mL) was added hydroxylamine hydrochloride (200 mg, 3 mmol, 6 eq) in 3 mL ethanol/pyridine. The reaction mixture was refluxed for four hours, after which the solvent was distilled off. The residue was quenched with saturated ammonium choride solution, extracted with ethyl acetate, washed with brine, and dried over sodium sulfate. The product was obtained in nearly quantitative yield (340 mg, 98%). ¹H NMR (CDCl₃): δ 1.2–1.8 (m, 8H), 2.2 (m, 9H), 2.4 (t, 2H), 2.7 (m, 2H), 3.1 (m, 1H), 3.8–4.2 (m, 4H), 4.8 (d, 1H), 5.1 (d, 1H), 5.2 (s, 2H), 7.2–7.4 (m, 12H); ¹³C NMR (CDCl₃): δ11.6, 11.62, 24.2, 28.1, 28.2, 33.6, 34.3, 45.8, 47.6, 54.3, 61.1, 62.4, 65.8, 123.9, 124.2, 125.39, 125.44, 125.5, 125.7, 125.8, 128.22, 128.24, 128.35, 128.38, 128.51, 128.59, 128.63, 135.8, 136.5, 136.6, 136.8, 137.2, 137.3, 137.5, 148.7, 154.7 154.83, 154.81, 161.3, 173.6.

Example 210

Substitution of the compound of Example 207 in the procedure of Example 208 gave the product (52.7%). ¹H NMR (CDCl₃): δ1.2–1.7 (m, 14H), 1.8 (s, 1H), 2.6–2.8 (m, 2H), 3.0–3.2 (m, 1H), 3.6 (t, J=6.2 Hz, 2H), 3.8–4.1 (m, 4H), 4.7–5.1 (m, 4H), 7.1–7.3 (m, 8H); ¹³C NMR (CDCl₃): δ 25.1, 25.3, 28.7, 28.8, 32.4, 34.6, 46.3, 48.0, 54.5, 54.6, 61.1, 62.7, 69.9, 124.7, 124.9, 125.0, 125.2, 127.2, 128.6, 136.9, 137.0, 137.3, 146.8, 161.1; LRMS: m/z 499 (24.8%) [M+1]⁺, 481 (77.2%) [M+1–OH], 463 (100%) [M+1–2×OH].

Example 211

The compound of Example 205 was refluxed with 10% NaOMe in excess methanol to give the desired product in quantitative yield. ¹H NMR (CDCl₃): δ1.2–1.8 (m, 6H), 2.3 (t J=7.0 Hz, 2H), 2.6–2.8 (m, 1H), 3.1–3.2 (m, 1H), 3.4 (m, 1H), 3.7 (s, 3H), 3.9 (d, J=15.4 Hz, 1H), 4.0 (d, J=15.4 Hz, 1H), 4.6–4.7 (m, 2H), 4.7 (d, J=15.4 Hz, 1H), 5.0 (d, J=15.4 Hz, 1H), 7.1–7.5 (m, 8H); ¹³C NMR (CDCl₃): δ34.5, 28.4, 28.5, 33.7, 34.6, 45.7, 17.3, 51.4, 54.3, 61.1, 62.6, 63.9, 122.3, 122.6, 122.7, 125.1, 126.5, 129.6, 129.8, 130.1, 130.2, 130.3, 130.7, 130.71, 1:30.81, 130.86, 138.9, 139.2, 143.4, 160.8, 173.8; LRMS: m/z 597.0 [M+1]⁺.

Example 212

To a solution of the compound of Example 205 (650 mg, 1.1 mmol, 1 eq) in dry THF (5 mL) was added 3 equivalents of the 1-SEM-5-pyrazolyl boronic acid (790 mg, 3.3 mmol) in 5 mL THF, a solution of potassium carbonate (11.25 g) in 30 mL water, and tetrakis(triphenylphosphine)palladium (0) (190 mg, 0.16 mmol, 0.15 eq). After refluxing for six hours, the product was isolated via column chromatography in 72% yield. ¹H NMR (CDCl₃): δ0.0 (s, 18H), 0.9 (t, J=8.1 Hz, 4H), 1.2–1.8 (m, 6H), 2.3 (t, J=7.0 Hz, 2H), 2.8 (m, 2H), 3.1 (m, 1H), 3.4 (s, 3H), 3.7 (t, J=6.7 Hz, 4H), 3.9–4.0 (m, 2H), 4.0 (d, J=15.4 Hz, 1H), 4.3 (d, J=15.4 Hz, 1H), 4.7 (d, J=15.4 Hz, 1H), 5.1 (d, J=15.4 Hz, 1H), 5.4 (s, 4H), 6.4 (s, 2H), 7.2–7.5 (m, 10H); ¹³C NMR (CDCl₃): δ-1.34, 18.77, 18.83, 25.74, 29.87, 29.94, 34.57, 35.78, 46.89, 56.31, 63.44, 64.93, 67.79, 67.82, 78.93, 108.16, 129.24, 129.28, 129.48, 129.55, 130.29, 130.33, 131.78, 131.80, 139.27, 139.59, 140.41, 145.86, 163.27, 175.64; LRMS: m/z 831.5 [M+1]⁺.

Example 213

The compound of Example 212 was stirred overnight in 5 mL of a 1:1 solution of 4N HCl/methanol. Evaporation to dryness gave the product. ¹H NMR (CD₃OD): δ1.3–1.9 (m, 6H), 2.4 (t, J=7.0.Hz, 2H), 2.8–3.0 (m, 2H), 3.3 (m, 1H), 3.4 (S, 3H), 4.1–4.4 (m, 3H), 4.83 (d, J=15.4 Hz, 1H), 5.01 (d, J=15.4 Hz, 1H), 6.7 (m, 2H), 7.3–7.4 (m, 4H), 7.7–7.8 (m.6H); ¹³C NMR (CD₃OD): δ25.73, 29.87, 29.97, 34.57, 35.63, 48.88, 51.98, 56.43, 63.25, 64.63, 103.50, 126.02, 126.50, 128.61, 128.67, 130.27, 130.32, 138.91, 139.26, 163.49, 175.78; LRMS: m/z 571.2 [M+1]⁺.

Example 214

The title compound was prepared from the compound of Example 215 by further treatment with MMMP as described under the procedure of Example 217. ¹H NMR (CDCl₃): δ1.26–1.33 (m, 1H), 1.52–1.79 (m, 5H), 2.38 (t, J=7.0 Hz, 2H), 2.88–2.92 (m, 1H), 3.04–3.07 (m, 2H), 3.96 (d, J=14.4

Hz, 1H), 4.06 (d, J=14.5 Hz, 1H), 4.0–4.2 (m, 2H), 4.20 (dd, J=9.6 Hz, J=6.6 Hz, 1H), 4.68 (d, J=15.3 Hz, 1H), 5.09 (s, 2H), 7.17–7.54 (m, 12H); $^{13}$C NMR (CDCl$_3$): δ24.11, 24.49, 26.65, 33.51, 46.39, 47.48, 50.15, 51.69, 55.17, 61.21, 65.14, 122.42, 122.97, 126.59, 126.70, 129.95, 130.10, 130.62, 130.91, 131.00, 131.09, 131.17, 131.25, 137.92, 138.16, 138.33, 159.72, 172.71; LRMS: m/z 721 (100%) [M+NH$_4$-HBr]$^+$; HRMS: calcd for C$_{31}$H$_{31}$N$_2$O$_5$SBr$_3$ 779.9503, found 779.9503.

Example 215

The title compound was prepared from the compound of Example 205 using the procedure described for example 211. $^1$H NMR (CDCl$_3$): δ 0.91 (q, J=0.9.6 Hz, 1H), 1.23–1.67 (m, 5H), 2.34 (t, J=7.3 Hz, 2H), 2.68 (dd, (J=14.2 Hz, J=5.86 Hz, 1H), 3.14 (dd, J=14.2 Hz, J=7.0 Hz, 1H), 3.27–3.32 (m, 1H), 4.02 (d, J=15.4 Hz, 1H), 4.20 (d, J=15.4 Hz, 1H), 4.36–4.42 (m, 1H), 4.59 (d, J=15.0 Hzz, 1H), 4.60–4.66 (m, 1H), 4.84 (d, J=15.0 Hz, 1H), 5.08 (s, 2H), 7.18–7.29 (m, 6H), 7.41–7.50 (m, 6H); $^{13}$C NMR (CDCl$_3$): 824.53, 27.68, 33.49, 46.82, 47.08, 53.73, 58.78, 61.18, 65.18, 67.68, 122.48, 122.94, 126.62, 126.78, 130.09, 130.51, 130.99, 131.17, 131-25, 138.05, 138.44, 138.50, 159.23, 172.55; LRMS: m/z 764 [M+H]$^+$; HRNS: calcd for C$_{31}$H$_{31}$N$_2$O$_4$SBr$_3$ 763.9555, found 763.9559.

Example 300

A. To a solution of o-phenylenediamine (20.0 g, 185 mmol) in THF (200 mL) was added carbonyldiimidazole (34.5 g, 212 mmol). The reaction mixture was stirred at room temperature overnight, and the solvent was removed under reduced pressure. The resulting solid was washed several times with ethyl ether, and then crystallized from methanol to give the title compound (23.0 g, 92% yield) as a white solid; mp: 250° C.; $^1$HNMR (CD$_3$OD, 300 MHz) δ7.2 (m, 2H) ; MS (CDI): m/z 151.9, (M+NH$_4$), 100%.

B. To a solution containing 0.5 g (3.7 mmol) of the compound of Example 300A in 10 mL of DMF was added 0.37 g (10.0 mmol) of sodium hydride (60% dispersion) at –10° C. under N$_2$ atmosphere. The reaction mixture was stirred at –10° C. for 10 min, and then 3.50 g (18.0 mmol) of octanyl bromide was added in one portion. The reaction was stirred for an additional 2 h at room temperature, washed with water, and extracted with ethyl acetate. The organic layer was dried over sodium sulfate, and then concentrated to leave an oil, which was purified by silica gel chromatography using 10% ethyl acetate in hexane as the eluent. The major fraction (72% yield) contained bis-(N-octyl-2-benzimidazolinone (oil); $^1$HNMR (CDCl$_3$, 300 MHz) δ0.85 (m, 3H), 1.15 (m, 8H),1.40 (m, 2H), 1.82 (m, 2H), 3.90 (m, 2H), 3.95 (m, 2H), 6.95 (m, 1H) and 7.0 (m,1H); MS (CDI): M+1=359.4, 100%.

Using the procedure of Example 300 and the alkylating agent indicated in parentheses, the following examples were prepared.

Example 301

(MEM chloride) mp: 48°–49° C.; $^1$HNMR (CDCl$_3$, 300 MHz) δ3.40 (s, 3H), 3.75 (m, 2H), 3.85 (m, 2H), 5.42 (s, 2H), 7.20 (m, 1H) and 7.25 (m, 1H); MS: m/z 311.2, (M+1, 100%).

Example 302

Substitution of 3,4-diamlnopyridine for the o-phenylenediamine in the procedure of Example 300A gave the title compound. mp: 220° C (dec) ;$^1$HNMR (DMSO-d$_6$, 300 MHz) δ 7.13 (m, 1H), 7.35 (m, 1H) and 7.95 (m,1H); MS (CDI): m/z 136.0, (M+1, 100%).

Example 303

Alkylation of the compound of Example 302 with cinnamyl bromide was carried out using the procedure describe for Example 302. mp: 141° C.; $^1$NMR (DMSO-d$_6$, 300 NHz) δ4.65 (m, 2H), 6.40 (m, 1H), 6.62 (m, 2H), 7.10–7.40 (m, 6H), 7.50 (m, 1H) and 8.0 (m, 1H); MS (CDI): m/z 368.2, (M+1, 100%).

Example 304

Using the procedure described under Example 305 above, 5-methoxy-2-benzimidazolinone was alkylated with cinnamyl bromide to give the product as an oil. $^1$HNMR (CDCl$_3$, 300 MHz) δ 3.78 (s, 3H), 3.83 (m, 4H), 6.25 (m, 2H), 6.60 (m, 2H), 6.95 (m, 1H) and 7.35 (m, 11H); MS (CDI): m/z 387.3, (M+1, 100%).

Example 305

To a solution of the compound of Example 304 (450 mg, 1.13 mmol) in anhydrous methylene chloride (15 mL) was added boron tribromide (11.3 mmol) at –78° C. under N$_2$. After aqueous work up, the crude residue was chromatographed on silca gel (50% EtOAc:Hexane) to give the desired product (86%). mp: 236° C. (dec); $^1$HNMR (DMSO-d$_6$, 300 MHz) δ4.6 (m, 4H), 6.40 (m, 2H), 6.60 (m, 2H), 6.95 (m, 1H) and 7.20–7.43 (m, 11H); MS (CDI): m/z 383.2, (M+1, 100%).

Example 306

Substitution of 2,3-diaminopyridine for the o-phenylenediamine in the procedure of Example 300A gave 4-aza-2-benzimidazolinone. Alkylation with cinnamyl bromide using the procedure described for Example 300B above provided the title compound in good yield. mp: 237° C. (dec); $^1$HNMR (DMSO-d$_6$, 300 MHz) δ4.85 (m, 2H), 5.30 (m, 2H), 6.38 (m, 1H), 6.55 (m, 1H), 6.60–6-8) (m, 4H), 7.40 (m, 10H), 7.95 (m, 1H) and 8.20 (m, 1H); MS (CDI): M+1=368.2, (M+1, 100%).

Example 307

Alkylation of 1,3-dihydroxy-2-benzimidazolinone (Seng, Synthesis, 1975, 415–422) with benzyl bromide using the procedure described for Example 306B provided the bis-alkylated product. mp: 108° C.: $^1$HNMR (CDCl$_3$, 300 MHz) δ 5.21 (s, 2H), 6.82 (m, 1H), 6.95 (m, 1H), 7.40 (m, 3H) and 7.50 (m,2H); MS (CDI): m/z 364.2, (M+NH$_4$, 100%).

In like manner, using the alkylating agent indicated in parentheses, the following examples were prepared.

Example 308

(2-bromomethylnaphthalene) mp: 189° C.; $^1$HNMR (CDCl$_3$, 300 MHz) δ 5.22 (m, 2H), 6.95 (m, 2H), 7.50 (m, 2H), 7.63 (m, 1H) and 7.95 (, 4H); MS (CDI): m/z 464.2, (M+NH$_4$, 100%).

Example 309

(4-tetrahydropyranyloxymethyl-benzylchloride) (oil) $^1$HNMR (CDCl$_3$, 300 MHz) δ14.5–1.93 (m, 8H), 3.58 (m, 1H), 3.95 (m, 1H), 4.50 (d, 1H, J=10 Hz,) 4.65 (m,1H), 4.80 (d, 1H, J=10 Hz), 5.25 (s, 2H), 6.80 (m, 1H), 6.98 (m,1H), 7.40 (m, 2H) and 7.50 (m, 2H); MS (CDI): m/z 588.2 (M+NH$_4$).

Example 310

The compound of Example 309 was treated with HCl (4.0M in dioxane) followed by basic work up and purification on silica gel ( 50% EtOAc: Hexane) to give the free alcohol; mp: 170° C.; $^1$HNMR (CD$_3$OD, 300 MHz) δ4.60 (s, 2H), 5.23 (s, 2H), 6.85 (m, 1H), 6.95 (m, 1H), 7.40 (m, 2H) and 7.50 (m, 2H); MS (CDI): m/z 424.0, (M+NH$_4$, 100%).

Example 407

1,3,4,6-tetrakis(benzyl)-1H-furo[3,4-d]imidazol-2 (3H)-one

A solution of (4R-cis)-4,5-bis(phenylacetyl)-1,3-bis (benzyl)-2-imidazolidinone (79 mg, 0.16 mmol) and ammonium acetate (25 mg, 0.32 mmol) in acetic acid (2 ml) was refluxed 18 hours. The solution was neutralized with solid potassium carbonate and partitioned between EtOAc/water. The aqueous phase was washed twice with EtOAc. All organic extracts were combined and dried over MgSO$_4$, then concentrated to a brown oil. Further purification was achieved by preparative TLC (silica gel, 30% EtOAc/ hexane) to give the product as a yellow-brown oil, (59 mg, 76% yield). $^1$HNMR (CDCl$_3$) δ7.10–7.44 (m, 10H), 4.99–5.16 (m, 2H) , 4.17–4.29 (m, 3H), 3.59 (d, 1H), 2.54 (m, 1H), 2.07–2.33 (m, 3H), 1.21–1.50 (m, 6H), 0.84–0.93 (m, 6H). MS: 417 (M+1).

Utility

The compounds of formula (I) possess retroviral protease inhibitory activity and are therefore useful as antiviral agents for the treatment of viral diseases. More particularly, the compounds of formula (I) possess HIV protease inhibitory activity and are effective as inhibitors of HIV growth. The protease inhibitory activity of the compounds of the present invention is demonstrated using standard assays of protease activity, as shown, for example, using the assays described below for assaying inhibitors of HIV protease activity. The ability of the compounds of the present invention to inhibit viral growth or infectivity is demonstrated in a standard assay of viral growth or infectivity, as shown, for example, using the assays described below.

The compounds provided by this invention are also useful as standards and reagents in determining the ability of a potential pharmaceutical to inhibit viral replication of HIV protease. These would be provided in commercial kits comprising a compound of this invention.

Since the compounds of the present invention inhibit HIV growth and infectivity, they may be used as HIV antivirals for the inhibition of HIV in a biological sample which contains HIV or is suspected to contain HIV or to be exposed to HIV.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar and "nm" denotes nanomolar. "Sigma" stands for the Sigma-Aldrich Corp. of St. Louis, Mo.

A compound is considered to be active if it has an IC$_{50}$ or Ki value of less than about 1 mM for the inhibition of HIV protease or HIV viral growth or infectivity.

HIV Protease Inhibition Assay (HPLC Method) Materials

Protease: Inclusion bodies of *E. coli* harboring plasmid T1718R with a synthetic gene coding for a single-chain tethered dimer of HIV protease were prepared as described in Cheng et al. *Proc. Natl. Acad. Sci. USA* 1990, 87, 9660. Active protease was prepared as described therein by extraction with 67% acetic acid, dilution 33-fold with water, dialysis against water and then against a "refolding buffer" comprising 20 mM MES, 1 mM dithiothreitol and 10% glycerol, pH 5.5. Protease was stored as a stock preparation at 10 μM in refolding buffer.

Substrate: Peptide of the sequence aminobenzoyl-Ala-Thr-His-Gln-Val-Tyr-Phe(NO$_2$)-Val-Arg-Lys-Ala containing p-nitrophenylalanine (Phe(NO$_2$)), was prepared by solid phase synthesis as previously described (Cheng et al. *Proc. Natl. Acad. Sci. USA* 1990, 87, 9660). Stock solutions of 2 mM substrate were prepared in DMSO.

Inhibitory compounds were dissolved in sufficient DMSO to make 3 mM stock solutions. All further dilutions were prepared in "assay buffer" comprising 1M NaCl, 50 mM MES, pH 5.5, 1 mM EDTA, 1 mM DTT and 20% glycerol. Reactions Enzyme reaction: To a 2 mL screw-cap centrifuge tube were added 50 uL protease (final concentration 0.25 nM) and 0.1 mL inhibitor compound (final concentration 0.1–12,500 nM). After 15 min preincubation at room temperature, the reaction was started by the addition of 0.05 mL substrate (final concentration 5 μM), incubation was carried out at 30° C. for 1 hr. The reaction was stopped by addition of 1 mL of 0.1M ammonium hydroxide solution.

HPLC measurement of product formation: The product (aminobenzoyl-Ala-Thr-His-Gln-Val-Tyr) was separated from substrate on a Pharmacia MonoQ anion exchange column. The injection volume was 0.2 mL. The mobile phases comprised: solution A (20 mM tris HCl, pH 9.0, 0.02% sodium azide, 10% acetonitrile), and solution B (20 mM tris HCl, pH 9.0, 0.02% sodium azide, 0.5M ammonium formate, 10% acetonitrile). The mobile phases were pumped at 1 mL/min, with a gradient from 0 to 30% B in 5 min, 100% B for 4 min to wash the column, and a re-equilibration wash with A for 4 min. The retention time of the product was 3.6 min. Detection with a Shimadzu model RF-535 fluorescence monitor was at 330 nm (excitation) and 430 nm (emission). The Ki was calculated from the formula Ki=I/( ((Km+S−FA*S)/(FA*Km) )−1) where I=inhibitor concentration, S=substrate concentration, FA=fractional activity=cm peak height with inhibitor/cm peak height without inhibitor and Km=Michaelis constant=20 μM.

HIV RNA Assay

DNA Plasmids and in vitro RNA transcripts

Plasmid pDAB 72 containing both gag and pol sequences of BH10 (bp 113–1816) cloned into PTZ 19R was prepared according to Erickson-Viitanen et al. *AIDS Research and Human Retroviruses* 1989, 5, 577. The plasmid was linearized with Bam HI prior to the generation of in vitro RNA transcripts using the Riboprobe Gemini system II kit (Promega) with T7 RNA polymerase. Synthesized RNA was purified by treatment with RNase free DNAse (Promega), phenol-chloroform extraction, and ethanol precipitation. RNA transcripts were dissolved in water, and stored at −70° C. The concentration of RNA was determined from the A$_{260}$. Probes Biotinylated capture probes were purified by HPLC after synthesis on an Applied Biosystems (Foster City, Calif.) DNA synthesizer by addition of biotin to the 5' terminal end of the oligonucleotide, using the biotin-phosphoramidite reagent of Cocuzza, *Tet. Lett.* 1989, 30, 6287. The gag biotinylated capture probe (5-biotin-CTAGCTCCCTGCTTGCCCATACTA 3') was complementary to nucleotides 839–912 of HXB2 and the pol biotinylated capture probe (5'-biotin- CCCTATCATTTTTGGTTTCCAT 3') was complementary to nucleotides 2374–2395 of HXB2. Alkaline phosphatase conjugated oligonucleotides used as reporter probes were prepared by Syngene (San Diego, Calif.). The pol reporter probe (5' CTGTCTTACTTTGATAAAACCTC 3') was complementary to nucleotides 2403–2425 of HXB2. The gag reporter probe (5' CCCAGTATTTGTCTACAGCCT-TCT 3') was complementary to nucleotides 950–973 of HXB2. All nucleotide positions are those of the GenBank Genetic Sequence Data Bank as accessed through the Genetics Computer Group Sequence Analysis Software Package (Devereau *Nucleic Acids Research* 1984, 12, 387). The reporter probes were prepared as 0.5 µM stocks in 2× SSC (0.3M NaCl, 0.03M sodium citrate), 0.05M Tris pH 8.8, 1 mg/mL BSA. The biotinylated capture probes were prepared as 100 µM stocks in water.

Streptavidin coated plates

Nunc-immunomodule microtiter plate strips were coated by addition of 200 µL of streptavidin (30 µg/mL, Scripps, La Jolla, Calif.) in freshly prepared 10 mM sodium carbonate (pH 9.6). Plates were incubated overnight at 4° C. Streptavidin solution was aspirated from the wells and a blocking buffer composed of phosphate buffered saline (PBS), 20 mg/mL bovine serum albumin (crystalline, nuclease and protease free, Calbiochem) and 100 mg/mL lactose (Sigma) was added to the plates for 3 hrs at room temperature. Blocking buffer was removed from the wells, which were allowed to dry overnight at room temperature and subsequently stored at 4° C. in zip lock bags with desiccant. For the majority of the compound evaluation experiments, strept-avidin coated plates were obtained from Du Pont Biotechnology Systems (Boston, Mass.).

Cells and virus stocks

MT-2, CEM, and H9 cells were maintained in RPMI 1640 supplemented with 5% fetal calf serum (FCS), 2 mM L-glutamine and 50 µg/mL gentamycin, all from Gibco. Laboratory strains of HIV-1 (RF, MN and IIIB) were propagated in H9 cells in the same medium. Virus stocks were prepared approximately 1 month after acute infection of H9 cells by clarification of the tissue culture medium and storage of aliquots at –70° C. Infectious titers of HIV-1 (RF) stocks were 1–3×10$^7$ PFU (plaque forming units)/mL as measured by plaque assay on MT-2 cells (see below). Each aliquot of virus stock used for infection was thawed only once. In some cases, infected H9 cells were shifted to Dulbecco's modified Eagle's medium 3–10 days before collection of virus in order to generate virus stocks in medium with low biotin content. Clinical isolates of HIV that had been passaged once in MT-2 cells were used to infect fresh MT-2 cells in RPMI medium. Three days after infection, cells were pelleted, resuspended and culture continued in Dulbecco's modified Eagle's medium as above. Virus stocks of clinical isolates were prepared 10–15 days after infection when cytopathic effects were apparent in the culture.

For evaluation of antiviral efficacy, cells to be infected were subcultured one day prior to infection. On the day of infection, cells were resuspended at 5×10$^5$ cells/mL in RPMI 1640, 5% FCS for bulk infections or at 2×10$^6$/mL in either Dulbecco's modified Eagles medium, or RPMI 1640 medium minus biotin (Gibco, custom formulation) with 5% FCS for infection in microtiter plates. Virus was added and culture continued for 3 days at 37° C. In some experiments, virus was removed after an initial adsorption period.

Preparation of HIV-1 infected cell lysates

HIV-1 infected cells were pelleted by centrifugation. After removal of the supernatant the cells were resuspended at a concentration of 1×10$^7$ cells/mL in 5M guanidinium isothiocyanate solution (GED: 5M guanidinium isothiocyanate (Sigma), 0.1M EDTA, 10% dextran sulfate). Alternately, cells grown in biotin free tissue culture medium were mixed with 5M GED to a final concentration of 3M guanidinium isothiocyanate, 0.06M EDTA and 6% dextran sulfate.

HIV RNA assay

Cell lysates or purified RNA in 3M or 5M GED were mixed with 5M GED and capture probe to a final guanidinium isothiocyanate concentration of 3M and a final biotin oligonucleotide concentration of 30 nM. Hybridization was carried out in sealed microfuge tubes or in sealed U bottom 96 well tissue culture plates (Nunc or Costar) for 16–20 hours at 37° C. RNA hybridization reactions were diluted three-fold with deionized water to a final guanidinium isothiocyanate concentration of 1M and aliquots (150 µL) were transferred to streptavidin coated microtiter plates wells. Binding of capture probe and capture probe-RNA hybrid to the immobilized streptavidin was allowed to proceed for 2 hours at room temperature, after which the plates were washed 6 times with DuPont ELISA plate wash buffer (phosphate buffered saline(PBS), 0.05% Tween 20.) A second hybridization of reporter probe to the immobilized complex of capture probe and hybridized target RNA was carried out in the washed streptavidin coated well by addition of 120 µl of a hybridization cocktail containing 4× SSC, 0.66% Triton×100, 6.66% deionized formamide, 1 mg/mL BSA and 5 nM reporter probe. After hybridization for one hour at 37° C., the plate was again washed 6 times. Immobilized alkaline phosphatase activity was detected by addition of 100 µL of 0.2 mM 4-methylumbelliferyl phosphate (MUBP, JBL Scientific) in buffer δ(2.5M diethanolamine pH 8.9 (JBL Scientific), 10 mM MgCl$_2$, 5 mM zinc acetate dihydrate and 5 mM N-hydroxyethyl-ethylene-diamine-triacetic acid). The plates were incubated at 37° C. Fluorescence at 450 nM was measured using a microplate fluorometer (Dynateck) exciting at 365 nm.

Microplate based compound evaluation in HIV-1 infected MT-2 cells

Compounds to be evaluated were dissolved in DMSO and diluted in culture medium to twice the highest concentration to be tested and a maximum DMSO concentration of 2%. Further three-fold serial dilutions of the compound in culture medium were performed directly in U bottom microtiter plates (Nunc). After compound dilution, MT-2 cells (50 µL) were added to a final concentration of 5×10$^5$ per mL (1×10$^5$ per well). Cells were incubated with compounds for 30 minutes at 37° C. in a CO$_2$ incubator. For evaluation of antiviral potency, an appropriate dilution of HIV-1 (RF) virus stock (50 µL) was added to culture wells containing cells and dilutions of the test compounds. The final volume in each well was 200 µL. Eight wells per plate were left uninfected with 50 µL of medium added in place of virus while eight wells were infected in the absence of any antiviral compound. For evaluation of compound toxicity, parallel plates were cultured without virus infection.

After 3 days of culture at 37° C. in a humidified chamber inside a CO$_2$ incubator, all but 25 µL of medium/well was removed from the HIV infected plates. Thirty seven µL of 5M GED containing biotinylated capture probe was added to the settled cells and remaining medium in each well to a final concentration of 3M GED and 30 nM capture probe. Hybridization of the capture probe to HIV RNA in the cell lysate was carried out in the same microplate well used for virus culture by sealing the plate with a plate sealer (Costar), and incubating for 16–20 hrs in a 37° C. incubator. Distilled water was then added to each well to dilute the hybridization reaction three-fold and 150 μL of this diluted mixture was transferred to a streptavidin coated microtiter plate. HIV RNA was quantitated as described above. A standard curve, prepared by adding known amounts of pDAB 72 in vitro RNA transcript to wells containing lysed uninfected cells, was run on each microtiter plate in order to determine the amount of viral RNA made during the infection.

In order to standardize the virus inoculum used in the evaluation of compounds for antiviral activity, dilutions of virus were selected which resulted in an $IC_{90}$ value (concentration of compound required to reduce the HIV RNA level by 90%) for dideoxycytidine (ddC) of 0.2 μg/mL. $IC_{90}$ values of other antiviral compounds, both more and less potent than ddC, were reproducible using several stocks of HIV-1 (RF) when this procedure was followed. This concentration of virus corresponded to ~$3 \times 10^5$ PFU (measured by plaque assay on MT-2 cells) per assay well and typically produced approximately 75% of the maximum viral RNA level achievable at any virus inoculum. For the HIV RNA assay, $IC_{90}$ values were determined from the percent reduction of net signal (signal from infected cell samples minus signal from uninfected cell samples) in the RNA assay relative to the net signal from infected, untreated cells on the same culture plate (average of eight wells). Valid performance of individual infection and RNA assay tests was judged according to three criteria. It was required that the virus infection should result in an RNA assay signal equal to or greater than the signal generated from 2 ng of pDAB 72 in vitro RNA transcript. The $IC_{90}$ for ddC, determined in each assay run, should be between 0.1 and 0.3 μg/mL. Finally, the plateau level of viral RNA produced by an effective protease inhibitor should be less than 10% of the level achieved in an uninhibited infection.

For antiviral potency tests, all manipulations in microtiter plates, following the initial addition of 2× concentrated compound solution to a single row of wells, were performed using a Perkin Elmer/Cetus ProPette.

TABLE 1

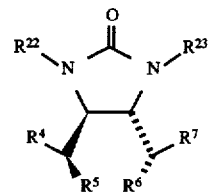

| Ex. No. | $R^{22}=R^{23}$ | $R^4=R^7$ | $R^5$ | $R^6$ | MS M+H or (mp °C.) |
|---|---|---|---|---|---|
| 1 | 3-benzyloxybenzyl | benzyl | F | F | 723 |
| 2 | 3-hydroxybenzyl | benzyl | F | F | 543 |
| 3 | cyclopropylmethyl | benzyl | F | F | 439 |
| 4 | 2-naphthylmethyl | benzyl | F | F | 611 |
| 5 | allyl | benzyl | F | F | 411 |
| 6* | allyl | benzyl | F | F | 411 |
| 7 | 3-carbomethoxybenzyl | benzyl | H | OH | 607 |
| 8 | 3-carbomethoxybenzyl | benzyl | H | Br | 688 (M+NH$_4$)$^+$ |
| 9 | 3-carbomethoxybenzyl | benzyl | H | H | 591 |
| 10 | 3-hydroxymethylbenzyl | benzyl | H | OH | 551 |
| 11 | 3-hydroxymethylbenzyl | benzyl | H | H | 535 |
| 12 | 3-carbomethoxybenzyl | phenyl | H | H | 563 |
| 13 | 3-hydroxymethylbenzyl | phenyl | H | H | 507 |
| 14 | 3-(H$_2$NC(=NOH))benzyl | benzyl | H | H | 591 |
| 15 | 3-aminocarbonylbenzyl | benzyl | F | F | |

TABLE 1-continued

| Ex. No. | $R^{22}=R^{23}$ | $R^4=R^7$ | $R^5$ | $R^6$ | MS M+H or (mp °C.) |
|---|---|---|---|---|---|
| 16 | 3-N,N-dimethylamino-carbonylbenzyl | benzyl | F | F | |
| 17 | 3-(2-hydroxymethylamino-carbonyl)benzyl | benzyl | F | F | |
| 18 | 5-indazolylmethyl | benzyl | F | F | |
| 19 | 6-indazolylmethyl | benzyl | F | F | |
| 20 | 3-aminoindazol-5-ylmethyl | benzyl | F | F | |
| 21 | 3-(dimethylamino)indazol-5-ylmethyl | benzyl | F | F | |
| 22 | 3-methoxy-indazol-5-ylmethyl | benzyl | F | F | |
| 23 | 3-(phenoxymethyl)indazol-5-ylmethyl | benzyl | F | F | |
| 24 | indazolinon-5-ylmethyl | benzyl | F | F | |
| 25 | indazolinon-6-ylmethyl | benzyl | F | F | |
| 26 | benzoxazolinon-5-ylmethyl | benzyl | F | F | |
| 27 | benzoxazolinon-6-ylmethyl | benzyl | F | F | |
| 28 | 5-benzisoxazolyl-5-methyl | benzyl | F | F | |
| 29 | 3-methylbenzIsoxazol-5-ylmethyl | benzyl | F | F | |
| 30 | 3-aminobenzisoxazol-5-ylmethyl | benzyl | F | F | |
| 31 | 3-(dimethylamino)benzisoxazol-5-ylmethyl | benzyl | F | F | |
| 32 | 5-benzisothiazolylmethyl | benzyl | F | F | |
| 33 | 3-aminobenzisothiazol-5-ylmethyl | benzyl | F | F | |
| 34 | 3-(dimethylamino)benziso-thiazol-5-ylmethyl | benzyl | F | F | |
| 35 | 3-(diazol-3'-yl)benzyl | benzyl | F | F | |
| 36 | 3-(4'-methyldiazol-3'-yl)benzyl | benzyl | F | F | |
| 37 | 3-(4',5'-dimethyldiazol-3'-yl)benzyl | benzyl | F | F | |
| 38 | 3-(4'-aminodiazol-3'-yl)benzyl | benzyl | F | F | |
| 39 | 3-(4'-(dimethylamino)diazol-3'-yl)benzyl | benzyl | F | F | |
| 40 | 3-oxazol-3'-ylbenzyl | benzyl | F | F | |
| 41 | 3-(4'-methyloxazol-3'-yl)benzyl | benzyl | F | F | |
| 42 | 3-(4',5'-dimethyloxazol-3'-yl)benzyl | benzyl | F | F | |
| 43 | 3-(4'-aminooxazol-3'-yl)benzyl | benzyl | F | F | |
| 44 | 3-(5'-(dimethylamino)oxazol-3'-yl)benzyl | benzyl | F | F | |
| 45 | 3-isoxazol-3'-ylbenzyl | benzyl | F | F | |
| 46 | 3-(4'-ethylisoxazol-3'-yl)benzyl | benzyl | F | F | |
| 47 | 3-(4',5'-diethylisoxazol-3'-yl)benzyl | benzyl | F | F | |
| 48 | 3-(4'-aminoisoxazol-3'-yl)benzyl | benzyl | F | F | |
| 49 | 3-(5'-(diethylamino)isoxazol-3'-yl)benzyl | benzyl | F | F | |
| 50 | 3-(2-triazolyl)benzyl | benzyl | F | F | |
| 51 | 3-(5-ethyltriazol-2-yl)benzyl | benzyl | F | F | |
| 52 | 3-(5-aminotriazol-2-yl)benzyl | benzyl | F | F | |
| 53 | 3-(5-(ethylamino)triazol-2-yl)benzyl | benzyl | F | F | |
| 54 | 3-triazol-3'-ylbenzyl | benzyl | F | F | |
| 55 | 3-(5'-aminotriazol-3'-yl)benzyl | benzyl | F | F | |
| 56 | 3-(5'-(ethylamino)triazol-3'-yl)benzyl | benzyl | F | F | |
| 57 | 3-(2-imidazolyl)benzyl | benzyl | F | F | |
| 58 | 3-(4-(methylamino)imidazol-2-yl)benzyl | benzyl | F | F | |
| 59 | 3-(4-(dimethylamino)imidazol-2-yl)benzyl | benzyl | F | F | |

TABLE 1-continued

| Ex. No. | $R^{22} = R^{23}$ | $R^4 = R^7$ | $R^5$ | $R^6$ | MS M+H or (mp °C.) |
|---|---|---|---|---|---|
| 60 | 3-(2-imidazolyl-aminocarbonyl)-benzyl | benzyl | F | F | |
| 61 | 3-(4,5-dimethylimidazol-2-yl-aminocarbonyl)benzyl | benzyl | F | F | |
| 62 | 3-(4-(diethylamino)imidazol-2-yl-aminocarbonyl)benzyl | benzyl | F | F | |
| 63 | 3-(5-aminoimidazol-2-yl-aminocarbonyl)benzyl | benzyl | F | F | |
| 64 | 3-(5-(dimethylamino)imidazol-2-yl-aminocarbonyl)benzyl | benzyl | F | F | |
| 65 | 3-(2-pyridyl-aminocarbonyl)-benzyl | benzyl | F | F | |
| 66 | 3-(3'-pyridyl-aminocarbonyl)-benzyl | benzyl | F | F | |
| 67 | 3-(4-pyridyl-aminocarbonyl)-benzyl | benzyl | F | F | |
| 68 | 3-(5-ethylthiadiazol-2-yl-aminocarbonyl)benzyl | benzyl | F | F | |
| 69 | 3-(5-t-butylthiadiazol-2-yl-aminocarbonyl)benzyl | benzyl | F | F | |
| 70 | 3-(5-aminothiadiazol-2-yl-aminocarbonyl)benzyl | benzyl | F | F | |
| 71 | 3-(5-(diethylamino)thiadiazol-2-yl-aminocarbonyl)benzyl | benzyl | F | F | |
| 72 | 3-(2-thiazolyl-aminocarbonyl)-benzyl | benzyl | F | F | |
| 73 | 3-(5-methylthiazol-2-yl-aminocarbonyl)benzyl | benzyl | F | F | |
| 74 | 3-(4,5-dimethylthiazol-2-yl-aminocarbonyl)benzyl | benzyl | F | F | |
| 75 | 3-(4-aminothiazol-2-yl-aminocarbonyl)benzyl | benzyl | F | F | |
| 76 | 3-(2-triazolyl-aminocarbonyl)-benzyl | benzyl | F | F | |
| 77 | 3-(5-methyltriazol-2-yl-aminocarbonyl)benzyl | benzyl | F | F | |
| 78 | 3-(5-aminotriazol-2-yl-aminocarbonyl)benzyl | benzyl | F | F | |
| 79 | 3-(5-(diethylamino)triazol-2-yl-aminocarbonyl)benzyl | benzyl | F | F | |

*Enantiomer of 5

TABLE 2

| Ex. No. | $R^{22} = R^{23}$ | $R^{24a}$ | $R^4 = R^7$ | $R^5 = R^6$ |
|---|---|---|---|---|
| 80 | 3-benzyloxybenzyl | $OCH_3$ | benzyl | F |
| 81 | 3-hydroxybenzyl | $OCH_3$ | benzyl | F |
| 82 | cyclopropylmethyl | $OCH_3$ | benzyl | F |

TABLE 2-continued

| Ex. No. | $R^{22} = R^{23}$ | $R^{24a}$ | $R^4 = R^7$ | $R^5 = R^6$ |
|---|---|---|---|---|
| 83 | 2-naphthylmethyl | $OCH_3$ | benzyl | F |
| 84 | 3-carbomethoxybenzyl | $OCH_3$ | benzyl | F |
| 85 | 3-hydroxymethylbenzyl | $OCH_3$ | benzyl | F |
| 86 | 3-($H_2NC(=NOH)$)benzyl | $OCH_3$ | benzyl | F |
| 87 | 5-(3-methylindazolyl)methyl | $OCH_3$ | benzyl | F |
| 88 | 5-(3-aminoindazolyl)methyl | $OCH_3$ | benzyl | F |
| 89 | 3-(N-thiazolylamino-carbonyl)benzyl | $OCH_3$ | benzyl | F |

TABLE 3

| Ex. No. | T | $R^{22} = R^{23}$ | $R^4 = R^7$ |
|---|---|---|---|
| 101 | C=O | cyclopropylmethyl | benzyl |
| 102 | C=O | n-butyl | benzyl |
| 103 | C=O | benzyl | benzyl |
| 104 | C=O | 3-hydroxybenzyl | benzyl |
| 105 | C=O | 4-hydroxymethyl benzyl | benzyl |
| 106 | C=O | 2-naphthylmethyl | benzyl |
| 107 | C=O | 3-($H_2NC(=NOH)$)benzyl | benzyl |
| 108 | C=O | 3-pyrazolylbenzyl | benzyl |
| 109 | C=O | 5-indazolyl | benzyl |
| 110 | C=O | 6-hydroxyhexyl | benzyl |
| 111 | C=O | 5-indazolylmethyl | benzyl |
| 112 | C=O | 5-(3-methylindazolyl)methyl | benzyl |
| 113 | C=O | 5-(3-aminoindazolyl)methyl | benzyl |
| 114 | C=O | 3-(N-thiazolylamino-carbonyl)benzyl | benzyl |
| 115 | C=O | 3-(N-thiadiazolylamino-carbonyl)benzyl | benzyl |
| 116 | $SO_2$ | cyclopropylmethyl | benzyl |
| 117 | $SO_2$ | n-butyl | benzyl |
| 118 | $SO_2$ | benzyl | benzyl |
| 119 | $SO_2$ | 3-hydroxybenzyl | benzyl |
| 120 | $SO_2$ | 4-hydroxymethyl benzyl | benzyl |
| 121 | $SO_2$ | 2-naphthylmethyl | benzyl |
| 122 | $SO_2$ | 3-($H_2NC(=NOH)$)benzyl | benzyl |
| 123 | $SO_2$ | 3-pyrazolylbenzyl | benzyl |
| 124 | $SO_2$ | 5-indazolyl | benzyl |
| 125 | $SO_2$ | 6-hydroxyhexyl | benzyl |
| 126 | $SO_2$ | 5-indazolylmethyl | benzyl |
| 127 | $SO_2$ | 5-(3-methylindazolyl)-methyl | benzyl |
| 128 | $SO_2$ | 5-(3-aminoindazolyl)-methyl | benzyl |
| 129 | $SO_2$ | 3-(N-thiazolylamino-carbonyl)benzyl | benzyl |
| 130 | $SO_2$ | 3-(N-thiadiazolylamino-carbonyl)benzyl | benzyl |

TABLE 4a

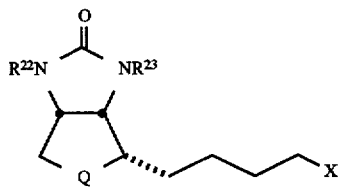

| Ex. No | $R^{22} = R^{23}$ | Q | X | MS M+H (M+NH$_4$) |
|---|---|---|---|---|
| 201 | 3-BrC$_6$H$_5$CH$_2$— | S | CO$_2$H | 583 |
| 202 | 3-BrC$_6$H$_5$CH$_2$— | S | CH$_2$OH | 569 |
| 203 | 3-BrC$_6$H$_5$CH$_2$— | SO$_2$ | CO$_2$Me | 646 |
| 204 | 3-BrC$_6$H$_5$CH$_2$— | SO$_2$ | CH$_2$OH | 618 |
| 205 | 3-BrC$_6$H$_5$CH$_2$— | S | 3-BrC$_6$H$_5$CH$_2$O$_2$C— | 753 |
| 206 | 3-CH$_3$COC$_6$H$_5$CH$_2$— | S | 3-CH$_3$COC$_6$H$_5$CH$_2$CO$_2$— | 641 |
| 207 | 3-CH$_3$COC$_6$H$_5$CH$_2$— | S | CH$_2$OH | 512 |
| 208 | 3-(CH$_3$CH(OH))—C$_6$H$_5$CH$_2$— | S | CO$_2$H | 509 |
| 209 | 3-(CH$_3$C(=NOH))—C$_6$H$_5$CH$_2$— | S | 3-(CH$_3$C(=NOH))—C$_6$H$_5$CH$_2$CO— | |
| 210 | 3-(CH$_3$CH(OH))—C$_6$H$_5$CH$_2$ | S | CH$_2$OH | |
| 211 | 3-BrC$_6$H$_5$CH$_2$— | S | CO$_2$Me | 597 |
| 212 | 3-(1-SEM-5-pyrazolyl)-C$_6$H$_5$CH$_2$— | S | CO$_2$Me | 831 |
| 213 | 3-pyrazolyl-C$_6$H$_5$CH$_2$ | S | CO$_2$Me | 571 |
| 214 | 3-BrC$_6$H$_5$CH$_2$ | SO$_2$ | 3-BrC$_6$H$_5$CH$_2$ | 779.9503 |
| 215 | 3-BrC$_6$H$_5$CH$_2$ | SO | 3-BrC$_6$H$_5$CH$_2$ | 763.9559 |

TABLE 4b

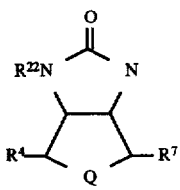

| Ex. No. | $R^{22} = R^{23}$ | Q | $R^4 = R^7$ |
|---|---|---|---|
| 216 | 3-bromobenzyl | O | benzyl |
| 217 | 3-bromobenzyl | NH | benzyl |
| 218 | 3-bromobenzyl | NOCH$_3$ | benzyl |
| 219 | 3-aminocarbonylbenzyl | O | benzyl |
| 220 | 3-aminocarbonylbenzyl | NH | benzyl |
| 221 | 3-aminocarbonylbenzyl | NOCH$_3$ | benzyl |
| 222 | 5-indazolymethyl | O | benzyl |
| 223 | 5-indazolymethyl | NH | benzyl |
| 224 | 5-indazolymethyl | NOCH$_3$ | benzyl |
| 225 | 3-(2-imidazolyl)benzyl | O | benzyl |
| 226 | 3-(2-imidazolyl)benzyl | NH | benzyl |
| 227 | 3-(2-imidazolyl)benzyl | NOCH$_3$ | benzyl |
| 228 | 3-(2-imidazolylaminocarbonyl)-benzyl | O | benzyl |
| 229 | 3-(2-imidazolylaminocarbonyl)-benzyl | NH | benzyl |
| 230 | 3-(2-imidazolylaminocarbonyl)-benzyl | NOCH$_3$ | benzyl |
| 231 | 3-(4'-pyridyl-aminocarbonyl)-benzyl | O | benzyl |
| 232 | 3-(4'-pyridyl-aminocarbonyl)-benzyl | NH | benzyl |
| 233 | 3-(4'-pyridyl-aminocarbonyl)-benzyl | NOCH$_3$ | benzyl |

TABLE 5

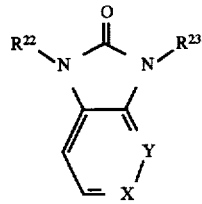

| Ex. No. | $R^{22} = R^{23}$ | Y | X | mp °C. | M+H; (M+NH$_4$) |
|---|---|---|---|---|---|
| 300 | n-octyl | C | C | | 359.4 |
| 301 | methoxyethoxy-methyl | C | C | 48–49 | 311.2 |
| 302 | —H | C | N | >220 d | 136.0 |
| 303 | —CH$_2$CH=CH—Ph | C | N | 141 | 368.2 |
| 304 | —CH$_2$CH=CH—Ph | C | COMe | | 387.3 |
| 305 | —CH$_2$CH=CH—Ph | C | COH | >230 d | 383.2 |
| 306 | —CH$_2$CH=CH—Ph | N | C | >237 d | 368.2 |
| 307 | benzyloxy | C | C | 108 | 364.2 |
| 308 | β-naphthylmethoxy | C | C | 189 | 464.2 |
| 309 | (4-tetrahydropyranyloxy-methyl)phenylmethoxy | C | C | | 588.2 |
| 310 | 4-hydroxymethylphenyl-methoxy | C | C | 170 | 424.0 |
| 311 | cyclopropylmethyl | C | C | | |
| 312 | n-butyl | C | C | | |
| 313 | benzyl | C | C | | |
| 314 | 3-hydroxybenzyl | C | C | | |
| 315 | 4-hydroxymethylbenzyl | C | C | | |
| 316 | 2-naphthylmethyl | C | C | | |
| 317 | 3-(H$_2$NC(=NOH))benzyl | C | C | | |
| 318 | 3-pyrazolylbenzyl | C | C | | |
| 319 | 5-indazolyl | C | C | | |
| 320 | 6-hydroxyhexyl | C | C | | |
| 321 | 5-indazolylmethyl | C | C | | |
| 322 | 5-(3-methylindazolyl)methyl | C | C | | |
| 323 | 5-(3-aminoindazolyl)methyl | C | C | | |
| 324 | 3-(N-thiazolylaminocarbonyl)-benzyl | C | C | | |
| 325 | 3-(N-thiadiazolylamino-carbonyl)benzyl | C | C | | |

TABLE 6

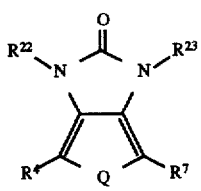

| Ex. No. | $R^{22} = R^{23}$ | $R^4 = R^7$ | Q |
|---|---|---|---|
| 401 | benzyl | benzyl | NOH |
| 402 | cyclopropylmethyl | benzyl | NOH |
| 403 | benzyl | phenethyl | NOH |
| 404 | benzyl | phenylpropyl | NOH |
| 405 | benzyl | n-butyl | NOH |
| 406 | benzyl | benzyl | NH |
| 407 | benzyl | benzyl | O |
| 408 | benzyl | benzyl | N(O)CH$_3$ |
| 409 | benzyl | benzyl | NCH$_2$CH$_2$OH |
| 410 | benzyl | benzyl | S |
| 411 | benzyl | benzyl | S(O) |
| 412 | benzyl | benzyl | SO$_2$ |
| 413 | propyl | benzyl | NOH |
| 414 | propyl | benzyl | NH |
| 415 | propyl | benzyl | O |
| 416 | propyl | benzyl | N(O)CH$_3$ |
| 417 | propyl | benzyl | NCH$_2$CH$_2$OH |

TABLE 6-continued

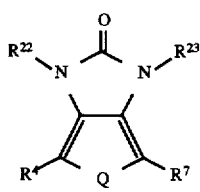

| Ex. No. | $R^{22} = R^{23}$ | $R^4 = R^7$ | Q |
|---|---|---|---|
| 418 | propyl | benzyl | S |
| 419 | propyl | benzyl | S(O) |
| 420 | propyl | benzyl | $SO_2$ |
| 421 | allyl | benzyl | NOH |
| 422 | allyl | benzyl | NH |
| 423 | allyl | benzyl | O |
| 424 | allyl | benzyl | $N(O)CH_3$ |
| 425 | allyl | benzyl | $NCH_2CH_2OH$ |
| 426 | allyl | benzyl | S |
| 427 | allyl | benzyl | S(O) |
| 428 | allyl | benzyl | $SO_2$ |
| 429 | 3-hydroxybenzyl | benzyl | NOH |
| 430 | 3-hydroxybenzyl | benzyl | NH |
| 431 | 3-hydroxybenzyl | benzyl | O |
| 432 | 3-hydroxybenzyl | benzyl | $N(O)CH_3$ |
| 433 | 3-hydroxybenzyl | benzyl | $NCH_2CH_2OH$ |
| 434 | 3-hydroxybenzyl | benzyl | S |
| 435 | 3-hydroxybenzyl | benzyl | S(O) |
| 436 | 3-hydroxybenzyl | benzyl | $SO_2$ |
| 437 | 3-carbomethoxybenzyl | benzyl | NOH |
| 438 | 3-carbomethoxybenzyl | benzyl | NH |
| 439 | 3-carbomethoxybenzyl | benzyl | O |
| 440 | 3-carbomethoxybenzyl | benzyl | $N(O)CH_3$ |
| 441 | 3-carbomethoxybenzyl | benzyl | $NCH_2CH_2OH$ |
| 442 | 3-carbomethoxybenzyl | benzyl | S |
| 443 | 3-carbomethoxybenzyl | benzyl | S(O) |
| 444 | 3-carbomethoxybenzyl | benzyl | $SO_2$ |
| 445 | 5-indazolylmethyl | benzyl | NOH |
| 446 | 5-indazolylmethyl | benzyl | NH |
| 447 | 5-indazolylmethyl | benzyl | O |
| 448 | 5-indazolylmethyl | benzyl | $N(O)CH_3$ |
| 449 | 5-indazolylmethyl | benzyl | $NCH_2CH_2OH$ |
| 450 | 5-indazolylmethyl | benzyl | S |
| 451 | 5-indazolylmethyl | benzyl | S(O) |
| 452 | 5-indazolylmethyl | benzyl | $SO_2$ |
| 453 | 3-(2-imidazolyl)benzyl | benzyl | NOH |
| 454 | 3-(2-imidazolyl)benzyl | benzyl | NH |
| 455 | 3-(2-imidazolyl)benzyl | benzyl | O |
| 456 | 3-(2-imidazolyl)benzyl | benzyl | $N(O)CH_3$ |
| 457 | 3-(2-imidazolyl)benzyl | benzyl | $NCH_2CH_2OH$ |
| 458 | 3-(2-imidazolyl)benzyl | benzyl | S |
| 459 | 3-(2-imidazolyl)benzyl | benzyl | S(O) |
| 460 | 3-(2-imidazolyl)benzyl | benzyl | $SO_2$ |
| 461 | 3-(4'pyridylaminocarbonyl)-benzyl | benzyl | NOH |
| 462 | 3-(4'pyridylaminocarbonyl)-benzyl | benzyl | NH |
| 463 | 3-(4'pyridylaminocarbonyl)-benzyl | benzyl | O |
| 464 | 3-(4'pyridylaminocarbonyl)-benzyl | benzyl | $N(O)CH_3$ |
| 465 | 3-(4'pyridylaminocarbonyl)-benzyl | benzyl | $NCH_2CH_2OH$ |
| 466 | 3-(4'pyridylaminocarbonyl)-benzyl | benzyl | S |
| 467 | 3-(4'pyridylaminocarbonyl)-benzyl | benzyl | S(O) |
| 468 | 3-(4'pyridylaminocarbonyl)-benzyl | benzyl | $SO_2$ |
| 469 | 3-(N-thiazolylaminocarbonyl)-benzyl | | |

Dosage and Formulation

The antiviral compounds of this invention can be administered as treatment for viral infections by any means that produces contact of the active agent with the agent's site of action, i.e., the viral protease, in the body of a mammal. They can be administered by any conventional means available for use in conjunction with pharmaceuticals, either as individual therapeutic agents or in a combination of therapeutic agents. They can be administered alone, but preferably are administered with a pharmaceutical carrier selected on the basis of the chosen route of administration and standard pharmaceutical practice.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg.

Dosage forms of compositions suitable for administration contain from about 1 mg to about 100 mg of active ingredient per unit. In these pharmaceutical compositions the active ingredient will ordinarily be present in an amount of about 0.5–95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, supra, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil is prepared and injected by means of a positive displacement pump into gelatin to form soft gelatin capsules containing 100 mg of the active ingredient. The capsules are washed and dried.

Tablets

A large number of tablets were prepared by conventional procedures so that the dosage unit was 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Obviously, numerous modifications and variations of the present invention are possible in light of the above teachings. It is therefore to be understood that within the scope of the appended claims, the invention may be practiced otherwise that as specifically described herein.

What is claimed as new and desired to be secured by Letter Patent of United States is:

1. A compound of formula (IIa)

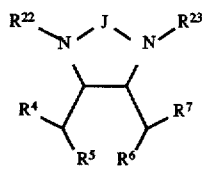

or pharmaceutically acceptable salt or prodrug form thereof, wherein;

J is C=O or C=S;

$R^4$ and $R^7$ are independently selected from the following: —$CO_2R^{13}$; —$NR^{11}R^{13}$;

$C_1$-$C_6$ alkyl substituted with 0–3 $R^{11}$;

$C_2$-$C_6$ alkenyl substituted with 0–3 $R^{11}$;

$C_2$-$C_6$ alkynyl substituted with 0–3 $R^{11}$; or a $C_5$-$C_{10}$ carbocyclic ring system substituted with 0–3 $R^{11}$ or $R^{12}$;

$R^5$ and $R^6$ are independently selected from the following: hydrogen, halogen, —$N(R^{20})_2$, —$SR^{20}$, —$OR^{20}$, =O, or $CH_2OH$;

$R^{11}$ is selected from the following:

hydrogen; keto; halogen; cyano; —$NR^{13}R^{14}$; —$CO_2R^{13}$; —$OC(=O)R^{13}$; —$OR^{13}$; —$S(O)_mR^{13}$; —$C(=O)$ $NR^{13}R^{14}$; —$SO_2NR^{13}R^{14}$; $C_2$-$C_4$ alkenyl; nitro; formyl; $C_1$-$C_4$ haloalkyl; $C_1$-$C_4$ haloalkoxy; $C_1$-$C_4$ alkyl substituted with 0–2 $R^{12}$;

$C_{2-6}$ alkoxy-$C_{2-6}$ alkyl substituted with 0–2 $R^{12}$;

a $C_5$-$C_{10}$ carbocyclic residue substituted with 0–3 $R^{12}$;

a 5- to 10-membered heterocyclic ring system containing 1 to 3 heteroatoms independently selected from oxygen, nitrogen or sulfur, said heterocyclic ring system being substituted with 0–3 $R^{12}$;

$R^{11a}$ is selected from the following:

halogen; cyano; —$NH_2$; —$NH(C_1$-$C_3$ alkyl); —$CO_2H$; —$OC(=O)(C_1$-$C_3$ alkyl); —$OH$; —$C(=O)NH_2$; —$SO_2NH_2$; $C_3$-$C_6$ cycloalkyl; $C_3$-$C_6$ cycloalkylmethyl; phenoxy; benzyloxy; nitro; $C_3$-$C_6$ cycloalkoxy; $C_1$-$C_4$ alkyl substituted with —$NH_2$; $C_1$-$C_4$ hydroxyalkyl; $C_1$-$C_4$ haloalkyl; $C_1$-$C_4$ haloalkoxy; $C_1$-$C_4$ alkoxycarbonyl; $C_1$-$C_4$ alkylcarbonyloxy; $C_1$-$C_4$ alkylcarbonyl; $C_1$-$C_4$ alkylcarbonylamino; 2-(1-morpholino)ethoxy;

$R^{12}$, when a substituent on carbon, is selected from the following:

phenyl; halogen; hydroxy; nitro; cyano; $C_1$-$C_4$ alkyl substituted with 0–2 $OR^{13}$, $SR^{13}$, or $NR^{11}R^{13}$; $C_3$-$C_6$ cycloalkylmethyl; $C_1$-$C_4$ alkoxy; hydroxamic acid; hydrazide; boronic acid; sulfonamide; formyl; $C_3$-$C_6$ cycloalkoxy; —$OR^{13}$; —$NR^{13}R^{14}$; $C_1$-$C_4$ alkyl substituted with —$NR^{13}R^{14}$; $C_{1-6}$ alkoxy $C_{1-6}$ alkyl; $C_1$-$C_4$ hydroxyalkyl; $C_1$-$C_4$ haloalkyl; $C_1$-$C_4$ alkoxycarbonyl; $C_1$-$C_4$ alkylcarbonyloxy; $C_1$-$C_4$ alkylcarbonyl; $C_1$-$C_4$ alkylcarbonylamino; —$S(O)_mR^3$; —$SO_2NR^{13}R^{14}$; —$NHSO_2R^{14}$; —$OCH_2CO_2R^{13}$; —$C(R^{14})$=$N(OR^{13})$;

$R^{12}$, when a substituent on nitrogen, is selected from the following:

phenyl; benzyl; phenethyl; hydroxy; $C_1$-$C_4$ hydroxyalkyl; $C_1$-$C_4$ alkyl; $C_3$-$C_6$ cycloalkyl; $C_3$-$C_6$ cycloalkylmethyl; —$CH_2NR^{13}R^{14}$; $C_{1-6}$ alkoxy-$C_{1-6}$ alkyl; $C_1$-$C_4$ haloalkyl; $C_1$-$C_4$ alkoxycarbonyl; $C_1$-$C_4$ alkylcarbonyl;

$R^{13}$ is selected from the following:

hydrogen;

phenyl substituted with 0–3 $R^{11a}$;

benzyl substituted with 0–3 $R^{11a}$;

$C_{1-4}$ alkyl substituted with 0–3 $R^{11a}$;

$C_{2-4}$ alkenyl substituted with 0–3 $R^{11a}$;

an amine protecting group when $R^{13}$ is bonded to N; or a hydroxy protecting group when $R^{13}$ is bonded to O;

$R^{14}$ is selected from the following:

hydrogen; $C_{2-4}$ alkenyl; phenyl; benzyl; an amine protecting group when $R^{14}$ is bonded to N; or $C_{1-4}$ alkyl substituted with 0–3 groups selected from OH, $C_1$-$C_4$ alkoxy, halogen;

$R^{13}$ and $R^{14}$, when attached to the same N atom, can alternatively join to form: —$(CH_2)_4$— or —$(CH_2)_5$—;

$R^{20}$ is selected from the following:

hydrogen;

$C_{1-4}$ alkyl substituted with 0–3 $R^{11}$;

$C_{1-5}$ alkoxycarbonyl substituted with 0–3 $R^{11}$;

benzoyl substituted with 0–3 $R^{12}$; or any group that, when administered to a mammalian subject, cleaves to form a free hydroxyl, amino or sulfhydryl;

$R^{22}$ and $R^{23}$ are independently selected from the following:

$C_{1-8}$ alkyl substituted with 1–3 $R^{31}$;

$C_{2-6}$ alkenyl substituted with 1–3 $R^{31}$;

$C_{2-4}$ alkynyl substituted with 0–3 $R^{31}$;

a $C_{3-10}$ carbocyclic ring system substituted with 1–5 $R^{31}$; and, a 5- to 10-membered heterocyclic ring system containing 1 to 3 heteroatoms independently selected from oxygen, nitrogen or sulfur, said heterocyclic ring system being substituted with 1–2 $R^{32}$;

$R^{22}$ and $R^{23}$ can independently be unsubstituted $C_{2-8}$ alkenyl when either $R^5$ or $R^6$ or both are halogen;

$R^{31}$ is selected from the following:

halogen; cyano; —$CH_2NR^{33}R^{14}$; —$NR^{33}R^{14}$; —$CO_2R^{13}$; —$C(=O)R^{33}$, —$OC(=O)R^{33}$; —$OR^{33}$; —$C(=O)$ $NR^{13}R^{14}$; $C_3$-$C_{10}$ cycloalkyl; nitro; formyl; $C_{1-4}$ haloalkyl; $C_{1-4}$ haloalkoxy; —$OCH_2CO_2R^{13}$; 2-(1-morpholino)ethoxy;

a $C_{5-10}$ carbocyclic residue substituted with 1–5 $R^{32}$; and, a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:

phenyl; phenethyl; phenoxy; benzyloxy; $C_3$-$C_{10}$ cycloalkyl; $C_3$-$C_6$ cycloalkylmethyl; $C_{2-6}$ alkoxy-$C_{2-6}$ alkyl; halogen; —$CO_2R^{13}$; —$CONR^{13}NR^{13}R^{14}$; cyano; —$CHO$; $C_3$-$C_6$ cycloalkoxy; —$NR^{13}R^{14}$; —$C(R^{14})$=$N(OR^{14})$; $NO_2$; —$OR^{13}$; $NR^{14}(C=O)R^{11}$; —$C(=O)NR^{11}R^{14}$; —$C(=O)NR^{13}R^{14}$; —$OC(=O)NR^{13}R^{14}$; —$C(=O)R^{11}$; —$OC(=O)R^{11}$; —$OCO_2R^{13}$; $C_1$-$C_4$ haloalkyl; $C_1$-$C_4$ haloalkoxy; $C_1$-$C_4$ alkyl substituted with 1–2 groups

79 selected from: $R^{11}$, $=NR^{14}$, $=NNR^{13}C(=O)NR^{13}R^{14}$ $=NNR^{13}C(=O)OR^{13}$ or $-NR^{13}R^{14}$;

$C_{2-4}$ alkenyl substituted with 1–2 $R^{11}$;

$C_{2-4}$ alkynyl substituted with 1–2 $R^{11}$; or a 5- to 10-membered heterocyclic ring containing from 1 to 3 heteroatoms independently selected from oxygen, nitrogen or sulfur, said heterocyclic ring being substituted with 0–2 $R^{12}$;

$R^{33}$ is selected from the following:

phenyl substituted with 0–3 $R^{11a}$;

benzyl substituted with 0–3 $R^{11a}$;

$C_{1-4}$ alkyl substituted with 1–3 $R^{11a}$;

$C_{2-4}$ alkenyl substituted with 0–3 $R^{11a}$; and, an amine protecting group when $R^{33}$ is bonded to N;

a hydroxy protecting group when $R^{33}$ is bonded to O;

provided that:

1) $R^4$ and $R^5$ together do not represent unsubstituted straight or branched alkyl; and, 2) only one of $R^5$ and $R^6$ can be H.

2. A compound according to claim 1, wherein the compound is of formula (IIb):

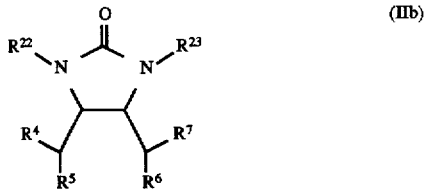

(IIb)

or pharmaceutically acceptable salt or prodrug form thereof, wherein;

$R^4$ and $R^7$ are independently selected from the following: $-NOR^{13}R^{13}$;

$C_{1-6}$ alkyl substituted with 0–2 $R^{11}$;

$C_{2-4}$ alkenyl substituted with 0–2 $R^{11}$; or a $C_5-C_{10}$ carbocyclic ring system substituted with 0–2 $R^{11}$ or $R^{12}$;

$R^5$ and $R^6$ are independently selected from the following: hydrogen, halogen, $-N(R^{20})_2$, $-OR^{20}$, $=O$, or $CH_2OH$;

$R^{11}$ is selected from the following:

hydrogen; halogen; cyano; $-NR^{13}R^{14}$; $-OR^{13}$; $C_{1-2}$ haloalkyl; $C_{1-2}$ alkyl substituted with 0–2 $R^{12}$;

a $C_{5-7}$ carbocyclic residue substituted with 0–2 $R^{12}$;

a 5- to 10-membered heterocyclic ring system containing 1 to 3 heteroatoms independently selected from oxygen, nitrogen or sulfur, said heterocyclic ring system being substituted with 0–2 $R^{12}$;

$R^{11a}$ is selected from the following: halogen; cyano; $-CH_2NH_2$; $-NH_2$; $-NH(C_1-C_3$ alkyl); $-OH$; $-C(=O)NH_2$; $C_3-C_6$ cycloalkyl; $C_3-C_6$ cycloalkylmethyl; phenoxy; benzyloxy; nitro; $C_1-C_4$ hydroxyalkyl; $C_1-C_4$ haloalkyl; or $C_1-C_4$ alkylcarbonyl;

$R^{12}$ is selected from the following:

phenyl; halogen; hydroxy; nitro; cyano; $C_1-C_4$ alkyl substituted with 0–2 $OR^{13}$, $SR^{13}$, or $NR^{11}R^{13}$; $C_3-C_6$ cycloalkylmethyl; $C_1-C_4$ alkoxy; $C_3-C_6$ cycloalkoxy; $-OR^{13}$; $-NR^{13}R^{14}$; $C_{1-6}$ alkoxy $C_{1-6}$ alkyl; $C_1-C_4$ hydroxyalkyl; $C_1-C_4$ haloalkyl; $C_1-C_4$ alkylcarbonyloxy; or $C_1-C_4$ alkylcarbonyl;

$R^{13}$ is selected from the following:

hydrogen;

phenyl substituted with 0–2 $R^{11a}$;

benzyl substituted with 0–2 $R^{11a}$;

$C_{1-4}$ alkyl substituted with 0–2 $R^{11a}$; or $C_{2-4}$ alkenyl substituted with 0–3 $R^{11a}$;

80

$R^{14}$ is selected from the following:

hydrogen; phenyl; benzyl; an amine protecting group when $R^{14}$ is bonded to N; or $C_{1-4}$ alkyl substituted with 0–3 groups selected from OH or halogen;

$R^{20}$ is selected from the following:

hydrogen;

$C_{1-5}$ alkoxycarbonyl substituted with 0–3 $R^{11}$;

benzoyl substituted with 0–3 $R^{12}$; or any group that, when administered to a mammalian subject, cleaves to form a free hydroxyl, amino or sulfhydryl;

m is 0, 1 or 2;

$R^{22}$ and $R^{23}$ are independently selected from the following:

$C_{1-6}$ alkyl substituted with 1-3 $R^{31}$;

$C_{2-4}$ alkenyl substituted with 1-3 $R^{31}$; or a $C_{3-10}$ carbocyclic ring system substituted with 1–2 $R^{31}$ or $R^{32}$;

$R^{22}$ and $R^{23}$ can independently be unsubstituted $C_{2-8}$ alkenyl when either $R^5$ or $R^6$ or both are halogen;

$R^{31}$ is selected from the following:

halogen; cyano; $-NR^{33}R^{14}$; $-CO_2R^{13}$; $-C(=O)R^{33}$; $-OC(=O)R^{33}$; $-OR^{33}$; $-C(=O)NR^{13}R^{14}$; $C_{3-7}$ cycloalkyl; nitro; $C_{1-4}$ haloalkyl;

a $C_{5-8}$ carbocyclic residue substituted with 1–3 $R^{32}$; or a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:

phenyl; phenethyl; phenoxy; benzyloxy; $C_{3-6}$ cycloalkyl; halogen; $-CO_2R^{13}$; cyano; $C_{3-6}$ cycloalkoxy; $-NR^{13}R^{14}$; $NO_2$; $-OR^{13}$; $NR^{14}(C=O)R^{11}$; $-C(=O)NR^{11}R^{14}$; $-C(=O)NR^{13}R^{14}$; $-C(O)R^{11}$; $-OC(=O)R^{11}$; $-OCO_2R^{13}$; $C_1-C_4$ haloalkyl; $C_1-C_4$ haloalkoxy; $C_1-C_4$ alkyl substituted with 1–2 groups selected from: $R^{11}$, $=NR^{14}$, or $-NR^{13}R^{14}$;

$C_{2-4}$ alkenyl substituted with 1–2 $R^{11}$; or a 5- to 10-membered heterocyclic ring containing from 1 to 3 heteroatoms independently selected from oxygen, nitrogen or sulfur, said heterocyclic ring being substituted with 0–2 $R^{12}$;

$R^{33}$ is selected from the following:

phenyl substituted with 0–2 $R^{11a}$;

benzyl substituted with 0–2 $R^{11a}$;

$C_{1-4}$ alkyl substituted with 1–2 $R^{11a}$; and, $C_{2-4}$ alkenyl substituted with 0–2 $R^{11a}$;

provided that:

1) $R^4$ and $R^5$ together do not represent unsubstituted straight or branched alkyl; and, 2) only one of $R^5$ and $R^6$ can be H.

3. A compound according to claim 2 or pharmaceutically acceptable salt or prodrug form thereof, wherein;

$R^4$ and $R^7$ are independently $C_{1-4}$ alkyl substituted with 0–2 $R^{11}$ or $-N(CH_3)(OCH_3)$;

$R^5$ and $R^6$ are independently selected from the following: hydrogen, halogen, $=O$, $CH_2OH$ or $-OR^{20}$;

$R^{11}$ is selected from the following:

hydrogen;

$C_{1-2}$ alkyl substituted with 0–2 $OR^{13}$;

phenyl substituted with 0–2 $R^{12}$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{12}$ is selected from the following:

$C_1$–$C_4$ alkyl; —$NR^{13}R^{14}$; —$OR^{13}$; $C_{1-2}$ alkoxy-$C_{1-2}$ alkyl-; or $R^{13}O$—$C_{1-2}$ alkyl-;

$R^{13}$ is selected from the following:
hydrogen;
phenyl substituted with 0–2 $R^{11a}$;
benzyl substituted with 0–2 $R^{11a}$; or
$C_{1-2}$ alkyl substituted with 0–2 $R^a$;

$R^{14}$ is selected from the following:
hydrogen or $C_{1-2}$ alkyl substituted with 0–2 OH or halogen $R^{20}$ is hydrogen or any group that, when administered to a mammalian subject, cleaves to form a free hydroxyl;

$R^{22}$ and $R^{23}$ are independently selected from the following:

$C_1$–$C_6$ alkyl substituted with $R^{31}$, or $C_2$–$C_3$ alkenyl substituted with $R^{31}$;

$R^{22}$ and $R^{23}$ can independently be unsubstituted $C_{2-8}$ alkenyl when either $R^5$ or $R^6$ or both are halogen;

$R^{31}$ is selected from the following:

$C_{3-5}$ cycloalkyl; $C_{5-7}$ carbocyclic substituted with 1-2 $R^{32}$; and, a 5- to 10-membered heterocyclic ring system containing 1 to 3 heteroatoms independently selected from oxygen, nitrogen or sulfur, said heterocyclic ring system being substituted with 0–2 $R^{12}$; and $R^{32}$ is selected from the following:
—$C(=O)NR^{11}R^{14}$; —$NR^{14}C(=O)R^{11}$; halogen; cyano; —$NR^{13}R^{14}$; —$OR^{13}$; —$CO_2R^{13}$; —$C(=O) R^{11}$;

$C_1$–$C_2$ alkyl substituted with 0–2 groups selected from: —$OR^{13}$, =$NR^{14}$, or —$NR^{13}R^{14}$; or a 5- to 10-membered heterocyclic ring system containing 1 to 3 heteroatoms independently selected from oxygen, nitrogen or sulfur, said heterocyclic ring system being substituted with 0–2 $R^{12}$;

provided that:
1) $R^4$ and $R^5$ together do not represent unsubstituted straight or branched alkyl; and,
2) only one of $R^5$ and $R^6$ can be H.

4. A compound according to claim 3, wherein the compound is of formula (IIc):

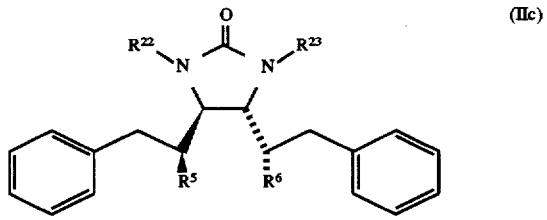

(IIc)

or pharmaceutically acceptable salt or prodrug forms thereof, wherein;

$R^5$ and $R^6$ are independently selected from the following: hydrogen, hydroxy, F, Cl, Br, I, or $CH_2OH$;

$R^{22}$ and $R^{23}$ are independently —$CH_2$—$R^{31}$;

$R^{22}$ and $R^{23}$ independently may also be allyl when either $R^5$ or $R^6$ or both are halogen;

$R^{31}$ is selected from the following: cyclopropyl, phenyl substituted with 1-2 $R^{32}$, naphthyl, pyridyl; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{12}$ is selected from the following: methyl, ethyl, propyl, n-butyl, t-butyl, amino, methylamino, dimethylamino, ethylamino, diethylamino, methoxy, ethoxy, OH, $CH_3OCH_2$—, $CH_3CH_2OCH_2$—, phenoxymethyl, or benzyloxymethyl;

$R^{32}$ is selected from the following: —$C(=O)NR^{11}R^{14}$; —$NHC(=O)R^{11}$; F; I; cyano; methyl, —$CH_2OH$; —$CH_2CH_2OH$; —OH, —$CO_2CH_3$; —$C(O)CH_3$; pyridyl; ($CH_3C(=NOH)$; ($H_2NC((=NOH)$; or a 5- to 10-membered heterocyclic ring system containing 1 to 3 heteroatoms independently selected from oxygen, nitrogen or sulfur, said heterocyclic ring system being substituted with 0–2 $R^{12}$;

$R^{11}$ is selected from the following: hydrogen; —$CH_2OH$; —$CH_2CH_2OH$; or a 5- to 10-membered heterocyclic ring system containing 1 to 3 heteroatoms independently selected from oxygen, nitrogen or sulfur, said heterocyclic ring system being substituted with 0–2 $R^{12}$; and $R^{14}$ is selected from the following: hydrogen, —$CH_2OH$, or —$CH_2CH_2OH$.

5. A compound according to claim 4 or pharmaceutically acceptable salt or prodrug forms thereof, wherein;

$R^5$ and $R^6$ are independently selected from H, OH, F, Br, or $CH_2OH$; and $R^{22}$ and $R^{23}$ are as follows:
$R^{22}$ is cyclopropylmethyl and $R^{23}$ is benzyl;
$R^{22}$ is cyclopropylmethyl and $R^{23}$ is 3-hydroxybenzyl;
$R^{22}$ is cyclopropylmethyl and $R^{23}$ is 4-hydroxybenzyl;
$R^{22}$ is cyclopropylmethyl and $R^{23}$ is 3-aminobenzyl;
$R^{22}$ is cyclopropylmethyl and $R^{23}$ is 4-pyridylmethyl;
$R^{22}$ is 3-aminobenzyl and $R^{23}$ is 2-naphthylmethyl;
$R^{22}$ is 3-aminobenzyl and $R^{23}$ is 4-hydroxymethylbenzyl;
$R^{22}$ is 3-aminobenzyl and $R^{23}$ is 3-hydroxybenzyl
$R^{22}$ is 4-hydroxymethylbenzyl and $R^{23}$ is 3-hydroxybenzyl;
$R^{22}$ is 2-naphthylmethyl and $R^{23}$ is 4-hydroxymethylbenzyl;
$R^{22}$ is allyl and $R^{23}$ is benzyl;
$R^{22}$ is benzyl and $R^{23}$ is 3-hydroxybenzyl;
$R^{22}$ is benzyl and $R^{23}$ is 2-naphthylmethyl; or
$R^{22}$ is benzyl and $R^{23}$ is 4-pyridylmethyl;

$R^{22}$ and $R^{23}$ are independently the same group and are selected from the following:
cyclopropylmethyl;
4-fluorobenzyl;
3-iodobenzyl;
2-napthylmethyl;
2-pyridylmethyl;
3-pyridylmethyl;
4-pyridylmethyl;
3-(2-pyridyl)benzyl;
3-(3'-pyridyl)benzyl;
3-(4-pyridyl)benzyl;
3-methylbenzyl;
3-ethylbenzyl;
3-cyanobenzyl;
3-hydroxybenzyl;
4-hydroxybenzyl;
3,4-dihydroxybenzyl;
3-hydroxymethylbenzyl;
4-hydroxymethylbenzyl;
3-(2-hydroxyethyl)benzyl;
3-acetylbenzyl;
3-($CH_3C(=NOH)$)benzyl;
3-($H_2NC(=N—OH)$)benzyl;
3-aminobenzyl;
4-aminobenzyl;
3-aminocarbonylbenzyl;
3-N-methylaminocarbonylbenzyl;

3-N,N-dimethylaminocarbonylbenzyl;
3-N-ethylaminocarbonylbenzyl;
3-N,N-diethylaminocarbonylbenzyl;
3-(2-hydroxymethylaminocarbonyl)benzyl;
3-(2-hydroxyethylaminocarbonyl)benzyl;
5-indazolylmethyl;
6-indazolylmethyl;
3-aminoindazol-5-ylmethyl;
3-(methylamino)indazol-5-ylmethyl;
3-(dimethylamino)indazol-5-ylmethyl;
3-(ethylamino)indazol-5-ylmethyl;
3-(diethylamino)indazol-5-ylmethyl;
3-methoxy-indazol-5-ylmethyl;
3-ethoxy-indazol-5-ylmethyl;
3-(phenoxymethyl)indazol-5-ylmethyl;
3-methylindazol-5-ylmethyl;
3-ethylindazol-5-ylmethyl;
indazolinon-5-ylmethyl;
indazolinon-6-ylmethyl;
benzoxazolinon-5-ylmethyl;
benzoxazolinon-6-ylmethyl;
5-benzisoxazolyl-5-methyl
3-methylbenzisoxazol-5-ylmethyl;
3-ethylbenzisoxazol-5-ylmethyl;
3-aminobenzisoxazol-5-ylmethyl;
3-(methylamino)benzisoxazol-5-ylmethyl;
3-(dimethylamino)benzisoxazol-5-ylmethyl;
3-(ethylamino)benzisoxazol-5-ylmethyl;
3-(diethylamino)benzisoxazol-5-ylmethyl;
5-benzisothiazolylmethyl;
3-methylbenzisothiazol-5-ylmethyl;
3-ethylbenzisothiazol-5-ylmethyl;
3-aminobenzisothiazol-5-ylmethyl;
3-(methylamino)benzisothiazol-5-ylmethyl;
3-(dimethylamino)benzisothiazol-5-ylmethyl;
3-(ethylamino)benzisothiazol-5-ylmethyl;
3-(diethylamino)benzisothiazol-5-ylmethyl;
3-diazol-3'-yl)benzyl;
3-(4'-methyldiazol-3'-yl)benzyl;
3-(5'-methyldiazol-3'-yl)benzyl;
3-(4'-ethyldiazol-3'-yl)benzyl;
3-(5'-ethyldiazol-3'-yl)benzyl;
3-(4',5'-dimethyldiazol-3'-yl)benzyl;
3-(4',5'-diethyldiazol-3'-yl)benzyl;
3-(4'-aminodiazol-3'-yl)benzyl;
3-(5'-aminodiazol-3'-yl)benzyl;
3-(4'-(methylamino)diazol-3'-yl)benzyl;
3-(5'-(methylamino)diazol-3'-yl)benzyl;
3-(4'-(ethylamino)diazol-3'-yl)benzyl;
3-(5'-(ethylamino)diazol-3'-yl)benzyl;
3-(4'-(dimethylamino)diazol-3'-yl)benzyl;
3-(5'-(dimethylamino)diazol-3'-yl)benzyl;
3-(4'-(diethylamino)diazol-3'-yl)benzyl;
3-(5'-(diethylamino)diazol-3'-yl)benzyl;
3-oxazol-3'-ylbenzyl;
3-(4'-methyloxazol-3'-yl)benzyl;
3-(5'-methyloxazol-3'-yl)benzyl;
3-(4'-ethyloxazol-3'-yl)benzyl;
3-(5'-ethyloxazol-3'-yl)benzyl;
3-(4',5'-dimethyloxazol-3'-yl)benzyl;
3-(4',5'-diethyloxazol-3'-yl)benzyl;
3-(4'-aminooxazol-3'-yl)benzyl;
3-(5'-aminooxazol-3'-yl)benzyl;
3-(4'-(methylamino)oxazol-3'-yl)benzyl;
3-(5'-(methylamino)oxazol-3'-yl)benzyl;
3-(4'-(dimethylamino)oxazol-3'-yl)benzyl;
3-(5'-(dimethylamino)oxazol-3'-yl)benzyl;
3-(4'-(dimethylamino)oxazol-3'-yl)benzyl;
3-(5'-(ethylamiino)oxazol-3'-yl)benzyl;
3-(4'-(diethylamino)oxazol-3'-yl)benzyl;
3-(5'-(diethylamino)oxazol-3'-yl)benzyl;
3-isoxazol-3'-ylbenzyl;
3-(4'-methylisoxazol-3'-yl)benzyl;
3-(5'-methylisoxazol-3'-yl)benzyl;
3-(4'-ethylisoxazol-3'-yl)benzyl;
3-(5'-ethylisoxazol-3'-yl)benzyl;
3-(4',5'-dimethylisoxazol-3'-yl)benzyl;
3-(4',5'-diethylisoxazol-3'-yl)benzyl;
3-(4'-aminoisoxazol-3'-yl)benzyl;
3-(5'-aminoisoxazol-3'-yl)benzyl;
3-(4'-(methylamino)isoxazol-3'-yl)benzyl;
3-(5'-(methylanino)isoxazol-3'-yl)benzyl;
3-(4'-(dimethylamino)isoxazol-3'-yl)benzyl;
3-(5'-(dimethylamino)isoxazol-3'-yl)benzyl;
3-(4'-(ethylamino)isoxazol-3'-yl)benzyl;
3-(5'-(ethylamino)isoxazol-3'-yl)benzyl;
3-(4'-(diethylamino)isoxazol-3'-yl)benzyl;
3-(5'-(diethylamino)isoxazol-3'-yl)benzyl;
3-(2-triazolyl)benzyl;
3-(5-methyltriazol-2-yl)benzyl;
3-(5-ethyltriazol-2-yl)benzyl;
3-(5-aminotriazol-2-yl)benzyl;
3-(5-(methylamino)triazol-2-yl)benzyl;
3-(5-(dimethylamino)triazol-2-yl)benzyl;
3-(5-(ethylamino)triazol-2-yl)benzyl;
3-(5-(diethylamino)triazol-2-yl)benzyl;
3-triazol-3'-ylbenzyl;
3-(5'-methyltriazol-3'-yl)benzyl;
3-(5'-ethyltriazol-3'-yl)benzyl;
3-(5'-aminotriazol-3'-yl)benzyl;
3-(5'-(methylamino)triazol-3'-yl)benzyl;
3-(5'-(dimethylamino)triazol-3'-yl)benzyl;
3-(5'-(ethylamino)triazol-3'-yl)benzyl;
3-(5'-(diethylamino)triazol-3'-yl)benzyl;
3-(2-imidazolyl)benzyl;
3-(4-methylimidazol-2-yl)benzyl;
3-(4,5-dimethylimidazol-2-yl)benzyl;
4-aminoimidazol-2-yl)benzyl;
3-(4-(methylamino)imidazol-2-yl)benzyl;
3-(4-(dimethylamino)imidazol-2-yl)benzyl;
3-(4-(ethylamino)imidazol-2-yl)benzyl;
3-(4-(diethylamino)imidazol-2-yl)benzyl;
3-(5-aminoimidazol-2-yl)benzyl,
3-(5-(methylamino)imidazol-2-yl)benzyl;
3-(5-(dimethylamino)imidazol-2-yl)benzyl;
3-(5-(ethylamino)imidazol-2-yl)benzyl;
3-(5-(diethylamino)imidazol-2-yl)benzyl;
3-(2-imidazolyl-aminocarbonyl)benzyl;
3-(4-methylimidazol-2-yl-aminocarbonyl)benzyl;
3-(4,5-dimethylimidazol-2-yl-aminocarbonyl)benzyl;
3-(4-aminoimidazol-2-yl-aminocarbonyl)benzyl;
3-(4-(methylamino)imidazol-2-yl-aminocarbonyl)benzyl;
3-(4-(dimethylamino)imidazol-2-yl-aminocarbonyl)benzyl;
3-(4-(ethylamino)imidazol-2-yl-aminocarbonyl)benzyl;
3-(4-(diethylamino)imidazol-2-yl-aminocarbonyl)benzyl;
3-(5-aminoimidazol-2-yl-aminocarbonyl)benzyl;
3-(5-(methylamino)imidazol-2-yl-aminocarbonyl)benzyl;
3-(5-(dimethylamino)imidazol-2-yl-aminocarbonyl)benzyl;
3-(5-(ethylamino)imidazol-2-yl-aminocarbonyl)benzyl;
3-(5-(diethylamino)imidazol-2-yl-aminocarbonyl)benzyl;
3-(2-pyridyl-aminocarbonyl)benzyl;
3-(3'-pyridyl-aminocarbonyl)benzyl;
3-(4-pyridyl-aminocarbonyl)benzyl;
3-(1',3',4'-thiadiazol-2'-yl-aminocarbonyl)benzyl;

3-(5-methylthiadiazol-2-yl-aminocarbonyl)benzyl;
3-(5-ethylthiadiazol-2-yl-aminocarbonyl)benzyl;
3-(5-t-butylthiadiazol-2-yl-aminocarbonyl)benzyl;
3-(5-aminothiadiazol-2-yl-aminocarbonyl)benzyl;
3-(5-(methylamino)thiadiazol-2-yl-aminocarbonyl)benzyl;
3-(5-(dimethylamino)thiadiazol-2-yl-aminocarbonyl)benzyl;
3-(5-(ethylamino)thiadiazol-2-yl-aminocarbonyl)benzyl;
3-(5-(diethylamino)thiadiazol-2-yl-aminocarbonyl)benzyl;
3-(2-thiazolyl-aminocarbonyl)benzyl;
3-(4-methylthiazol-2-yl-aminocarbonyl)benzyl;
3-(5-methylthiazol-2-yl-aminocarbonyl)benzyl;
3-(4,5-dimethylthiazol-2-yl-aminocarbonyl)benzyl;
3-(4-ethylthiazol-2-yl-aminocarbonyl)benzyl;
3-(5-ethylthiazol-2-yl-aminocarbonyl)benzyl;
3-(4,5-diethylthiazol-2-yl-aminocarbonyl)benzyl;
3-(4-aminothiazol-2-yl-aminocarbonyl)benzyl;
3-(5-aminothiazol-2-yl-aminocarbonyl)benzyl;
3-(4-(methylamino)thiazol-2-yl-aminocarbonyl)benzyl;
3-(5-(methylamino)thiazol-2-yl-aminocarbonyl)benzyl;
3-(4-(ethylamino)thiazol-2-yl-aminocarbonyl)benzyl;
3-(5-(ethylamino)thiazol-2-yl-aminocarbonyl)benzyl;
3-(2-triazolyl-aminocarbonyl)benzyl;
3-(5-methyltriazol-2-yl-aminocarbonyl)benzyl;
3-(5-ethyltriazol-2-yl-aminocarbonyl)benzyl;
3-(5-aminotriazol-2-yl-aminocarbonyl)benzyl;
3-(5-(methylamino)triazol-2-yl-aminocarbonyl)benzyl;
3-(5-(dimethylamino)triazol-2-yl-aminocarbonyl)benzyl;
3-(5-(ethylamino)triazol-2-yl-aminocarbonyl)benzyl; or
3-(5-(diethylamino)triazol-2-yl-aminocarbonyl)benzyl; or when at least on of $R^5$ or $R^6$ is other than H, $R^{22}$ or $R^{23}$ may, independently, both be allyl.

6. A compound according to claim 5 or pharmaceutically acceptable salt or prodrug forms thereof, wherein:

$R^5$ and $R^6$ are both F;

$R^5$ and $R^6$ are both $CH_2OH$;

$R^5$ is H and $R^6$ is $CH_2OH$;

$R^5$ is H and $R^6$ is OH; or $R^5$ is H and $R^6$ is Br.

7. A pharmaceutical composition, comprising: a pharmaceutically acceptable carrier and a therapeutically effective amount of a compound of claim 1 or a pharmaceutically acceptable salt or prodrug form thereof.

8. A pharmaceutical composition, comprising: a pharmaceutically acceptable carrier and a therapeutically effective amount of a compound of claim 2 or a pharmaceutically acceptable salt or prodrug form thereof.

9. A pharmaceutical composition, comprising: a pharmaceutically acceptable carrier and a therapeutically effective amount of a compound of claim 3 or a pharmaceutically acceptable salt or prodrug form thereof.

10. A pharmaceutical composition, comprising: a pharmaceutically acceptable carrier and a therapeutically effective amount of a compound of claim 4 or a pharmaceutically acceptable salt or prodrug form thereof.

11. A pharmaceutical composition, comprising: a pharmaceutically acceptable carrier and a therapeutically effective amount of a compound of claim 5 or a pharmaceutically acceptable salt or prodrug form thereof.

12. A pharmaceutical composition, comprising: a pharmaceutically acceptable carrier and a therapeutically effective amount of a compound of claim 6 or a pharmaceutically acceptable salt or prodrug form thereof.

13. A method for treating viral infections, comprising: administering to a host in need of such treatment a therapeutically effective amount of a compound of claim 1 or a pharmaceutically acceptable salt or prodrug form thereof.

14. A method for treating viral infections, comprising: administering to a host in need of such treatment a therapeutically effective amount of a compound of claim 2 or a pharmaceutically acceptable salt or prodrug form thereof.

15. A method for treating viral infections, comprising: administering to a host in need of such treatment a therapeutically effective amount of a compound of claim 3 or a pharmaceutically acceptable salt or prodrug form thereof.

16. A method for treating viral infections, comprising: administering to a host in need of such treatment a therapeutically effective amount of a compound of claim 4 or a pharmaceutically acceptable salt or prodrug form thereof.

17. A method for treating viral infections, comprising: administering to a host in need of such treatment a therapeutically effective amount of a compound of claim 5 or a pharmaceutically acceptable salt or prodrug form thereof.

18. A method for treating viral infections, comprising: administering to a host in need of such treatment a therapeutically effective amount of a compound of claim 6 or a pharmaceutically acceptable salt or prodrug form thereof.

* * * * *